(12) United States Patent
Carter et al.

(10) Patent No.: US 7,198,789 B2
(45) Date of Patent: *Apr. 3, 2007

(54) METHODS AND COMPOSITIONS FOR MODULATING INTERLEUKIN-21 RECEPTOR ACTIVITY

(75) Inventors: Laura Carter, Medford, MA (US); Beatriz Carreno, Acton, MA (US); Leslie D. Lowe, Sudbury, MA (US); Matthew J. Whitters, Hudson, MA (US); Kyri Dunussi, Belmont, MA (US); Mary Collins, Natick, MA (US); Margery Ma, W. Roxbury, MA (US); Deborah A. Young, Melrose, MA (US); JoAnn S. Witek, Acton, MA (US); Glenn Larsen, Sudbury, MA (US); Marion T. Kasaian, Charlestown, MA (US); Debra D. Donaldson, Medford, MA (US); Michelle Unger, Chapel Hill, NC (US)

(73) Assignee: Genetics Institute, LLC, Cambridge, MA (US)

( * ) Notice: Subject to any disclaimer, the term of this patent is extended or adjusted under 35 U.S.C. 154(b) by 313 days.

This patent is subject to a terminal disclaimer.

(21) Appl. No.: 10/264,634

(22) Filed: Oct. 4, 2002

(65) Prior Publication Data
US 2003/0108549 A1 Jun. 12, 2003

Related U.S. Application Data

(63) Continuation-in-part of application No. 09/972,218, filed on Oct. 4, 2001, which is a continuation-in-part of application No. 09/569,384, filed on May 11, 2000, which is a continuation-in-part of application No. 09/560,766, filed on Apr. 28, 2000, now abandoned, which is a continuation of application No. 09/040,005, filed on Mar. 17, 1998, now Pat. No. 6,057,128.

(60) Provisional application No. 60/373,746, filed on Apr. 17, 2002.

(51) Int. Cl.
*A61K 39/00* (2006.01)
*A61K 39/395* (2006.01)
*A61K 38/17* (2006.01)

(52) U.S. Cl. .............. 424/130.1; 424/143.1; 424/141.1; 424/133.1; 424/135.1; 514/2; 530/350; 530/388.22; 530/388.1; 530/387.1; 530/387.3; 530/387.9; 536/23.5

(58) Field of Classification Search ............... 530/350, 530/388.22, 389.1; 514/2, 1
See application file for complete search history.

(56) References Cited

U.S. PATENT DOCUMENTS

| 5,011,912 A | 4/1991 | Hopp et al. |
|---|---|---|
| 5,098,833 A | 3/1992 | Lasky et al. |
| 5,116,964 A | 5/1992 | Capon et al. |
| 5,155,027 A | 10/1992 | Sledziewski et al. |
| 5,216,131 A | 6/1993 | Lasky et al. |
| 5,225,538 A | 7/1993 | Capon et al. |
| 5,428,130 A | 6/1995 | Capon et al. |
| 5,447,851 A | 9/1995 | Beutler et al. |
| 5,455,165 A | 10/1995 | Capon et al. |
| 5,514,582 A | 5/1996 | Capon et al. |
| 5,567,584 A | 10/1996 | Sledziewski et al. |
| 5,714,147 A | 2/1998 | Capon et al. |
| 5,750,375 A | 5/1998 | Sledziewski et al. |
| 5,840,844 A | 11/1998 | Lasky et al. |
| 5,843,725 A | 12/1998 | Sledziewski et al. |
| 6,018,026 A | 1/2000 | Sledziewski et al. |
| 6,057,128 A | 5/2000 | Donaldson et al. |
| 6,136,310 A | 10/2000 | Hanna et al. |
| 6,291,212 B1 | 9/2001 | Sledziewski et al. |
| 6,291,646 B1 | 9/2001 | Sledziewski et al. |
| 6,300,099 B1 | 10/2001 | Sledziewski et al. |

(Continued)

FOREIGN PATENT DOCUMENTS

EP 0 812 913 12/1997

(Continued)

OTHER PUBLICATIONS

D'Andrea et al., "Expression cloning of the murine erythropoietin receptor," *Cell*, 57:277-285 (1989).
Hatakeyama et al., "Interleukin-2 receptor beta chain gene: Generation of three receptor forms by cloned human alpha and beta chain cDNA's," *Science*, 244:551-556 (1989).
GenBank Accession No. M26062 Human interleukin 2 receptor beta chain (p70-75) mRNA, complete cds.
Yan et al., "Two-Amino Acid Molecular Switch in an Epithelial Morphogen That Regulates Binding to Two Distinct Receptors," *Science*, 290:523-527 (2000).
Parrish-Novak, et al., "Interleukin 21 and its receptor are involved in NK cell expansion and regulation of lymphocyte function," *Nature*, 408:57-63 (2000).

(Continued)

*Primary Examiner*—Eileen B. O'Hara
(74) *Attorney, Agent, or Firm*—Fitzpatrick, Cella, Harper & Scinto

(57) ABSTRACT

Methods and compositions for modulating interleukin-21 (IL-21)/IL-21 receptor (MU-1) activity using agonists or antagonists of IL-21 or IL-21 receptor ("IL-21R" or "MU-1"), are disclosed. IL-21/IL-21R antagonists can be used to induce immune suppression in vivo, e.g., for treating or preventing immune cell-associated pathologies (e.g., pathologies associated with aberrant activity of one or more of mature T cells (mature CD8+, mature CD4+ T cells), mature NK cells, B cells, macrophages and megakaryocytes, including transplant rejection and autoimmune disorders). IL-21/IL-21R agonists can be used by themselves or in combination with an antigen, e.g., as an adjuvant (e.g., a vaccine adjuvant), to up-regulate an immune response in vivo, e.g., for example, for use in treating cancer and infectious disorders.

66 Claims, 47 Drawing Sheets

U.S. PATENT DOCUMENTS

| | | |
|---|---|---|
| 6,307,024 B1 | 10/2001 | Novak et al. |
| 6,323,323 B1 | 11/2001 | Sledziewski et al. |
| 6,406,697 B1 | 6/2002 | Capon et al. |
| 6,576,744 B1* | 6/2003 | Presnell et al. ............. 530/351 |
| 6,692,924 B2 | 2/2004 | Presnell et al. |
| 2001/0025022 A1 | 9/2001 | Kikly et al. |
| 2002/0090680 A1 | 7/2002 | Hodge |
| 2002/0128446 A1 | 9/2002 | Novak et al. |
| 2002/0137677 A1 | 9/2002 | Sprecher et al. |
| 2002/0160451 A1 | 10/2002 | Masiakowski et al. |
| 2003/0134390 A1 | 7/2003 | Presnell et al. |
| 2003/0148447 A1 | 8/2003 | Presnell et al. |

FOREIGN PATENT DOCUMENTS

| | | |
|---|---|---|
| EP | 1 088 831 | 4/2001 |
| WO | WO 96/04388 | 2/1996 |
| WO | WO 97/20926 | 6/1997 |
| WO | WO 97/31946 | 9/1997 |
| WO | WO 97/33913 | 9/1997 |
| WO | WO 97/47741 | 12/1997 |
| WO | WO 97/47742 | 12/1997 |
| WO | WO 98/10638 | 3/1998 |
| WO | WO 98/11225 | 3/1998 |
| WO | WO 98/31811 | 7/1998 |
| WO | WO 99/47675 | 9/1999 |
| WO | WO 99/67290 | 12/1999 |
| WO | WO 00/08152 | 2/2000 |
| WO | WO 00/17235 | 3/2000 |
| WO | WO 00/27882 | 5/2000 |
| WO | WO 00/53761 | 9/2000 |
| WO | WO 00/69880 | 11/2000 |
| WO | WO 01/36467 | 5/2001 |
| WO | WO 01/46261 | 6/2001 |
| WO | WO 01/77171 | 10/2001 |

OTHER PUBLICATIONS

Ozaki, et al., "Cloning of a type I cytokine receptor most related to the IL-2 receptor β chain," *Proc. Natl. Acad. Sci. USA*, 97(21):11439-11444 (2000).

EMBL Database Accession No. AC002302 (Jun. 26, 1997).

Bazan, "Structural design and molecular evolution of a cytokine receptor superfamily" *Proc. Natl. Acad. Sci. USA*, 87:6934-6938, (1990).

Dusanter-Fourt, et al., "Tranduction du signal par les recepteurs de cytokines" *Medecine/Sciences* 10:825-835. English Abstract.

O'Dowd, et al., "Cloning and chromosomal mapping of four putative novel human G-protein-coupled receptor genes," *Gene* 187(1):75-81, (1997).

International Search Report for PCT/US 99/05854. Mailed on Aug. 17, 1999.

Database EMBL. ID HS795114, Accession No. R52795, May 25, 1995.

Caput, D., et al., "Cloning and characterization of a specific interleukin (IL)-13 binding protein structurally related to the IL-5 receptor a chain," *The Journal of Biological Chemistry*, 271(28):16921-16926, (1996).

Vita, N., et al., "Characterization and comparison of the interleukin 13 receptor with the interleukin 4 receptor on several cell types," *Journal of Biological Chemistry*, 270(8):3512-3517, (1995).

Biró, et al., "The effects of wsews pentapeptide and wsews-specific monoclonal antibodies on constitutive and 11-6 induced acute phase," *Immunology Letters*, 46:183-187, (1995).

Zhang, et al., "Identification, purification, and characterization of a soluble interleukin (IL)-13 binding protein," *Journal of Biological Chemistry*, 272(14):9474-9480, (1997).

Debinski, W., et al., "A novel chimeric protein composed of interleukin-13 and pseudomonas exotoxin is highly cytotoxic to human carcinoma cells expressing receptors for interleukin-13 and interleukin-4," *Journal of Biological Chemistry*, 270(28):16775-16780, (1995).

Page, L.A., et al., "An antiproliferative bioassay for interleukin-4," *Journal of Immunological Methods*, 189(1):129-135, (1996).

Lai Chun-Fai, et al., "STAT3 and STAT5B are targets of two different signal pathways activated by hematopoietin receptors and control transcription via separate cytokine response elements," *Journal of Biological Chemistry*, 270(40):23254-23257, (1995).

Database EMBL, Accession No. AF279436, Jul. 18, 2000.

Database EMBL, Accession No. AB049137, Sep. 23, 2000.

Bazan "Structural design and molecular evolution of a cytokine receptor superfamily," Proc. Natl. Acad. Sci. USA 87:6934-38 (1990).

Imler et al. "Identification of three adjacent amino acids of interleukin-2 receptor β chain which control the affinity and the specificity of the interaction with interleukin-2," EMBO J. 11:2047-53 (1992).

LaRosa et al. "Amino Terminus of the Interleukin-8 Receptor Is a Major Determinant of Receptor Subtype Specificity," J. Biol. Chem. 267:25402-06 (1992).

Schimmenti et al. "Localization of an essential ligand binding determinant of the human erythropoietin receptor to a domin N-terminal to the WSXWS motif: implications for soluble receptor function," Exp. Hematol. 23:1341-46 (1995).

Mulhern et al. "The Solution Structure of the Cytokine-binding Domain of the Common β-Chain of the Receptors for Granulocyte-Macrophage Colony-stimulating Factor, Interleukin-3 and Interleukin-5," J. Mol. Biol. 297:989-1001 (2000).

Woodcock et al. "Three residues in the common β chain of the human GM-CSF, IL-3 and IL-5 receptors are essential for GM-CSF and IL-5 but not IL-3 high affinity binding and interact with Glu21 of GM-CSF," EMBO J. 13:5176-85 (1994).

* cited by examiner

FIG. 1A

```
   1  CTCGACGCGG CGGTACCAGC TGTCTGCCCA CTTCTCCTGT GGTGTGCCTC
  51  ACGGTCACTT GCTTGTCTGA CCGCAAGTCT GCCCATCCCT GGGGCAGCCA
 101  ACTGCCCTCA GCCCGTGCCC CAGGCGTGCC CTGTCTCTGT CTGGCTGCCC
 151  CAGCCCTACT GTCTTCCTCT GTGTAGGCTC TGCCCAGATG CCCGGCTGGT
 201  CCTCAGCCTC AGGACTATCT CAGCAGTGAC TCCCCTGATT CTGGACTTGC
 251  ACCTGACTGA ACTCCTGCCC ACCTCAAACC TTCACCTCCC ACCACCACCA
 301  CTCCGAGTCC CGCTGTGACT CCCACGCCCA GGACACCACC CAAGTGCCCC
 351  AGCCTAAAGA ATGGCTTTCT GAGAAAGACC CTGAAGGAGT AGGTCTGGGA
 401  CACAGCATGC CCCGGGGCCC AGTGGCTGCC TTACTCCTGC TGATTCTCCA
 451  TGGAGCTTGG AGCTGCCTGG ACCTCACTTG CTACACTGAC TACCTCTGGA
 501  CCATCACCTG TGTCCTGGAG ACACGGAGCC CCAACCCCAG CATACTCAGT
 551  CTCACCTGGC AAGATGAATA TGAGGAACTT CAGGACCAAG AGACCTTCTG
 601  CAGCCTACAC AGGTCTGGCC ACAACACCAC ACATATATGG TACACGTGCC
 651  ATATGCGCTT GTCTCAATTC CTGTCCGATG AAGTTTTCAT TGTCAATGTG
 701  ACGGACCAGT CTGGCAACAA CTCCCAAGAG TGTGGCAGCT TTGTCCTGGC
 751  TGAGAGCATC AAACCAGCTC CCCCCTTGAA CGTGACTGTG GCCTTCTCAG
 801  GACGCTATGA TATCTCCTGG GACTCAGCTT ATGACGAACC CTCCAACTAC
 851  GTGCTGAGGG GCAAGCTACA ATATGAGCTG CAGTATCGGA ACCTCAGAGA
 901  CCCCTATGCT GTGAGGCCGG TGACCAAGCT GATCTCAGTG GACTCAAGAA
 951  ACGTCTCTCT TCTCCCTGAA GAGTTCCACA AAGATTCTAG CTACCAGCTG
1001  CAGGTGCGGG CAGCGCCTCA GCCAGGCACT TCATTCAGGG GGACCTGGAG
1051  TGAGTGGAGT GACCCCGTCA TCTTTCAGAC CCAGGCTGGG GAGCCCGAGG
1101  CAGGCTGGGA CCCTCACATG CTGCTGCTCC TGGCTGTCTT GATCATTGTC
1151  CTGGTTTTCA TGGGTCTGAA GATCCACCTG CCTTGGAGGC TATGGAAAAA
1201  GATATGGGCA CCAGTGCCCA CCCCTGAGAG TTTCTTCCAG CCCCTGTACA
1251  GGGAGCACAG CGGGAACTTC AAGAAATGGG TTAATACCCC TTTCACGGCC
1301  TCCAGCATAG AGTTGGTGCC ACAGAGTTCC ACAACAACAT CAGCCTTACA
1351  TCTGTCATTG TATCCAGCCA AGGAGAAGAA GTTCCCGGGG CTGCCGGGTC
1401  TGGAAGAGCA ACTGGACTGT GATGGAATGT CTGAGCCTGG TCACTGGTGC
```

FIG. 1B

```
1451  ATAATCCCCT TGGCAGCTGG CCAAGCGGTC TCAGCCTACA GTGAGGAGAG
1501  AGACCGGCCA TATGGTCTGG TGTCCATTGA CACAGTGACT GTGGGAGATG
1551  CAGAGGGCCT GTGTGTCTGG CCCTGTAGCT GTGAGGATGA TGGCTATCCA
1601  GCCATGAACC TGGATGCTGG CCGAGAGTCT GGCCCTAATT CAGAGGATCT
1651  GCTCTTGGTC ACAGACCCTG CTTTTCTGTC TTGCGGCTGT GTCTCAGGTA
1701  GTGGTCTCAG GCTTGGAGGC TCCCCAGGCA GCCTACTGGA CAGGTTGAGG
1751  CTGTCATTTG CAAAGGAAGG GGACTGGACA GCAGACCCAA CCTGGAGAAC
1801  TGGGTCCCCA GGAGGGGCT CTGAGAGTGA AGCAGGTTCC CCCCCTGGTC
1851  TGGACATGGA CACATTTGAC AGTGGCTTTG CAGGTTCAGA CTGTGGCAGC
1901  CCCGTGGAGA CTGATGAAGG ACCCCCTCGA AGCTATCTCC GCCAGTGGGT
1951  GGTCAGGACC CCTCCACCTG TGGACAGTGG AGCCCAGAGC AGCTAGCATA
2001  TAATAACCAG CTATAGTGAG AAGAGGCCTC TGAGCCTGGC ATTTACAGTG
2051  TGAACATGTA GGGGTGTGTG TGTGTGTGTG TGTGTGTGTG TGTGTGTGTG
2101  TGTGTGTGTG TGTGTGTGTG TGTCTTGGGT TGTGTGTTAG CACATCCATG
2151  TTGGGATTTG GTCTGTTGCT ATGTATTGTA ATGCTAAATT CTCTACCCAA
2201  AGTTCTAGGC CTACGAGTGA ATTCTCATGT TTACAAACTT GCTGTGTAAA
2251  CCTTGTTCCT TAATTTAATA CCATTGGTTA AATAAAATTG GCTGCAACCA
2301  ATTACTGGAG GGATTAGAGG TAGGGGCTT TTGAGTTACC TGTTTGGAGA
2351  TGGAGAAGGA GAGAGGAGAG ACCAAGAGGA GAAGGAGGAA GGAGAGGAGA
2401  GGAGAGGAGA GGAGAGGAGA GGAGAGGAGA GGAGAGGAGA GGAGAGGAGA
2451  GGCTGCCGTG AGGGAGAGG GACCATGAGC CTGTGGCCAG GAGAAACAGC
2501  AAGTATCTGG GGTACACTGG TGAGGAGGTG GCCAGGCCAG CAGTTAGAAG
2551  AGTAGATTAG GGGTGACCTC CAGTATTTGT CAAAGCCAAT TAAAATAACA
2601  AAAAAAAAAA AAAAGCGGCC GCTCTAGA
```

FIG.2A

```
  1  MPRGPVAALL LLILHGAWSC LDLTCYTDYL WTITCVLETR SPNPSILSLT
 51  WQDEYEELQD QETFCSLHRS GHNTTHIWYT CHMRLSQFLS DEVFIVNVTD
101  QSGNNSQECG SFVLAESIKP APPLNVTVAF SGRYDISWDS AYDEPSNYVL
151  RGKLQYELQY RNLRDPYAVR PVTKLISVDS RNVSLLPEEF HKDSSYQLQV
201  RAAPQPGTSF RGTWSEWSDP VIFQTQAGEP EAGWDPHMLL LLAVLIIVLV
251  FMGLKIHLPW RLWKKIWAPV PTPESFFQPL YREHSGNFKK WVNTPFTASS
301  IELVPQSSTT TSALHLSLYP AKEKKFPGLP GLEEQLECDG MSEPGHWCII
351  PLAAGQAVSA YSEERDRPYG LVSIDTVTVG DAEGLCVWPC SCEDDGYPAM
401  NLDAGRESGP NSEDLLLVTD PAFLSCGCVS GSGLRLGGSP GSLLDRLRLS
451  FAKEGDWTAD PTWRTGSPGG GSESEAGSPP GLDMDTFDSG FAGSDCGSPV
501  ETDEGPPRSY LRQWVVRTPP PVDSGAQSS
```

FIG. 3A

```
huMU-1     ................NNGTCGACTGGAGGCCCAGCTGCCCGTCATCA  32
                          ::||   |      ||||||  ||||||| |
murMU-1    CAGCCCTACTGTCTTCCTCTGTGTAGGCTCTGCCCAGATGCCCGGC....  196 huMU-1     GAGTCACACGTCTTATGACAGCCTGATTGGTGACTCGGGCTGGGTGTGGA  82
             ||    | || | |||   || |    |||||||    |||   | ||||
murMU-1    TGGTCCTCAGCCTCAGGACTATCTCAGCAGTGACTC.CCCTGATTCTGGA  245 huMU-1     TTCTCACCCCAGGCCTCTGCCTGCTTTTCTCAGACCCTCATCT...GTCAC  129
             |  ||||  |      || |   |    | |'|||  ||| ||| ||       |||
murMU-1    CTTGCACCTGACTGAACTCCTGCCCACCTCAAACCTTCACCTCCCACCAC  295 huMU-1     CCCCACGCTGAACCCAGCTG......CCACCCCCAGAAGCCCATCAGACT  173
             | |||| | ||   || ||||       |||| ||||| || ||| |   | |
murMU-1    CACCACTCCGAGTCCCGCTGTGACTCCCACGCCCAGGAGACCACCCAAGT  345 huMU-1     GCCCCCAGCACACGGAATGGATTTCTGAGAAAGAAGCCCGAAACAGAAGC  223
            | |||||||   |   |||||||  |||||||||||||||||   |  |||  .|| |||
murMU-1    G.CCCCAGCCTAAAGAATGGCTTTCTGAGAAAGACCCTGAAGGAGTAGGT  394 huMU-1     CCGTGGCAGTCAGCATGCCGCGTGGCTGGGCCGCCCCCTTGCTCCTGCTG  273
           |   |||||   |||||||||  || |||     |  ||  ||||   |||||||||
murMU-1    C..TGGGACACAGCATGCCCCGGGGCCCAGTGGCTGCCTTACTCCTGCTG  442 huMU-1     CTGCTCCAGGGAGGCTGGGGCTGCCCCGACCTCGTCTGCTACACCGATTA  323
            |  |||||  ||||   |||  |||||||    ||||||      ||||||||   ||  ||
murMU-1    ATTCTCCATGGAGCTTGGAGCTGCCTGGACCTCACTTGCTACACTGACTA  492 huMU-1     CCTCCAGACGGTCATCTGCATCCTGGAAATGTGGAACCTCCACCCCAGCA  373
           ||||   |||   ||| |||    ||||||||  |    |||  ||| |  ||||||||| |
murMU-1    CCTCTGGACCATCACCTGTGTCCTGGAGACACGGAGCCGCAACCCCAGCA  542 huMU-1     CGCTCACCCTTACCTGGCAAGACCAGTATCAACACCTGAAGGACGAGGCC  423
            ||||    ||   |||||||||||||  |   ||||||  ||  ||       |||||  |   |
murMU-1    TACTCAGTCTCACCTGGCAAGATGAATATGAGGAACTTCAGGACCAAGAG  592 huMU-1     ACCTCCTGCAGCCTCCACAGGTCGGCCCACAATGCCACGCATGCCACCTA  473
            ||||  |||||||||    |||||||||  |  ||||||     ||||  |||                    ||
murMU-1    ACCTTCTGCAGCCTACACAGGTCTGGCCACAACACCACACATATATGGTA  642 huMU-1     CACCTGCCACATGGATGTATTCCACTTCATGGCCGACGACATTTTCAGTG  523
           ||| |||||   |||   |  |  || |||  ||  ||||   || ||||| ||   ||||||  ||
murMU-1    CACGTGCCATATGCGCTTGTCTCAATTCCTGTCCGATGAAGTTTTCATTG  692 huMU-1     TCAACATCACAGACCAGTCTGGCAACTACTCCCAGGAGTGTGGCAGCTTT  573
           ||||    |  ||  ||||||||||||||||| |||||||  |||||||||||||||:||||||||
murMU-1    TCAATGTGACGGACCAGTCTGGCAACAACTCCCAAGAGTGTGGCAGCTTT  742 huMU-1     CTCCTGGCTGAGAGCATCAAGCCGGCTCCCCCTTTCAACGTGACTGTGAC  623
           |||||||||||||||||||||  ||  |||||||||||  ||  ||||||||||||||||||  |
murMU-1    GTCCTGGCTGAGAGCATCAAACCAGCTCCCCCCTTGAACGTGACTGTGGC  792 huMU-1     CTTCTCAGGACAGTATAATATCTCCTGGCGCTCAGATTACGAAGACCCTG  673
           ||||||||||   ||| |||||||||||     ||||| |||  || || ||
murMU-1    CTTCTCAGGACGCTATGATATCTCCTGGGACTCAGCTTATGACGAACCCT  842 huMU-1     CCTTCTACATGCTGAAGGGCAAGCTTCAGTATGAGCTGCAGTACAGGAAC  723
           ||   ||||  ||||||  |||||||||||  || ||||||||||||||||||||||   |||||
murMU-1    CCAACTACGTGCTGAGGGGCAAGCTACAATATGAGCTGCAGTATCGGAAC  892 huMU-1     CGGGGAGACCCCTGGGCTGTGAGTCCGAGGAGAAAGCTGATCTCAGTGGA  773
           |   |||||||||  ||||||||| |||   ||   ||||||||||||||||||||||||
murMU-1    CTCAGAGACCCCTATGCTGTGAGGCCGGTGACCAAGCTGATCTCAGTGGA  942 huMU-1     CTCAAGAAGTGTCTCCCTCCTCCCCCCTGGAGTTCCGCAAAGACTCGAGCT  823
```

FIG. 3B

```
                  11111111  11111  11 11111     1111111 111111 11 1111
muMU-1    CTCAAGAAACGTCTCTCTTCTCCCTGAAGAGTTCCACAAAGATTCTAGCT  992 huMU-1    ATGAGCTGCAGGTGCGGGCAGGGCCCATGCCTGGCTCCTCCTACCAGGGG  873
          I 11111111111111111  111   111 111 1 11 1 1   1111
muMU-1    ACCAGCTGCAGGTGCGGGCAGCGCCTCAGCCAGGCACTTCATTCAGGGGG  1042 huMU-1    ACCTGGAGTGAATGGAGTGACCCCGGTCATCTTTCAGACCCAGTCAGAGGA  923
          1111111111  11111111111  11111111111111111  1 1 111
muMU-1    ACCTGGAGTGAGTGGAGTGACCCCGTCATCTTTCAGACCCAGGCTGGGGA  1092 huMU-1    GTTAAAGGAAGGCTGGAACCCTCACCTGCTGCTTCTCCTCCTGCTTGTCA  973
          I   111 1111111 11111111  11111  11 111111  1111
muMU-1    GCCCGAGGCAGCCTGGGACCCTCACATGCTG...CTGCTCCTGGCTGTCT  1139 huMU-1    TAGTCTTCATTCCTGCCTTCTGGAGCCTGAAGACCCATCCATTGTGGAGG  1023
          I  11 1  1 1  1  111  1 1 11111111 111 1    111111
muMU-1    TGATCATTGTCCTGGTTTTCATGGGTCTGAAGATCCACCTGCCTTGGAGG  1189 huMU-1    CTATGGAAGAAGATATGGG...CCGTCCCCAGCCCTGACCGGTTCTTCAT  1070
          11111111 11111111111   1 11 1111 1111111 1 111111
muMU-1    CTATGGAAAAGATATGGGCACCAGTGCCCACCCCTGAGAGTTTCTTCCA  1239 huMU-1    GCCCCTGTACAAGGGCTGCAGCGGACACTTCAAGAAATGGGTGGGTGCAC  1120
          1111111111  11   111111  1111111111111111   1 1 1
muMU-1    GCCCCTGTACAGGGAGCACAGCGGGAACTTCAAGAAATGCGTTAATACCC  1289 huMU-1    CCTTCACTGGCTCCAGCCTGGAGCTGGGACCCTGGAGCCCAGAGGTGCCC  1170
          I 11111 1 1111111 1 111 111  11   111  1          1
muMU-1    CTTTCACGGCCTCCAGCATAGAGTTGGTGCCACAGAGTTCCACAACAACA  1339 huMU-1    TCCACCCTGGAGGTGTACAGCTGCCACCCACCACGGAGCCCGGCCAAGAG  1220
          11  11 1  1  111             H  1  11 111111
muMU-1    TCAGCCTTACATCTGT...............CATTGTATCCAGCCAAGGA  1374 huMU-1    GCTGCAGCTCACGGAGCTACAAGAACCAGCAGAGCTGGTGGAGTCTGACG  1270
          I  1 11 11 111 111 1   1  1 1 11111   111111 111 1
muMU-1    GAAGAAGTTCCCGGGGCTCCCCGGTCTGGAAGAGCAACTGCACTGTGATG  1424 huMU-1    GTGTGCCCAAGCCCAGCTTCTCG.........CCGACAGCCCAGAACTCG  1311
          I  11 1  1111  1    1111        11   11          1
muMU-1    GAATGTCTGAGCCTGGTCACTGGTGCCATAATCCCCTTGGCAGCTGGCCAA  1474 huMU-1    GGGGGCTCAGCTTACAGTGAGGAGAGGGATCGGCCATACGACCTGCTGTC  1361
          I 11 1111111 1111111111111111 11 11111111 11 11111111
muMU-1    GCGGTCTCAGCCTACAGTGAGGAGAGAGACCGGCCATATGGTCTGGTGTC  1524 huMU-1    CATTGACACAGTGACTGTGCTAGATGCAGAGGGGCCATGCACCTGGCCCT  1411
          111111111111111111 111111111111 1 11 11111111
muMU-1    CATTGACACAGTGACTGTGGGAGATGCAGAGGGCCTGTGTGTCTGGCCCT  1574 huMU-1    GCAGCTGTGAGGATGACGGCTACCCAGCCCTGGACCTGCATGCTGGCCTG  1461
          I 111111111111111 11111 111111 11 11111111111111111
muMU-1    GTAGCTGTGAGGATGATGGCTATCCAGCCATGAACCTGGATGCTGGCCGA  1624 huMU-1    GAGCCCAGCCCAGGCCTACAGGGACCCACTCTTGCATGCAGGGACCACAGT  1511
          111 1   1111    111111 1  1111111   11    1 1   1
muMU-1    GAGTCTGGCCCTAATTCAGAGGATCTGCTCTTCGTCACAGACCCTGCTTT  1674 huMU-1    CCTGTCCTGTGGCTGTGTCTCAGCTGGCAGCCCTGGGCTAGGAGGGCCCC  1561
          11111 11 111111111111111 1 1  1 1   1111 11111  111
muMU-1    TCTGTCTTGCGGCTGTGTCTCAGGTAGTGGTCTCAGGCTTGGAGGGCTCCC  1724 huMU-1    TGGGAAGCCTCCTGGACAGACTAAAGCCACCCCTTGCAGATGGGGAGGAC  1611
          11 111111 111111111  1 1 11   1  11111 1 1  1 1111
muMU-1    CAGGCAGCCTACTGGACAGGTTGAGGCTGTCATTTGCAAAGGAAGGGCAC  1774 huMU-1    TGGGCTGGGGGACTGCCCTGGGGTGGCCGGTCACCTGGAGGGGTCTCACA  1661
```

FIG. 3C

```
             III  I I    I  I     IIIII  I         IIII  II  IIIIIII  III  II
murMU-1      TGGACAGCAGACCCAACCTGGAGAACTGGGTCCCCAGGAGGGGGCTCTGA 1824 huMU-1       GAGTGAGGCGGGCTCACCCCTGGCCGGCCTGGATATGGACACGTTTGACA 1711
             IIIIIII  II  II  II  IIII    I  II  IIIII  IIIIIIII  IIIIIII
murMU-1      GAGTGAAGCAGGTTCCCCCC...CTGGTCTGGACATGGACACATTTGACA 1871 huMU-1       GTGGCTTTGTGGGCTCTGACTGCAGCAGCCCTGTGGAGTGTGACTTCACC 1761
             IIIIIIIII  II  II  IIIII   IIIIIIII  IIIIIII   I
murMU-1      GTGGCTTTGCAGGTTCAGACTGTGGCAGCCCCGTGGAGACT......... 1912 huMU-1       AGCCCCCGGGACGAAGGACCCCCCCGGAGCTACCTCCGCCAGTGGGTGGT 1811
                      II  IIIIIIIIIIII  II  IIIIII  IIIIIIIIIIIIIIIIII
murMU-1      .........GATGAAGGACCCCCTCGAAGCTATCTCCGCCAGTGGGTGGT 1953 huMU-1       CATTCCTCCGCCACTTTCGAGCCCTGGACCCCAGGCCAGCTAATGAGGCT 1861
             II   I  II  IIII  I    I   I    IIII  IIIII    IIIIII
murMU-1      CAGGACCCCTCCACCTGTGGACAGTGGAGCCCAGAGCAGCTA........ 1995 huMU-1       GACTGGATGTCCAGAGCTGGCCAGGCCACTGGGCCCTGAGCCAGAGACAA 1911
               I     I    IIII       II I I IIIIII
murMU-1      .GCATATAATAACCAGCTATAGTGAGAAGAGGCCTCTGAGCC........ 2036 huMU-1       TGGGCCTTTGAGCCTGATGTTTACAGTGTCTGTGTGTGTGTGCATATG 2011
             III    II  II  III     I    I  II  IIIIIIIIIIIIIII    I  II
murMU-1      TGGCATTTACAGTGTGAACATGTAGGGGTGTGTGTGTGTGTGTGTGTG 2086 huMU-1       TGTGTGTGTGCATATGCATGTGTGTGTGTGTGTGTGTCTTACTGGACTCA 2061
             IIIIIIIIII   I  II    IIIIIIIIIIIIIIIIIIIIIII     I    I
murMU-1      TGTGTGTGTGTGTGTGTGTGTGTGTGTGTGTGTGTGTCTT.GGGTTGTGT 2135 huMU-1       CGGAGCTCACCCATGTGCACAAGTGTGCACAGTAAACGTGTTTGTGGTCA 2111
                III  II  IIIIII     I    II              II  III  I   I
murMU-1      GTTAGCACATCCATGTTGGGATTTG...............GTCTGTTGCTA 2171 huMU-1       ACAGATGACAACAGCCGTCCTCCCTCCTAGGGTCTTGTGTTGCAAGTTGG 2161
                  II  I      I III    II I I  III  I    I  I III
murMU-1      TGTATTGTAATGCTAAATTCTCTACCCAAAGTTCTAGGCCTACGAGTGAA 2221 huMU-1       TCCACAGCATCTCCGGGGCTTTGTGGGATCAGGGCATTGCCTGTGACTGA 2211
             I  I  II    I  I        IIII    I  I   I    I III      I I
murMU-1      TTCTCATGTTTACAAACTTGCTGTGTAAACCTTG...TTCCTTAATTTAA 2268 huMU-1       GGCGGAGCCCAGCCCTCCAGCGTCTGCCTCCAGGAGCTGCAAGAAGTCCA 2261
                I                I  I IIII    III       III  I I I I    I
murMU-1      TACCATTGGTTAAATAAAATTGGCTGCAACCAATTACTGCAGCCATTAGA 2318 huMU-1       TATTG.....TTCCTTATCACCTGCCAACAGGAAGCGAAAGGGGATGGAG 2306
             I I         II   -   I IIIII   II   I  III I I      IIII
murMU-1      GGTAGGGGCTTTTGAGTTACCTGTTTGCAGATGGAGAAGGAGAGAGGAG 2368 huMU-1       TGAGCCCATGGTGACCTCGGGAATGGCAATTTTTTGGGCGGCCCCTGGAC 2356
             II I      II II       III  I           I I  I       IIII
murMU-1      AGACCAAGAGGAGAAGGAGGAAGGAGAGGAGAGGAGAGGAGAGGAGAGGA 2418 huMU-1       GAAGGTCTGAATCCCGACTCTGATACCTTCTGGCTGTGCTACCTGAGCCA 2406
             II I    II      II    II       I      III      I I
murMU-1      GAGGAGAGGAGAGGAGA.GGAGAGGAGAGGAGAGGCTGCCGTGAGGGGAG 2467 huMU-1       AGTCGCCTCCCCTCTCTGGGCTAGAGTTTCCTTATCCAGACAGTGGGGAA 2456
             II    II       II III I  III      I  I                   I I
murMU-1      AGGGACCATGAGCCTGTGGCCAGGAGAAACAGCA............AGTA 2505 huMU-1       GGCATGACACACCTGGGGAAATTGGCGATGTCACCCGTGTACGGTACGC 2506
              I   IIII   I  I  I   IIII  I  I  II   I      II   I      I
murMU-1      TCTGGGGTACACTCGTGAGGAGGTGGCCAGGCCAGC..AGTTAGAAGAGT 2553 huMU-1       ACCCCAGAGCAGACCCTCAATAAACGTCAGCTTCCTTCAAAAAAAAAAAA 2556
```

FIG. 3D

```
          ||   || |  ||||  || ||   ||||     |. | |||| || ||||
murMU-1   AGATTAGGGGTGACCTCCAGTATTTGTCAAAGCCAATTAAAATAACAAAA 2603 huMU-1    AAAAATCTAGA............... 2567
          |||||    | |
murMU-1   AAAAAAAAAAAGCGGCCGCTCTAGA 2628
```

FIG.4

```
Human MU-1    MPRGWAAPLLLLLLQGGWGCPDLVCYTDYLQTVICILEMWNLHPSTLTLT  50
              ||||  | ||||:| | | | || ||||||  |: |:||  _ _|| |_||
MurineMU-1    MPRGPVAALLLLILHGAWSCLDLTCYTDYLWTITCVLETRSPNPSILSLT  50

Human MU-1    WQDQYEELKDEATSCSLHRSAHNATHATYTCHMDVFHFMADDIFSVNITD 100
              |||:||||_|: | ||||||| || ||  |||||  _  |:_|::| ||:||
MurineMU-1    WQDEYEELQDQETFCSLHRSGHNTTHIWYTCHMRLSQFLSDEVFIVNVTD 100

Human MU-1    QSGNYSQECGSFLLAESIKPAPPFNVTVTFSGQYNISWRSDYEDPAFYML 150
              ||||  |||||||| _|||||||||||  ||||  |||_|_|_||| |  |::|_  |_|
MurineMU-1    QSGNNSQECGSFVLAESIKPAPPLNVTVAFSGRYDISWDSAYDEPSNYVL 150

Human MU-1    KGKLQYELQYRNRGDPWAVSPRRKLISVDSRSVSLLPLEFRKDSSYELQV 200
              :|||||||||||  ||:|| |  |||||||||_|||||  ||  |||||:|||
MurineMU-1    RGKLQYELQYRNLRDPYAVRPVTKLISVDSRNVSLLPEEFHKDSSYQLQV 200

Human MU-1    RAGPMPGSSYQGTWSEWSDPVIFQTQSEELKEGWNPHLLLLLLLVIVFIP 250
              ||  |  ||_|:_|||||||||||||||||_ |  _ ||_||:||||  __|:  :
MurineMU-1    RAAPQPGTSFRGTWSEWSDPVIFQTQAGEPEAGWDPHMLLLLAVLIIVL_ 249

Human MU-1    AFWSLKTHPLWRLWKKIWA_VPSPERFFMPLYKGCSGDFKKWVGAPFTGS 299
              |  || | ||||||||| ||_||  ||:  ||_|| || |||:  ||| |
MurineMU-1    VFMGLKIHLPWRLWKKIWAPVPTPESFFQPLYREHSGNFKKWVNTPFTAS 299

Human MU-1    SLELGPWSPEVPSTLEVYSCHPPRSPAKRLQLTELQEPAELVESDGVPKP 349
              |:|| | |  | |   | |||   |  | _|||| _ | |_|||_ _|
MurineMU-1    SIELVPQSSTTTSAL_____HLSLYPAKEKKFPGLPGLEEQLECDGMSEP 344

Human MU-1    SFW___PTAQNSGGSAYSEERDRPYGLVSIDTVTVLDAEGPCTWPCSCED 396
              |   | |   ||||||||||||||||||||||| |||| | |||||||
MurineMU-1    GHWCIIPLAAGQAVSAYSEERDRPYGLVSIDTVTVGDAEGLCVWPCSCED 394

Human MU-1    DGYPALDLDAGLEPSPGLEDPLLDAGTTVLSCGCVSAGSPGLGGPLGSLL 446
              |||||:_|||| |  | || || |||||||    |||    ||||
MurineMU-1    DGYPAMNLDAGRESGPNSEDLLLVTDPAFLSCGCVSGSGLRLGGSPGSLL 444

Human MU-1    DRLKPPLADGEDWAGGLPWGGRSPGGVSESEAGSPLAGLDMDTFDSGFVG 496
              |||:  |  ||    |  |||| |||||||||  |||||||||||| |
MurineMU-1    DRLRLSFAKEGDWTADPTWRTGSPGGGSESEAGSP_PGLDMDTFDSGFAG 493

Human MU-1    SDCSSPVECDFTSPGDEGPPRSYLRQWVV_IPPPLSSPGPQAS*        539
              ||| ||||       |||||||||||||| |||_ | | |_|
MurineMU-1    SDCGSPVET_____DEGPPRSYLRQWVVRTPPPVDS_GAQSS_        529
```

FIG. 5

```
              1                                                     50
humu     ---MPRGWAA PLLLLL..LQ GGWG......         CPDLVCYTDY LQTVICILEM
mousemu  ---MPRGPVA ALLLLI..LH GAWG......         CLDLTCYTDY LWTITCVLET
humil2rbc MAAPALSWRL PLLILLLPLA TSWASAAVNG        TSQFTCFYNS RANISCVWSQ
              51                                                    100
humu     WN..LHPSTL TLTWQDQYEE LKDEATSCSL HRSAHNATHA TYTCHM....
mousemu  RS..PNPSIL SLTWQDEYEE LQDQETFCSL HRSGHNTTHI WYTCHM....
humil2rbc DGALQDTSCQ VHAWPDR... .RRWNQTCEL ....LPVSQA SWACNLILGA
              101                                                   150
humu     .DVFHFMADD IFSVNITDQS GN..YSQECG SFLLAESIKP APPFNVTVTF
mousemu  .RLSQFLSDE VFIVNVTDQS GN..NSQECG SFVLAESIKP APPLNVTVAF
humil2rbc PDSQKLTTVD IVTLRVLCRE GVRWRVMAIQ DFKPFENLRL MAPISLQVVH
              151                                                   200
humu     ..SGQYNISW RSDYEDPAFY MLKGKLQYEL QYRNRGDPWA VSPRRKLISV
mousemu  ..SGRYDISW DSAYDEPSNY VLRGKLQYEL QYRNLRDPYA VRPVTKLISV
humil2rbc VETHRCNISW E..ISQASHY FER.HLEFEA RTLSPGHTWE EAP...LLTL
              201                                                   250
humu     DSRSVSLLPL EFRKDSSYEL QVRAGPMPGS SYQGTWSEWS DPVIFQTQS.
mousemu  DSRNVSLLPE EFHKDSSYQL QVRAAPQPGT SFRGTWSEWS DPVIFQTQA.
humil2rbc KQKQEWICLE TLTPDTQYEF QVRVKPLQGE F..TTWSPWS QPLAFRTKPA
              251                                                   300
humu     ..EELKEGWN PHLLLLL... LLVIVFIPAF WSLKTHPLWR LWKKIWA.VP
mousemu  ..GEPEAGWD PHMLLLL... AVLIIVL.VF MGLKIHLPWR LWKKIWAPVP
humil2rbc ALGKDTIPWL GHLLVGLSGA FGFIILVYLL INCRNTGPW. LKKVLKCNTP
              301                                                   350
humu     SPERFFMPLY KGCSGDFKKW VGAPFTGSSL ELGPWSPEVP STLEVYSCHP
mousemu  TPESFFQPLY REHSGNFKKW VNTPFTASSI ELVPQSSTTT SAL....HL
humil2rbc DPSKFFSQLS SEHGGDVQKW LSSPFPSSSF SPGGLAPEIS PLEVLERDKV
              351                                                   400
humu     PRSPAKRLQL TELQEPA..E LVESDGVPKP SFW...PTAQ NSGGSAYSEE
mousemu  SLYPAKEKKF PGLPGLE..E QLECDGMSEP GHWCIIPLAA GQAVSAYSEE
humil2rbc TQLLLQQDKV PEPASLSSNH SLTSCFTNQG YFFFHLPDAL EIEACQVYFT
              401                                                   450
humu     RDRPYGLVSI DTVTVLDAEG PC...TWPCS CEDDGYPALD LDAGLEPSPG
mousemu  RDRPYGLVSI DTVTVGDAEG LC...VWPCS CEDDGYPAMN LDAGRESGPN
humil2rbc YD.PYSEEDP DEGVAGAPTG SSPQPLQPLS GEDDAYCTF. .........PS
              451                                                   500
humu     LEDPLLDAGT TVLSCGCVSA GSPGLGGPLG SLLDRLKPPL AD..GEDWAG
mousemu  SEDLLLVTDP AFLSCGCVSG SGLRLGGSPG SLLDRLRLSF AK..EGDWTA
humil2rbc RDDLLLFS.P SLL..GGPSP PSTAPGGS.G AGEERMPPSL QERVPRDWDP
              501                                                   550
humu     GLPWGGRSPG GVSESEAGSP LAGLDMDTFD SGFVGSDCSS PVECDFTSPG
mousemu  DPTWRTGSPG GGSESEAGSP .PGLDMDTFD SGFAGSDCGS PVET......
humil2rbc Q.PLGPPTPG VPDLVDFQPP P...ELVLRE AGEEVPDAG. PRE.GVSFPW
              551                                       588
humu     DEGPPRSYLR QWVVIPPPLS SPGPQAS*-- --------
mousemu  DEGPPRSYLR QWVVRTPPPV DSGAQSS--- --------
humil2rbc SRPPGQGEFR ALNARLPLNT DAYLSLQELQ GQDPTHLV
```

Signaling through MU-1

```
atg aaa ttc tta gtc aac gtt gcc ctt gtt ttt atg gtc gtg tac att  48
Met Lys Phe Leu Val Asn Val Ala Leu Val Phe Met Val Val Tyr Ile
1               5                   10                  15 tct tac atc tat gcc ggc agc gga cac cac cat cat cac cac ggt agc  96
Ser Tyr Ile Tyr Ala Gly Ser Gly His His His His His His Gly Ser
            20                  25                  30 ggc gac tat aaa gac gat gac gat aag ggt tcc gga tgc ccc gac ctc  144
Gly Asp Tyr Lys Asp Asp Asp Asp Lys Gly Ser Gly Cys Pro Asp Leu
                35                  40                  45 gtc tgc tac acc gat tac ctc cag acg gtc atc tgc atc ctg gaa atg  192
Val Cys Tyr Thr Asp Tyr Leu Gln Thr Val Ile Cys Ile Leu Glu Met
50                  55                  60 tgg aac ctc cac ccc agc acg ctc acc ctt acc tgg caa gac cag tat  240
Trp Asn Leu His Pro Ser Thr Leu Thr Leu Thr Trp Gln Asp Gln Tyr
65                  70                  75                  80 gaa gag ctg aag gac gag gcc acc tcc tgc agc ctc cac agg tcg gcc  288
Glu Glu Leu Lys Asp Glu Ala Thr Ser Cys Ser Leu His Arg Ser Ala
                85                  90                  95 cac aat gcc acg cat gcc acc tac acc tgc cac atg gat gta ttc cac  336
His Asn Ala Thr His Ala Thr Tyr Thr Cys His Met Asp Val Phe His
            100                 105                 110 ttc atg gcc gac gac att ttc agt gtc aac atc aca gac cag tct ggc  384
Phe Met Ala Asp Asp Ile Phe Ser Val Asn Ile Thr Asp Gln Ser Gly
            115                 120                 125 aac tac tcc cag gag tgt ggc agc ttt ctc ctg gct gag agc atc aag  432
Asn Tyr Ser Gln Glu Cys Gly Ser Phe Leu Leu Ala Glu Ser Ile Lys
130                 135                 140 ccg gct ccc cct ttc aac gtg act gtg acc ttc tca gga cag tat aat  480
Pro Ala Pro Pro Phe Asn Val Thr Val Thr Phe Ser Gly Gln Tyr Asn
145                 150                 155                 160 atc tcc tgg cgc tca gat tac gaa gac cct gcc ttc tac atg ctg aag  528
Ile Ser Trp Arg Ser Asp Tyr Glu Asp Pro Ala Phe Tyr Met Leu Lys
                165                 170                 175 ggc aag ctt cag tat gag ctg cag tac agg aac cgg gga gac ccc tgg  576
Gly Lys Leu Gln Tyr Glu Leu Gln Tyr Arg Asn Arg Gly Asp Pro Trp
                180                 185                 190 gct gtg agt ccg agg aga aag ctg atc tca gtg gac tca aga agt gtc  624
Ala Val Ser Pro Arg Arg Lys Leu Ile Ser Val Asp Ser Arg Ser Val
            195                 200                 205 tcc ctc ctc ccc ctg gag ttc cgc aaa gac tcg agc tat gag ctg cag  672
Ser Leu Leu Pro Leu Glu Phe Arg Lys Asp Ser Ser Tyr Glu Leu Gln
210                 215                 220 gtg cgg gca ggg ccc atg cct ggc tcc tcc tac cag ggg acc tgg agt  720
```

Figure 7A

```
Val Arg Ala Gly Pro Met Pro Gly Ser Ser Tyr Gln Gly Thr Trp Ser
225             230             235             240 gaa tgg agt gac ccg gtc atc ttt cag acc cag tca gag gag tta aag    768
Glu Trp Ser Asp Pro Val Ile Phe Gln Thr Gln Ser Glu Glu Leu Lys
                245             250             255 gaa ggc tgg aac taa tga   SEQ ID NO: 22                            786
Glu Gly Trp Asn  SEQ ID NO: 23
        260
```

Figure 7B

| | | | | | | | | | | | | | | |
|---|---|---|---|---|---|---|---|---|---|---|---|---|---|---|
| gcggccgcac | cacc | atg<br>Met<br>1 | ccg<br>Pro | cgt<br>Arg | ggc<br>Gly | tgg<br>Trp<br>5 | gcc<br>Ala | gcc<br>Ala | ccc<br>Pro | ttg<br>Leu | ctc<br>Leu<br>10 | ctg<br>Leu | ctg<br>Leu | 50 |
| ctg<br>Leu | ctc<br>Leu | cag<br>Gln<br>15 | gga<br>Gly | ggc<br>Gly | tgg<br>Trp | ggc<br>Gly | tgc<br>Cys<br>20 | ccc<br>Pro | gac<br>Asp | ctc<br>Leu | gtc<br>Val | tgc<br>Cys<br>25 | tac<br>Tyr | acc<br>Thr | gat<br>Asp | 98 |
| tac<br>Tyr | ctc<br>Leu<br>30 | cag<br>Gln | acg<br>Thr | gtc<br>Val | atc<br>Ile | tgc<br>Cys<br>35 | atc<br>Ile | ctg<br>Leu | gaa<br>Glu | atg<br>Met | tgg<br>Trp<br>40 | aac<br>Asn | ctc<br>Leu | cac<br>His | ccc<br>Pro | 146 |
| agc<br>Ser<br>45 | acg<br>Thr | ctc<br>Leu | acc<br>Thr | ctt<br>Leu | acc<br>Thr<br>50 | tgg<br>Trp | caa<br>Gln | gac<br>Asp | cag<br>Gln | tat<br>Tyr<br>55 | gaa<br>Glu | gag<br>Glu | ctg<br>Leu | aag<br>Lys | gac<br>Asp<br>60 | 194 |
| gag<br>Glu | gcc<br>Ala | acc<br>Thr | tcc<br>Ser | agc<br>Ser<br>65 | ctc<br>Leu | cac<br>His | agg<br>Arg | tcg<br>Ser | gcc<br>Ala<br>70 | cac<br>His | aat<br>Asn | gcc<br>Ala | acg<br>Thr | cat<br>His<br>75 | 242 |
| gcc<br>Ala | acc<br>Thr | tac<br>Tyr | acc<br>Thr<br>80 | tgc<br>Cys | cac<br>His | atg<br>Met | gat<br>Asp | gta<br>Val<br>85 | ttc<br>Phe | cac<br>His | ttc<br>Phe | atg<br>Met | gcc<br>Ala<br>90 | gac<br>Asp | gac<br>Asp | 290 |
| att<br>Ile | ttc<br>Phe | agt<br>Ser<br>95 | gtc<br>Val | aac<br>Asn | atc<br>Ile | aca<br>Thr | gac<br>Asp<br>100 | cag<br>Gln | tct<br>Ser | ggc<br>Gly | aac<br>Asn | tac<br>Tyr<br>105 | tcc<br>Ser | cag<br>Gln | gag<br>Glu | 338 |
| tgt<br>Cys | ggc<br>Gly<br>110 | agc<br>Ser | ttt<br>Phe | ctc<br>Leu | ctg<br>Leu | gct<br>Ala<br>115 | gag<br>Glu | agc<br>Ser | atc<br>Ile | aag<br>Lys | ccg<br>Pro<br>120 | gct<br>Ala | ccc<br>Pro | cct<br>Pro | ttc<br>Phe | 386 |
| aac<br>Asn<br>125 | gtg<br>Val | act<br>Thr | gtg<br>Val | acc<br>Thr | ttc<br>Phe<br>130 | tca<br>Ser | gga<br>Gly | cag<br>Gln | tat<br>Tyr | aat<br>Asn<br>135 | atc<br>Ile | tcc<br>Ser | tgg<br>Trp | cgc<br>Arg | tca<br>Ser<br>140 | 434 |
| gat<br>Asp | tac<br>Tyr | gaa<br>Glu | gac<br>Asp | cct<br>Pro<br>145 | gcc<br>Ala | ttc<br>Phe | tac<br>Tyr | atg<br>Met | ctg<br>Leu<br>150 | aag<br>Lys | ggc<br>Gly | aag<br>Lys | ctt<br>Leu | cag<br>Gln<br>155 | tat<br>Tyr | 482 |
| gag<br>Glu | ctg<br>Leu | cag<br>Gln | tac<br>Tyr<br>160 | agg<br>Arg | aac<br>Asn | cgg<br>Arg | gga<br>Gly | gac<br>Asp<br>165 | ccc<br>Pro | tgg<br>Trp | gct<br>Ala | gtg<br>Val | agt<br>Ser<br>170 | ccg<br>Pro | agg<br>Arg | 530 |
| aga<br>Arg | aag<br>Lys | ctg<br>Leu<br>175 | atc<br>Ile | tca<br>Ser | gtg<br>Val | gac<br>Asp | tca<br>Ser<br>180 | aga<br>Arg | agt<br>Ser | gtc<br>Val | tcc<br>Ser | ctc<br>Leu<br>185 | ctc<br>Leu | ccc<br>Pro | ctg<br>Leu | 578 |
| gag<br>Glu | ttc<br>Phe<br>190 | cgc<br>Arg | aaa<br>Lys | gac<br>Asp | tcg<br>Ser | agc<br>Ser<br>195 | tat<br>Tyr | gag<br>Glu | ctg<br>Leu | cag<br>Gln | gtg<br>Val<br>200 | cgg<br>Arg | gca<br>Ala | ggg<br>Gly | ccc<br>Pro | 626 |
| atg<br>Met | cct<br>Pro | ggc<br>Gly<br>205 | tcc<br>Ser | tcc<br>Ser | tac<br>Tyr | cag<br>Gln<br>210 | ggg<br>Gly | acc<br>Thr | tgg<br>Trp | agt<br>Ser | gaa<br>Glu<br>215 | tgg<br>Trp | agt<br>Ser | gac<br>Asp | ccg<br>Pro<br>220 | 674 |

Figure 8A

```
gtc atc ttt cag acc cag tca gag gag tta aag gaa ggc tgg aac ggc      722
Val Ile Phe Gln Thr Gln Ser Glu Glu Leu Lys Glu Gly Trp Asn Gly
            225                 230                 235 tcc ggc tct aga gac aaa act cac aca tgc ccg tgc cca gca cct          770
Ser Gly Ser Arg Asp Lys Thr His Thr Cys Pro Pro Cys Pro Ala Pro
        240                 245                 250 gaa ctc ctg ggg gga ccg tca gtc ttc ctc ttc ccc cca aaa ccc aag      818
Glu Leu Leu Gly Gly Pro Ser Val Phe Leu Phe Pro Pro Lys Pro Lys
            255                 260                 265 gac acc ctc atg atc tcc cgg acc cct gag gtc aca tgc gtg gtg gtg      866
Asp Thr Leu Met Ile Ser Arg Thr Pro Glu Val Thr Cys Val Val Val
        270                 275                 280 gac gtg agc cac gaa gac cct gag gtc aag ttc aac tgg tac gtg gac      914
Asp Val Ser His Glu Asp Pro Glu Val Lys Phe Asn Trp Tyr Val Asp
285                 290                 295                 300 ggc gtg gag gtg cat aat gcc aag aca aag ccg cgg gag gag cag tac      962
Gly Val Glu Val His Asn Ala Lys Thr Lys Pro Arg Glu Glu Gln Tyr
                305                 310                 315 aac agc acg tac cgt gtg gtc agc gtc ctc acc gtc ctg cac cag gac     1010
Asn Ser Thr Tyr Arg Val Val Ser Val Leu Thr Val Leu His Gln Asp
            320                 325                 330 tgg ctg aat ggc aag gag tac aag tgc aag gtc tcc aac aaa gcc ctc     1058
Trp Leu Asn Gly Lys Glu Tyr Lys Cys Lys Val Ser Asn Lys Ala Leu
        335                 340                 345 cca gtc ccc atc gag aaa acc atc tcc aaa gcc aaa ggg cag ccc cga     1106
Pro Val Pro Ile Glu Lys Thr Ile Ser Lys Ala Lys Gly Gln Pro Arg
    350                 355                 360 gaa cca cag gtg tac acc ctg ccc cca tcc cgg gag gag atg acc aag     1154
Glu Pro Gln Val Tyr Thr Leu Pro Pro Ser Arg Glu Glu Met Thr Lys
365                 370                 375                 380 aac cag gtc agc ctg acc tgc ctg gtc aaa ggc ttc tat ccc agc gac     1202
Asn Gln Val Ser Leu Thr Cys Leu Val Lys Gly Phe Tyr Pro Ser Asp
            385                 390                 395 atc gcc gtg gag tgg gag agc aat ggg cag ccg gag aac aac tac aag     1250
Ile Ala Val Glu Trp Glu Ser Asn Gly Gln Pro Glu Asn Asn Tyr Lys
        400                 405                 410 acc acg cct ccc gtg ctg gac tcc gac ggc tcc ttc ttc ctc tat agc     1298
Thr Thr Pro Pro Val Leu Asp Ser Asp Gly Ser Phe Phe Leu Tyr Ser
    415                 420                 425 aag ctc acc gtg gac aag agc agg tgg cag cag ggg aac gtc ttc tca     1346
Lys Leu Thr Val Asp Lys Ser Arg Trp Gln Gln Gly Asn Val Phe Ser
430                 435                 440
```

Figure 8B

```
tgc tcc gtg atg cat gag gct ctg cac aac cac tac acg cag aag agc      1394
Cys Ser Val Met His Glu Ala Leu His Asn His Tyr Thr Gln Lys Ser
445                 450                 455                 460 ctc tcc ctg tcc ccg ggt aaa tgagtgaatt c SEQ ID NO: 24               1426
Leu Ser Leu Ser Pro Gly Lys SEQ ID NO: 25
                465
```

Figure 8C

```
gcggccgcac cacc atg ccg cgt ggc tgg gcc gcc ccc ttg ctc ctg ctg       50
              Met Pro Arg Gly Trp Ala Ala Pro Leu Leu Leu Leu
              1           5                   10 ctg ctc cag gga ggc tgg ggc tgc ccc gac ctc gtc tgc tac acc gat       98
Leu Leu Gln Gly Gly Trp Gly Cys Pro Asp Leu Val Cys Tyr Thr Asp
        15              20              25 tac ctc cag acg gtc atc tgc atc ctg gaa atg tgg aac ctc cac ccc      146
Tyr Leu Gln Thr Val Ile Cys Ile Leu Glu Met Trp Asn Leu His Pro
    30              35              40 agc acg ctc acc ctt acc tgg caa gac cag tat gaa gag ctg aag gac      194
Ser Thr Leu Thr Leu Thr Trp Gln Asp Gln Tyr Glu Glu Leu Lys Asp
45              50              55              60 gag gcc acc tcc tgc agc ctc cac agg tcg gcc cac aat gcc acg cat      242
Glu Ala Thr Ser Cys Ser Leu His Arg Ser Ala His Asn Ala Thr His
                65              70              75 gcc acc tac acc tgc cac atg gat gta ttc cac ttc atg gcc gac gac      290
Ala Thr Tyr Thr Cys His Met Asp Val Phe His Phe Met Ala Asp Asp
            80              85              90 att ttc agt gtc aac atc aca gac cag tct ggc aac tac tcc cag gag      338
Ile Phe Ser Val Asn Ile Thr Asp Gln Ser Gly Asn Tyr Ser Gln Glu
        95              100             105 tgt ggc agc ttt ctc ctg gct gag agc atc aag ccg gct ccc cct ttc      386
Cys Gly Ser Phe Leu Leu Ala Glu Ser Ile Lys Pro Ala Pro Pro Phe
    110             115                 120 aac gtg act gtg acc ttc tca gga cag tat aat atc tcc tgg cgc tca      434
Asn Val Thr Val Thr Phe Ser Gly Gln Tyr Asn Ile Ser Trp Arg Ser
125             130                 135             140 gat tac gaa gac cct gcc ttc tac atg ctg aag ggc aag ctt cag tat      482
Asp Tyr Glu Asp Pro Ala Phe Tyr Met Leu Lys Gly Lys Leu Gln Tyr
                145             150             155 gag ctg cag tac agg aac cgg gga gac ccc tgg gct gtg agt ccg agg      530
Glu Leu Gln Tyr Arg Asn Arg Gly Asp Pro Trp Ala Val Ser Pro Arg
            160             165             170 aga aag ctg atc tca gtg gac tca aga agt gtc tcc ctc ctc ccc ctg      578
Arg Lys Leu Ile Ser Val Asp Ser Arg Ser Val Ser Leu Leu Pro Leu
        175             180             185 gag ttc cgc aaa gac tcg agc tat gag ctg cag gtg cgg gca ggg ccc      626
Glu Phe Arg Lys Asp Ser Ser Tyr Glu Leu Gln Val Arg Ala Gly Pro
    190             195                 200 atg cct ggc tcc tcc tac cag ggg acc tgg agt gaa tgg agt gac ccg      674
Met Pro Gly Ser Ser Tyr Gln Gly Thr Trp Ser Glu Trp Ser Asp Pro
205             210                 215                 220
```

Figure 9A

```
gtc atc ttt cag acc cag tca gag gag tta aag gaa ggc tgg aac ggc    722
Val Ile Phe Gln Thr Gln Ser Glu Glu Leu Lys Glu Gly Trp Asn Gly
            225             230              235 tcc ggc tct aga gac aaa act cac aca tgc cca ccg tgc cca gca cct    770
Ser Gly Ser Arg Asp Lys Thr His Thr Cys Pro Pro Cys Pro Ala Pro
            240             245              250 gaa ctc ctg ggg gga ccg tca gtc ttc ctc ttc ccc cca aaa ccc aag    818
Glu Leu Leu Gly Gly Pro Ser Val Phe Leu Phe Pro Pro Lys Pro Lys
            255             260              265 gac acc ctc atg atc tcc cgg acc cct gag gtc aca tgc gtg gtg gtg    866
Asp Thr Leu Met Ile Ser Arg Thr Pro Glu Val Thr Cys Val Val Val
            270             275              280 gac gtg agc cac gaa gac cct gag gtc aag ttc aac tgg tac gtg gac    914
Asp Val Ser His Glu Asp Pro Glu Val Lys Phe Asn Trp Tyr Val Asp
285             290             295              300 ggc gtg gag gtg cat aat gcc aag aca aag ccg cgg gag gag cag tac    962
Gly Val Glu Val His Asn Ala Lys Thr Lys Pro Arg Glu Glu Gln Tyr
            305             310              315 aac agc acg tac cgt gtg gtc agc gtc ctc acc gtc ctg cac cag gac   1010
Asn Ser Thr Tyr Arg Val Val Ser Val Leu Thr Val Leu His Gln Asp
            320             325              330 tgg ctg aat ggc aag gag tac aag tgc aag gtc tcc aac aaa gcc ctc   1058
Trp Leu Asn Gly Lys Glu Tyr Lys Cys Lys Val Ser Asn Lys Ala Leu
            335             340              345 cca gtc ccc atc gag aaa acc atc tcc aaa gcc aaa ggg cag ccc cga   1106
Pro Val Pro Ile Glu Lys Thr Ile Ser Lys Ala Lys Gly Gln Pro Arg
350             355             360 gaa cca cag gtg tac acc ctg ccc cca tcc cgg gag gag atg acc aag   1154
Glu Pro Gln Val Tyr Thr Leu Pro Pro Ser Arg Glu Glu Met Thr Lys
365             370             375              380 aac cag gtc agc ctg acc tgc ctg gtc aaa ggc ttc tat ccc agc gac   1202
Asn Gln Val Ser Leu Thr Cys Leu Val Lys Gly Phe Tyr Pro Ser Asp
            385             390              395 atc gcc gtg gag tgg gag agc aat ggg cag ccg gag aac aac tac aag   1250
Ile Ala Val Glu Trp Glu Ser Asn Gly Gln Pro Glu Asn Asn Tyr Lys
            400             405              410 acc acg cct ccc gtg ctg gac tcc gac ggc tcc ttc ttc ctc tat agc   1298
Thr Thr Pro Pro Val Leu Asp Ser Asp Gly Ser Phe Phe Leu Tyr Ser
            415             420              425 aag ctc acc gtg gac aag agc agg tgg cag cag ggg aac gtc ttc tca   1346
Lys Leu Thr Val Asp Lys Ser Arg Trp Gln Gln Gly Asn Val Phe Ser
            430             435              440
```

Figure 9B

```
tgc tcc gtg atg cat gag gct ctg cac aac cac tac acg cag aag agc        1394
Cys Ser Val Met His Glu Ala Leu His Asn His Tyr Thr Gln Lys Ser
445                 450                 455                 460 ctc tcc ctg tcc ccg ggt aaa tca gga atg gca tca atg aca gga ggt        1442
Leu Ser Leu Ser Pro Gly Lys Ser Gly Met Ala Ser Met Thr Gly Gly
                465                 470                 475 caa caa atg ggt tct gga tct cat cat cat cat cat cat tct gga ggt        1490
Gln Gln Met Gly Ser Gly Ser His His His His His His Ser Gly Gly
                480                 485                 490 tgagaattc   SEQ ID NO:26
            SEQ ID NO:27                                               1499
```

Figure 9C

```
gcggccgcac cacc atg ccg cgt ggc tgg gcc gcc ccc ttg ctc ctg ctg      50
              Met Pro Arg Gly Trp Ala Ala Pro Leu Leu Leu Leu
               1           5                   10 ctg ctc cag gga ggc tgg ggc tgc ccc gac ctc gtc tgc tac acc gat      98
Leu Leu Gln Gly Gly Trp Gly Cys Pro Asp Leu Val Cys Tyr Thr Asp
            15              20              25 tac ctc cag acg gtc atc tgc atc ctg gaa atg tgg aac ctc cac ccc     146
Tyr Leu Gln Thr Val Ile Cys Ile Leu Glu Met Trp Asn Leu His Pro
    30              35              40 agc acg ctc acc ctt acc tgg caa gac cag tat gaa gag ctg aag gac     194
Ser Thr Leu Thr Leu Thr Trp Gln Asp Gln Tyr Glu Glu Leu Lys Asp
45              50              55              60 gag gcc acc tcc tgc agc ctc cac agg tcg gcc cac aat gcc acg cat     242
Glu Ala Thr Ser Cys Ser Leu His Arg Ser Ala His Asn Ala Thr His
                65              70              75 gcc acc tac acc tgc cac atg gat gta ttc cac ttc atg gcc gac gac     290
Ala Thr Tyr Thr Cys His Met Asp Val Phe His Phe Met Ala Asp Asp
            80              85              90 att ttc agt gtc aac atc aca gac cag tct ggc aac tac tcc cag gag     338
Ile Phe Ser Val Asn Ile Thr Asp Gln Ser Gly Asn Tyr Ser Gln Glu
            95              100             105 tgt ggc agc ttt ctc ctg gct gag agc atc aag ccg gct ccc cct ttc     386
Cys Gly Ser Phe Leu Leu Ala Glu Ser Ile Lys Pro Ala Pro Pro Phe
    110             115             120 aac gtg act gtg acc ttc tca gga cag tat aat atc tcc tgg cgc tca     434
Asn Val Thr Val Thr Phe Ser Gly Gln Tyr Asn Ile Ser Trp Arg Ser
125             130             135             140 gat tac gaa gac cct gcc ttc tac atg ctg aag ggc aag ctt cag tat     482
Asp Tyr Glu Asp Pro Ala Phe Tyr Met Leu Lys Gly Lys Leu Gln Tyr
                145             150             155 gag ctg cag tac agg aac cgg gga gac ccc tgg gct gtg agt ccg agg     530
Glu Leu Gln Tyr Arg Asn Arg Gly Asp Pro Trp Ala Val Ser Pro Arg
            160             165             170 aga aag ctg atc tca gtg gac tca aga agt gtc tcc ctc ctc ccc ctg     578
Arg Lys Leu Ile Ser Val Asp Ser Arg Ser Val Ser Leu Leu Pro Leu
        175             180             185 gag ttc cgc aaa gac tcg agc tat gag ctg cag gtg cgg gca ggg ccc     626
Glu Phe Arg Lys Asp Ser Ser Tyr Glu Leu Gln Val Arg Ala Gly Pro
    190             195             200 atg cct ggc tcc tcc tac cag ggg acc tgg agt gaa tgg agt gac ccg     674
Met Pro Gly Ser Ser Tyr Gln Gly Thr Trp Ser Glu Trp Ser Asp Pro
205             210             215             220
```

Figure 10A

```
gtc atc ttt cag acc cag tca gag gag tta aag gaa ggc tgg aac ggc      722
Val Ile Phe Gln Thr Gln Ser Glu Glu Leu Lys Glu Gly Trp Asn Gly
            225                 230                 235 tcc ggc tct aga gac aaa act cac aca tgc cca ccg tgc cca gca cct      770
Ser Gly Ser Arg Asp Lys Thr His Thr Cys Pro Pro Cys Pro Ala Pro
            240                 245                 250 gaa gcc ctg ggg gca ccg tca gtc ttc ctc ttc ccc cca aaa ccc aag      818
Glu Ala Leu Gly Ala Pro Ser Val Phe Leu Phe Pro Pro Lys Pro Lys
            255                 260                 265 gac acc ctc atg atc tcc cgg acc cct gag gtc aca tgc gtg gtg gtg      866
Asp Thr Leu Met Ile Ser Arg Thr Pro Glu Val Thr Cys Val Val Val
            270                 275                 280 gac gtg agc cac gaa gac cct gag gtc aag ttc aac tgg tac gtg gac      914
Asp Val Ser His Glu Asp Pro Glu Val Lys Phe Asn Trp Tyr Val Asp
285                 290                 295                 300 ggc gtg gag gtg cat aat gcc aag aca aag ccg cgg gag gag cag tac      962
Gly Val Glu Val His Asn Ala Lys Thr Lys Pro Arg Glu Glu Gln Tyr
            305                 310                 315 aac agc acg tac cgt gtg gtc agc gtc ctc acc gtc ctg cac cag gac     1010
Asn Ser Thr Tyr Arg Val Val Ser Val Leu Thr Val Leu His Gln Asp
            320                 325                 330 tgg ctg aat ggc aag gag tac aag tgc aag gtc tcc aac aaa gcc ctc     1058
Trp Leu Asn Gly Lys Glu Tyr Lys Cys Lys Val Ser Asn Lys Ala Leu
            335                 340                 345 cca gcc ccc atc gag aaa acc atc tcc aaa gcc aaa ggg cag ccc cga     1106
Pro Ala Pro Ile Glu Lys Thr Ile Ser Lys Ala Lys Gly Gln Pro Arg
            350                 355                 360 gaa cca cag gtg tac acc ctg ccc cca tcc cgg gag gag atg acc aag     1154
Glu Pro Gln Val Tyr Thr Leu Pro Pro Ser Arg Glu Glu Met Thr Lys
365                 370                 375                 380 aac cag gtc agc ctg acc tgc ctg gtc aaa ggc ttc tat ccc agc gac     1202
Asn Gln Val Ser Leu Thr Cys Leu Val Lys Gly Phe Tyr Pro Ser Asp
            385                 390                 395 atc gcc gtg gag tgg gag agc aat ggg cag ccg gag aac aac tac aag     1250
Ile Ala Val Glu Trp Glu Ser Asn Gly Gln Pro Glu Asn Asn Tyr Lys
            400                 405                 410 acc acg cct ccc gtg ctg gac tcc gac ggc tcc ttc ttc ctc tat agc     1298
Thr Thr Pro Pro Val Leu Asp Ser Asp Gly Ser Phe Phe Leu Tyr Ser
            415                 420                 425 aag ctc acc gtg gac aag agc agg tgg cag cag ggg aac gtc ttc tca     1346
Lys Leu Thr Val Asp Lys Ser Arg Trp Gln Gln Gly Asn Val Phe Ser
            430                 435                 440
```

Figure 10B

```
tgc tcc gtg atg cat gag gct ctg cac aac cac tac acg cag aag agc      1394
Cys Ser Val Met His Glu Ala Leu His Asn His Tyr Thr Gln Lys Ser
445             450             455             460 ctc tcc ctg tcc ccg ggt aaa tgagtgaatt c SEQ ID NO: 28               1426
Leu Ser Leu Ser Pro Gly Lys  SEQ ID NO: 29
                465
```

Figure 10C

| | | | | | | | | | | | | | | | |
|---|---|---|---|---|---|---|---|---|---|---|---|---|---|---|---|
| atg | ccg | cgt | ggc | tgg | gcc | gcc | ccc | ttg | ctc | ctg | ctg | ctg | ctc | cag | gga | 48 |
| Met | Pro | Arg | Gly | Trp | Ala | Ala | Pro | Leu | Leu | Leu | Leu | Leu | Leu | Gln | Gly | |
| 1 | | | | 5 | | | | | 10 | | | | | 15 | | | ggc tgg ggc tgc ccc gac ctc gtc tgc tac acc gat tac ctc cag acg    96
Gly Trp Gly Cys Pro Asp Leu Val Cys Tyr Thr Asp Tyr Leu Gln Thr
              20                  25                  30 gtc atc tgc atc ctg gaa atg tgg aac ctc cac ccc agc acg ctc acc   144
Val Ile Cys Ile Leu Glu Met Trp Asn Leu His Pro Ser Thr Leu Thr
         35                  40                  45 ctt acc tgg caa gac cag tat gaa gag ctg aag gac gag gcc acc tcc   192
Leu Thr Trp Gln Asp Gln Tyr Glu Glu Leu Lys Asp Glu Ala Thr Ser
     50                  55                  60 tgc agc ctc cac agg tcg gcc cac aat gcc acg cat gcc acc tac acc   240
Cys Ser Leu His Arg Ser Ala His Asn Ala Thr His Ala Thr Tyr Thr
65                  70                  75                  80 tgc cac atg gat gta ttc cac ttc atg gcc gac gac att ttc agt gtc   288
Cys His Met Asp Val Phe His Phe Met Ala Asp Asp Ile Phe Ser Val
                 85                  90                  95 aac atc aca gac cag tct ggc aac tac tcc cag gag tgt ggc agc ttt   336
Asn Ile Thr Asp Gln Ser Gly Asn Tyr Ser Gln Glu Cys Gly Ser Phe
             100                 105                 110 ctc ctg gct gag agc atc aag ccg gct ccc cct ttc aac gtg act gtg   384
Leu Leu Ala Glu Ser Ile Lys Pro Ala Pro Pro Phe Asn Val Thr Val
         115                 120                 125 acc ttc tca gga cag tat aat atc tcc tgg cgc tca gat tac gaa gac   432
Thr Phe Ser Gly Gln Tyr Asn Ile Ser Trp Arg Ser Asp Tyr Glu Asp
     130                 135                 140 cct gcc ttc tac atg ctg aag ggc aag ctt cag tat gag ctg cag tac   480
Pro Ala Phe Tyr Met Leu Lys Gly Lys Leu Gln Tyr Glu Leu Gln Tyr
145                 150                 155                 160 agg aac cgg gga gac ccc tgg gct gtg agt ccg agg aga aag ctg atc   528
Arg Asn Arg Gly Asp Pro Trp Ala Val Ser Pro Arg Arg Lys Leu Ile
                 165                 170                 175 tca gtg gac tca aga agt gtc tcc ctc ctc ccc ctg gag ttc cgc aaa   576
Ser Val Asp Ser Arg Ser Val Ser Leu Leu Pro Leu Glu Phe Arg Lys
             180                 185                 190 gac tcg agc tat gag ctg cag gtg cgg gca ggg ccc atg cct ggc tcc   624
Asp Ser Ser Tyr Glu Leu Gln Val Arg Ala Gly Pro Met Pro Gly Ser
         195                 200                 205 tcc tac cag ggg acc tgg agt gaa tgg agt gac ccg gtc atc ttt cag   672
Ser Tyr Gln Gly Thr Trp Ser Glu Trp Ser Asp Pro Val Ile Phe Gln
     210                 215                 220

Figure 11A

```
acc cag tca gag gag tta aag gaa ggc tgg aac aaa acc gaa acc tcc        720
Thr Gln Ser Glu Glu Leu Lys Glu Gly Trp Asn Lys Thr Glu Thr Ser
225             230                 235                 240 cag gtt gct ccg gca taa tga SEQ ID NO: 30                              741
Gln Val Ala Pro Ala SEQ ID NO: 31
                245
```

Figure 11B

```
atg ccg cgt ggc tgg gcc gcc ccc ttg ctc ctg ctg ctg ctc cag gga    48
Met Pro Arg Gly Trp Ala Ala Pro Leu Leu Leu Leu Leu Leu Gln Gly
1               5                   10                  15 ggc tgg ggc tgc ccc gac ctc gtc tgc tac acc gat tac ctc cag acg    96
Gly Trp Gly Cys Pro Asp Leu Val Cys Tyr Thr Asp Tyr Leu Gln Thr
            20                  25                  30 gtc atc tgc atc ctg gaa atg tgg aac ctc cac ccc agc acg ctc acc   144
Val Ile Cys Ile Leu Glu Met Trp Asn Leu His Pro Ser Thr Leu Thr
        35                  40                  45 ctt acc tgg caa gac cag tat gaa gag ctg aag gac gag gcc acc tcc   192
Leu Thr Trp Gln Asp Gln Tyr Glu Glu Leu Lys Asp Glu Ala Thr Ser
    50                  55                  60 tgc agc ctc cac agg tcg gcc cac aat gcc acg cat gcc acc tac acc   240
Cys Ser Leu His Arg Ser Ala His Asn Ala Thr His Ala Thr Tyr Thr
65                  70                  75                  80 tgc cac atg gat gta ttc cac ttc atg gcc gac gac att ttc agt gtc   288
Cys His Met Asp Val Phe His Phe Met Ala Asp Asp Ile Phe Ser Val
                85                  90                  95 aac atc aca gac cag tct ggc aac tac tcc cag gag tgt ggc agc ttt   336
Asn Ile Thr Asp Gln Ser Gly Asn Tyr Ser Gln Glu Cys Gly Ser Phe
            100                 105                 110 ctc ctg gct gag agc atc aag ccg gct ccc cct ttc aac gtg act gtg   384
Leu Leu Ala Glu Ser Ile Lys Pro Ala Pro Pro Phe Asn Val Thr Val
        115                 120                 125 acc ttc tca gga cag tat aat atc tcc tgg cgc tca gat tac gaa gac   432
Thr Phe Ser Gly Gln Tyr Asn Ile Ser Trp Arg Ser Asp Tyr Glu Asp
    130                 135                 140 cct gcc ttc tac atg ctg aag ggc aag ctt cag tat gag ctg cag tac   480
Pro Ala Phe Tyr Met Leu Lys Gly Lys Leu Gln Tyr Glu Leu Gln Tyr
145                 150                 155                 160 agg aac cgg gga gac ccc tgg gct gtg agt ccg agg aga aag ctg atc   528
Arg Asn Arg Gly Asp Pro Trp Ala Val Ser Pro Arg Arg Lys Leu Ile
                165                 170                 175 tca gtg gac tca aga agt gtc tcc ctc ctc ccc ctg gag ttc cgc aaa   576
Ser Val Asp Ser Arg Ser Val Ser Leu Leu Pro Leu Glu Phe Arg Lys
            180                 185                 190 gac tcg agc tat gag ctg cag gtg cgg gca ggg ccc atg cct ggc tcc   624
Asp Ser Ser Tyr Glu Leu Gln Val Arg Ala Gly Pro Met Pro Gly Ser
        195                 200                 205 tcc tac cag ggg acc tgg agt gaa tgg agt gac ccg gtc atc ttt cag   672
Ser Tyr Gln Gly Thr Trp Ser Glu Trp Ser Asp Pro Val Ile Phe Gln
    210                 215                 220
```

Figure 12A

```
acc cag tca gag gag tta aag gaa ggc tgg aac gat gac gat gac aag      720
Thr Gln Ser Glu Glu Leu Lys Glu Gly Trp Asn Asp Asp Asp Asp Lys
225             230                 235                 240 ggc tcc ggc gac aaa act cac aca tgc cca ccg tgc cca gca cct gaa      768
Gly Ser Gly Asp Lys Thr His Thr Cys Pro Pro Cys Pro Ala Pro Glu
                245                 250                 255 gcc ctg ggg gca ccg tca gtc ttc ctc ttc ccc cca aaa ccc aag gac      816
Ala Leu Gly Ala Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccg cgg gag gag cag tac aac      960
Val Glu Val His Asn Ala Lys Thr Lys Pro Arg Glu Glu Gln Tyr Asn
305             310                 315                 320 agc acg tac cgt gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggg cag ccc cga gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385             390                 395                 400 gcc gtg gag tgg gag agc aat ggg cag ccg gag aac aac tac aag acc     1248
Ala Val Glu Trp Glu Ser Asn Gly Gln Pro Glu Asn Asn Tyr Lys Thr
                405                 410                 415 acg cct ccc gtg ctg gac tcc gac ggc tcc ttc ttc ctc tat agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggg aac gtc ttc tca tgc     1344
Leu Thr Val Asp Lys Ser Arg Trp Gln Gln Gly Asn Val Phe Ser Cys
        435                 440                 445
```

Figure 12B

```
tcc gtg atg cat gag gct ctg cac aac cac tac acg cag aag agc ctc      1392
Ser Val Met His Glu Ala Leu His Asn His Tyr Thr Gln Lys Ser Leu
    450             455                 460 tcc ctg tcc ccg ggt aaa tga SEQ ID NO: 32                            1413
Ser Leu Ser Pro Gly Lys     SEQ ID NO: 33
465             470
```

Figure 12C

| | | |
|---|---|---|
| atg ccc cgg ggc cca gtg gct gcc tta ctc ctg ctg att ctc cat gga<br>Met Pro Arg Gly Pro Val Ala Ala Leu Leu Leu Leu Ile Leu His Gly<br>1              5                       10                  15 | 48 |
| gct tgg agc tgc ctg gac ctc act tgc tac act gac tac ctc tgg acc<br>Ala Trp Ser Cys Leu Asp Leu Thr Cys Tyr Thr Asp Tyr Leu Trp Thr<br>                 20                   25                  30 | 96 |
| atc acc tgt gtc ctg gag aca cgg agc ccc aac ccc agc ata ctc agt<br>Ile Thr Cys Val Leu Glu Thr Arg Ser Pro Asn Pro Ser Ile Leu Ser<br>        35                    40                    45 | 144 |
| ctc acc tgg caa gat gaa tat gag gaa ctt cag gac caa gag acc ttc<br>Leu Thr Trp Gln Asp Glu Tyr Glu Glu Leu Gln Asp Gln Glu Thr Phe<br>     50                    55                    60 | 192 |
| tgc agc cta cac agg tct ggc cac aac acc aca cat ata tgg tac acg<br>Cys Ser Leu His Arg Ser Gly His Asn Thr Thr His Ile Trp Tyr Thr<br>65                   70                    75                80 | 240 |
| tgc cat atg cgc ttg tct caa ttc ctg tcc gat gaa gtt ttc att gtc<br>Cys His Met Arg Leu Ser Gln Phe Leu Ser Asp Glu Val Phe Ile Val<br>               85                    90                  95 | 288 |
| aat gtg acg gac cag tct ggc aac aac tcc caa gag tgt ggc agc ttt<br>Asn Val Thr Asp Gln Ser Gly Asn Asn Ser Gln Glu Cys Gly Ser Phe<br>            100                    105              110 | 336 |
| gtc ctg gct gag agc atc aaa cca gct ccc ccc ttg aac gtg act gtg<br>Val Leu Ala Glu Ser Ile Lys Pro Ala Pro Pro Leu Asn Val Thr Val<br>         115                    120                    125 | 384 |
| gcc ttc tca gga cgc tat gat atc tcc tgg gac tca gct tat gac gaa<br>Ala Phe Ser Gly Arg Tyr Asp Ile Ser Trp Asp Ser Ala Tyr Asp Glu<br>130                      135                    140 | 432 |
| ccc tcc aac tac gtg ctg agg ggc aag cta caa tat gag ctg cag tat<br>Pro Ser Asn Tyr Val Leu Arg Gly Lys Leu Gln Tyr Glu Leu Gln Tyr<br>145                      150                  155                160 | 480 |
| cgg aac ctc aga gac ccc tat gct gtg agg ccg gtg acc aag ctg atc<br>Arg Asn Leu Arg Asp Pro Tyr Ala Val Arg Pro Val Thr Lys Leu Ile<br>               165                    170                  175 | 528 |
| tca gtg gac tca aga aac gtc tct ctt ctc cct gaa gag ttc cac aaa<br>Ser Val Asp Ser Arg Asn Val Ser Leu Leu Pro Glu Glu Phe His Lys<br>                  180                    185                  190 | 576 |
| gat tct agc tac cag ctg cag gtg cgg gca gcg cct cag cca ggc act<br>Asp Ser Ser Tyr Gln Leu Gln Val Arg Ala Ala Pro Gln Pro Gly Thr<br>                 195                    200                205 | 624 |
| tca ttc agg ggg acc tgg agt gag tgg agt gac ccc gtc atc ttt cag<br>Ser Phe Arg Gly Thr Trp Ser Glu Trp Ser Asp Pro Val Ile Phe Gln<br>        210                    215                    220 | 672 |

Figure 13A

| | | | | | | | | | | | | | | | |
|---|---|---|---|---|---|---|---|---|---|---|---|---|---|---|---|
| acc | cag | gct | ggg | gag | ccc | gag | gca | ggc | tgg | gac | ggc | tcc | ggc | tct | aga |
| Thr | Gln | Ala | Gly | Glu | Pro | Glu | Ala | Gly | Trp | Asp | Gly | Ser | Gly | Ser | Arg (35) |
| 225 | | | | 230 | | | | | 235 | | | | | 240 | |

720

```
gagccccgcg gaccgacaat caagccctgt cctccatgca aatgcccagg taagtcacta      780
gaccagagct ccactcccgg gagaatggta agtgctataa acatccctgc actagaggat      840
aagccatgta cagatccatt tccatctctc ctcatcagca cctaacctcg agggtggacc      900
atccgtcttc atcttccctc caaagatcaa ggatgtactc atgatctccc tgagccccat      960
agtcacatgt gtggtggtgg atgtgagcga ggatgaccca gatgtccaga tcagctggtt     1020
tgtgaacaac gtggaagtac acacagctca gacacaaacc catagagagg attacaacag     1080
tactctccgg gtggtcagtg ccctccccat ccagcaccag gactggatga gtggcaaggc     1140
tttcgcatgc gccgtcaaca acaaagacct cccagcgccc atcgagagaa ccatctcaaa     1200
acccaaaggt gagagctgca gcctgactgc atggggctg ggatgggcat aaggataaag     1260
gtctgtgtgg acagccttct gcttcagcca tgacctttgt gtatgtttct accctcacag     1320
ggtcagtaag agctccacag gtatatgtct tgcctccacc agaagaagag atgactaaga     1380
aacaggtcac tctgacctgc atggtcacag acttcatgcc tgaagacatt tacgtggagt     1440
ggaccaacaa cgggaaaaca gagctaaact acaagaacac tgaaccagtc ctggactctg     1500
atggttctta cttcatgtac agcaagctga gagtggaaaa gaagaactgg gtggaaagaa     1560
atagctactc ctgttcagtg gtccacgagg gtctgcacaa tcaccacacg actaagagct     1620
tctcccggac tcgggtaaa tgagctcagc acccacaaaa ctctcaggtc caaagagaca     1680
cccacactca tctccatgct tcccttgtat aaataaagca cccagcaatg cctgggacca     1740
tgtaatagga attc SEQ ID NO:34                                          1754
```

Figure 13B

```
ctgcaggtcg acaccacc atg ccc cgg ggc cca gtg gct gcc tta ctc ctg         51
                    Met Pro Arg Gly Pro Val Ala Ala Leu Leu Leu
                     1           5                       10 ctg att ctc cat gga gct tgg agc tgc ctg gac ctc act tgc tac act         99
Leu Ile Leu His Gly Ala Trp Ser Cys Leu Asp Leu Thr Cys Tyr Thr
             15              20                  25 gac tac ctc tgg acc atc acc tgt gtc ctg gag aca cgg agc ccc aac        147
Asp Tyr Leu Trp Thr Ile Thr Cys Val Leu Glu Thr Arg Ser Pro Asn
         30              35                  40 ccc agc ata ctc agt ctc acc tgg caa gat gaa tat gag gaa ctt cag        195
Pro Ser Ile Leu Ser Leu Thr Trp Gln Asp Glu Tyr Glu Glu Leu Gln
    45              50                  55 gac caa gag acc ttc tgc agc cta cac agg tct ggc cac aac acc aca        243
Asp Gln Glu Thr Phe Cys Ser Leu His Arg Ser Gly His Asn Thr Thr
60              65                  70                  75 cat ata tgg tac acg tgc cat atg cgc ttg tct caa ttc ctg tcc gat        291
His Ile Trp Tyr Thr Cys His Met Arg Leu Ser Gln Phe Leu Ser Asp
             80                  85                  90 gaa gtt ttc att gtc aat gtg acg gac cag tct ggc aac aac tcc caa        339
Glu Val Phe Ile Val Asn Val Thr Asp Gln Ser Gly Asn Asn Ser Gln
             95                  100                 105 gag tgt ggc agc ttt gtc ctg gct gag agc atc aaa cca gct ccc ccc        387
Glu Cys Gly Ser Phe Val Leu Ala Glu Ser Ile Lys Pro Ala Pro Pro
        110                 115                 120 ttg aac gtg act gtg gcc ttc tca gga cgc tat gat atc tcc tgg gac        435
Leu Asn Val Thr Val Ala Phe Ser Gly Arg Tyr Asp Ile Ser Trp Asp
    125                 130                 135 tca gct tat gac gaa ccc tcc aac tac gtg ctg agg ggc aag cta caa        483
Ser Ala Tyr Asp Glu Pro Ser Asn Tyr Val Leu Arg Gly Lys Leu Gln
140             145                 150                 155 tat gag ctg cag tat cgg aac ctc aga gac ccc tat gct gtg agg ccg        531
Tyr Glu Leu Gln Tyr Arg Asn Leu Arg Asp Pro Tyr Ala Val Arg Pro
            160                 165                 170 gtg acc aag ctg atc tca gtg gac tca aga aac gtc tct ctt ctc cct        579
Val Thr Lys Leu Ile Ser Val Asp Ser Arg Asn Val Ser Leu Leu Pro
        175                 180                 185 gaa gag ttc cac aaa gat tct agc tac cag ctg cag gtg cgg gca gcg        627
Glu Glu Phe His Lys Asp Ser Ser Tyr Gln Leu Gln Val Arg Ala Ala
        190                 195                 200 cct cag cca ggc act tca ttc agg ggg acc tgg agt gag tgg agt gac        675
Pro Gln Pro Gly Thr Ser Phe Arg Gly Thr Trp Ser Glu Trp Ser Asp
205                 210                 215
```

Figure 14A

```
ccc gtc atc ttt cag acc cag gct ggg gag ccc gag gca ggc tgg gac    723
Pro Val Ile Phe Gln Thr Gln Ala Gly Glu Pro Glu Ala Gly Trp Asp
220             225             230             235 ggc agc gga cac cac cat cat cac cac ggt agc ggc gac tat aaa gac    771
Gly Ser Gly His His His His His His Gly Ser Gly Asp Tyr Lys Asp
            240             245             250 gat gac gat aag tagtgagaat tc SEQ ID NO: 36                        795
Asp Asp Asp Lys    SEQ ID NO: 37
               255
```

Figure 14B

| | | | | | | | | | | | | | | | | |
|---|---|---|---|---|---|---|---|---|---|---|---|---|---|---|---|---|
| atg | aaa | ttc | tta | gtc | aac | gtt | gcc | ctt | gtt | ttt | atg | gtc | gtg | tac | att | 48 |
| Met | Lys | Phe | Leu | Val | Asn | Val | Ala | Leu | Val | Phe | Met | Val | Val | Tyr | Ile | |
| 1 | | | | 5 | | | | | 10 | | | | | 15 | | |
| tct | tac | atc | tat | gcc | ggc | agc | gga | cac | cac | cat | cat | cac | cac | ggt | agc | 96 |
| Ser | Tyr | Ile | Tyr | Ala | Gly | Ser | Gly | His | His | His | His | His | His | Gly | Ser | |
| | | | 20 | | | | | 25 | | | | | 30 | | | |
| ggc | gac | tat | aaa | gac | gat | gac | gat | aag | ggt | tcc | gga | tgc | ctg | gac | ctc | 144 |
| Gly | Asp | Tyr | Lys | Asp | Asp | Asp | Asp | Lys | Gly | Ser | Gly | Cys | Leu | Asp | Leu | |
| | | | 35 | | | | | 40 | | | | | 45 | | | |
| act | tgc | tac | act | gac | tac | ctc | tgg | acc | atc | acc | tgt | gtc | ctg | gag | aca | 192 |
| Thr | Cys | Tyr | Thr | Asp | Tyr | Leu | Trp | Thr | Ile | Thr | Cys | Val | Leu | Glu | Thr | |
| | | | 50 | | | | | 55 | | | | | 60 | | | |
| cgg | agc | ccc | aac | ccc | agc | ata | ctc | agt | ctc | acc | tgg | caa | gat | gaa | tat | 240 |
| Arg | Ser | Pro | Asn | Pro | Ser | Ile | Leu | Ser | Leu | Thr | Trp | Gln | Asp | Glu | Tyr | |
| 65 | | | | | 70 | | | | | 75 | | | | | 80 | |
| gag | gaa | ctt | cag | gac | caa | gag | acc | ttc | tgc | agc | cta | cac | agg | tct | ggc | 288 |
| Glu | Glu | Leu | Gln | Asp | Gln | Glu | Thr | Phe | Cys | Ser | Leu | His | Arg | Ser | Gly | |
| | | | | 85 | | | | | 90 | | | | | 95 | | |
| cac | aac | acc | aca | cat | ata | tgg | tac | acg | tgc | cat | atg | cgc | ttg | tct | caa | 336 |
| His | Asn | Thr | Thr | His | Ile | Trp | Tyr | Thr | Cys | His | Met | Arg | Leu | Ser | Gln | |
| | | | 100 | | | | | 105 | | | | | 110 | | | |
| ttc | ctg | tcc | gat | gaa | gtt | ttc | att | gtc | aat | gtg | acg | gac | cag | tct | ggc | 384 |
| Phe | Leu | Ser | Asp | Glu | Val | Phe | Ile | Val | Asn | Val | Thr | Asp | Gln | Ser | Gly | |
| | | | 115 | | | | | 120 | | | | | 125 | | | |
| aac | aac | tcc | caa | gag | tgt | ggc | agc | ttt | gtc | ctg | gct | gag | agc | atc | aaa | 432 |
| Asn | Asn | Ser | Gln | Glu | Cys | Gly | Ser | Phe | Val | Leu | Ala | Glu | Ser | Ile | Lys | |
| | | | 130 | | | | | 135 | | | | | 140 | | | |
| cca | gct | ccc | ccc | ttg | aac | gtg | act | gtg | gcc | ttc | tca | gga | cgc | tat | gat | 480 |
| Pro | Ala | Pro | Pro | Leu | Asn | Val | Thr | Val | Ala | Phe | Ser | Gly | Arg | Tyr | Asp | |
| 145 | | | | | 150 | | | | | 155 | | | | | 160 | |
| atc | tcc | tgg | gac | tca | gct | tat | gac | gaa | ccc | tcc | aac | tac | gtg | ctg | agg | 528 |
| Ile | Ser | Trp | Asp | Ser | Ala | Tyr | Asp | Glu | Pro | Ser | Asn | Tyr | Val | Leu | Arg | |
| | | | 165 | | | | | 170 | | | | | 175 | | | |
| ggc | aag | cta | caa | tat | gag | ctg | cag | tat | cgg | aac | ctc | aga | gac | ccc | tat | 576 |
| Gly | Lys | Leu | Gln | Tyr | Glu | Leu | Gln | Tyr | Arg | Asn | Leu | Arg | Asp | Pro | Tyr | |
| | | | 180 | | | | | 185 | | | | | 190 | | | |
| gct | gtg | agg | ccg | gtg | acc | aag | ctg | atc | tca | gtg | gac | tca | aga | aac | gtc | 624 |
| Ala | Val | Arg | Pro | Val | Thr | Lys | Leu | Ile | Ser | Val | Asp | Ser | Arg | Asn | Val | |
| | | 195 | | | | | 200 | | | | | 205 | | | | |
| tct | ctt | ctc | cct | gaa | gag | ttc | cac | aaa | gat | tct | agc | tac | cag | ctg | cag | 672 |
| Ser | Leu | Leu | Pro | Glu | Glu | Phe | His | Lys | Asp | Ser | Ser | Tyr | Gln | Leu | Gln | |
| | | 210 | | | | | 215 | | | | | 220 | | | | |

Figure 15A

```
gtg cgg gca gcg cct cag cca ggc act tca ttc agg ggg acc tgg agt       720
Val Arg Ala Ala Pro Gln Pro Gly Thr Ser Phe Arg Gly Thr Trp Ser
225             230              235              240 gag tgg agt gac ccc gtc atc ttt cag acc cag gct ggg gag ccc gag       768
Glu Trp Ser Asp Pro Val Ile Phe Gln Thr Gln Ala Gly Glu Pro Glu
             245              250              255 gca ggc tgg gac tagtgagaat tc  SEQ ID NO: 38                          792
Ala Gly Trp Asp               SEQ ID NO: 39
             260
```

Figure 15B

SEQUENCE LISTING

<160> NUMBER OF SEQ ID NOS: 44

<210> SEQ ID NO 1
<211> LENGTH: 2665
<212> TYPE: DNA
<213> ORGANISM: Human

<400> SEQUENCE: 1

```
gtcgactgga ggcccagctg cccgtcatca gagtgacagg tcttatgaca gcctgattgg      60
tgactcgggc tgggtgtgga ttctcacccc aggcctctgc ctgctttctc agaccctcat     120
ctgtcacccc cacgctgaac ccagctgcca ccccagaag cccatcagac tgcccccagc     180
acacggaatg gatttctgag aaagaagccg aaacagaagg cccgtgggag tcagcatgcc     240
gcgtggctgg gccgccccct tgctcctgct gctgctccag ggaggctggg gctgcccga      300 cctcgtctgc tacaccgatt acctccagac ggtcatctgc atcctggaaa tgtggaacct     360
ccaccccagc acgctcaccc ttacctggca agaccagtat gaagagctga aggacgaggc     420
cacctcctgc agcctccaca ggtcggccca caatgccacg catgccacct acacctgcca     480
catggatgta ttccacttca tggccgacga cattttcagt gtcaacatca cagaccagtc     540
tggcaactac tcccaggagt gtggcagctt tctcctggct gagagcatca gccggctcc      600 cccttttcaac gtgactgtga ccttctcagg acagtataat atctcctggc gctcagatta     660
cgaagaccct gccttctaca tgctgaaggg caagcttcag tatgagctgc agtacaggaa     720
ccggggagac ccctgggctg tgagtccgag gagaaagctg atctcagtgg actcaagaag     780
tgtctccctc ctcccctgg agttccgcaa agactcgagc tatgagctgc aggtgcgggc     840
agggcccatg cctggctcct cctaccaggg gacctggagt gaatggagtg acccggtcat     900 cttcagacc cagtcagagg agttaaagga aggctggaac cctcacctgc tgcttctcct     960
cctgcttgtc atagtcttca ttcctgcctt ctggagcctg aagacccatc cattgtggag    1020
```

-continued

```
gctatggaag aagatatggg ccgtcgccag ccctgagcgg ttcttcatgc ccctgtacaa   1080
gggctgcagc ggagacttca agaaatgggt gggtgcaccc ttcactggct ccagcctgga   1140
gctgggaccc tggagcccag aggtgccctc caccctggag gtgtacagct gccacccacc   1200
acggagcccg gccaagaggc tgcagctcac ggagctacaa gaaccagcag agctggtgga   1260
gtctgacggt gtgcccaagc ccagcttctg gccgacagcc cagaactcgg ggggctcagc   1320
ttacagtgag gagagggatc ggccatacgg cctggtgtcc attgacacag tgactgtgct   1380
agatgcagag gggccatgca cctggccctg cagctgtgag gatgacggct acccagccct   1440
ggacctggat gctggcctgg agcccagccc aggcctagag acccactct tggatgcagg    1500
gaccacagtc ctgtcctgtg gctgtgtctc agctggcagc cctgggctag agggcccct    1560
gggaagcctc ctggacagac taaagccacc ccttgcagat ggggaggact gggctggggg    1620
actgccctgg ggtggccggt cacctggagg ggtctcagag agtgaggcgg gctcaccct    1680
ggccggcctg gatatggaca cgtttgacag tggctttgtg ggctctgact gcagcagccc    1740
tgtggagtgt gacttcacca gccccgggga cgaaggaccc cccggagct acctccgcca    1800
gtgggtggtc attcctccgc cactttcgag ccctggaccc caggccagct aatgaggctg    1860
actggatgtc cagagctggc caggccactg ggccctgagc cagagacaag gtcacctggg    1920
ctgtgatgtg aagacacctg cagcctttgg tctcctggat gggcctttga gcctgatgtt    1980
tacagtgtct gtgtgtgtgt gtgcatatgt gtgtgtgtgc atatgcatgt gtgtgtgtgt    2040
gtgtgtctta ggtgcgcagt ggcatgtcca cgtgtgtgtg tgattgcacg tgcctgtggg    2100
cctgggataa tgcccatggt actccatgca ttcacctgcc ctgtgcatgt ctggactcac    2160
ggagctcacc catgtgcaca agtgtgcaca gtaaacgtgt ttgtggtcaa cagatgacaa    2220
cagccgtcct ccctcctagg gtcttgtgtt gcaagttggt ccacagcatc tccggggctt    2280
tgtgggatca gggcattgcc tgtgactgag gcggagccca gccctccagc gtctgcctcc    2340
aggagctgca agaagtccat attgttcctt atcacctgcc aacaggaagc gaaagggat     2400
ggagtgagcc catggtgacc tcgggaatgg caattttttg gcgggccct ggacgaaggt     2460
ctgaatcccg actctgatac cttctggctg tgctacctga gccaagtcgc ctccctctc    2520
tgggctagag tttccttatc cagacagtgg ggaaggcatg acacacctgg gggaaattgg    2580
cgatgtcacc cgtgtacggt acgcagccca gagcagaccc tcaataaacg tcagcttcct    2640
tcaaaaaaaa aaaaaaaat ctaga                                          2665
```

<210> SEQ ID NO 2
<211> LENGTH: 538
<212> TYPE: PRT
<213> ORGANISM: Human
<400> SEQUENCE: 2

```
Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
        50                  55                  60

Cys Ser Leu His Arg Ser Ala His Asn Ala Thr His Ala Thr Tyr Thr
65                  70                  75                  80
```

-continued

```
Cys His Met Asp Val Phe His Phe Met Ala Asp Asp Ile Phe Ser Val
            85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
            115                 120                 125

Thr Phe Ser Gly Gln Tyr Asn Ile Ser Trp Arg Ser Asp Tyr Glu Asp
            130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
            165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
            210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
            245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
            325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
            355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
            405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
            435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
            485                 490                 495

Ser Asp Cys Ser Ser Pro Val Glu Cys Asp Phe Thr Ser Pro Gly Asp
```

-continued

```
                500              505             510
Glu Gly Pro Pro Arg Ser Tyr Leu Arg Gln Trp Val Val Ile Pro Pro
            515                 520                 525

Pro Leu Ser Ser Pro Gly Pro Gln Ala Ser
    530                 535

<210> SEQ ID NO 3
<211> LENGTH: 70
<212> TYPE: PRT
<213> ORGANISM: Human

<400> SEQUENCE: 3

Leu Met Thr Asn Ala Phe Ile Ser Ile Ile Asp Asp Leu Ser Lys Tyr
1               5                  10                  15

Asp Val Gln Val Arg Ala Ala Val Ser Ser Met Cys Arg Glu Ala Gly
            20                  25                  30

Leu Trp Ser Glu Trp Ser Gln Pro Ile Tyr Val Gly Asn Asp Glu His
        35                  40                  45

Lys Pro Leu Arg Glu Trp Phe Val Ile Val Met Ala Thr Ile Cys
    50                  55                  60

Phe Ile Leu Leu Ile Leu
65                  70

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 4
gagtccgagg agaaagctga tctca                                          25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 5
gaaagatgac cgggtcactc catt                                           24

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Labelled
      Hybridization Oligonucleotide

<400> SEQUENCE: 6
actcgagcta tgagctgcag gtgcgggca                                      29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: NN14-1b
      (MU-1) Labelled Hybridization Oligonucleotide

<400> SEQUENCE: 7
```

```
actcgagcta tgagctgcag gtgcgggca                                      29
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Motif
      Characteristic of the Hematopoietin Receptor Family
<220> FEATURE:
<221> NAME/KEY: MISC_FEATURE
<222> LOCATION: (3)..(3)
<223> OTHER INFORMATION: Wherein Xaa is any amino acid.

<400> SEQUENCE: 8

Trp Ser Xaa Trp Ser
1               5

<210> SEQ ID NO 9
<211> LENGTH: 2628
<212> TYPE: DNA
<213> ORGANISM: Mouse

<400> SEQUENCE: 9

```
gtcgacgcgg cggtaccagc tgtctgccca cttctcctgt ggtgtgcctc acggtcactt     60
gcttgtctga ccgcaagtct gcccatccct ggggcagcca actggcctca gcccgtgccc    120
caggcgtgcc ctgtctctgt ctggctgccc cagccctact gtcttcctct gtgtaggctc    180
tgcccagatg cccggctggt cctcagcctc aggactatct cagcagtgac tcccctgatt    240
ctggacttgc acctgactga actcctgccc acctcaaacc ttcacctccc accaccacca    300
ctccgagtcc cgctgtgact cccacgccca ggagaccacc caagtgcccc agcctaaaga    360
atggctttct gagaaagacc ctgaaggagt aggtctggga cacagcatgc cccggggccc    420
actggctgcc ttactcctgc tgattctcca tggagcttgg agctgcctgg acctcacttg    480
ctacactgac tacctctgga ccatcacctg tgtcctggag acacggagcc ccaaccccag    540
catactcagt ctcacctggc aagatgaata tgaggaactt caggaccaag agaccttctg    600
cagcctacac aggtctggcc acaacaccac acatatatgg tacacgtgcc atatgcgctt    660
gtctcaattc ctgtccgatg aagttttcat tgtcaatgtg acggaccagt ctggcaacaa    720
ctcccaagag tgtggcagct tgtcctggc tgagagcatc aaaccagctc ccccttgaa     780
cgtgactgtg gccttctcag gacgctatga tatctcctgg gactcagctt atgacgaacc    840
ctccaactac gtgctgaggg gcaagctaca atatgagctg cagtatcgga acctcagaga    900
ccctatgct gtgaggccgg tgaccaagct gatctcagtg gactcaagaa acgtctctct    960
tctccctgaa gagttccaca agattctag ctaccagctg caggtgcggg cagcgcctca   1020
gccaggcact tcattcaggg ggacctggag tgagtggagt gaccccgtca tctttcagac   1080
ccaggctggg gagcccgagg caggctggga ccctcacatg ctgctgctcc tggctgtctt   1140
gatcattgtc ctggttttca cgggtctgaa gatccacctg ccttggaggc tatggaaaaa   1200
gatatgggca ccagtgccca cccctgagag tttcttccag cccctgtaca gggagcacag   1260
cgggaacttc aagaaatggg ttaatacccc tttcacggcc tccagcatag agttggtgcc   1320
acagagttcc acaacaacat cagccttaca tctgtcattg tatccagcca aggagaagaa   1380
gttcccgggg ctgccgggtc tggaagagca actggagtgt gatggaatgt ctgagcctgg   1440
tcactggtgc ataatcccct ggcagctgg ccaagcggtc tcagcctaca gtgaggagag   1500
agaccggcca tatggtctgg tgtccattga cacagtgact gtgggagatg cagagggcct   1560
```

-continued

```
gtgtgtctgg ccctgtagct gtgaggatga tggctatcca gccatgaacc tggatgctgg    1620
ccgagagtct ggccctaatt cagaggatct gctcttggtc acagaccctg cttttctgtc    1680
ttgcggctgt gtctcaggta gtggtctcag gcttggaggc tccccaggca gcctactgga    1740
caggttgagg ctgtcatttg caaaggaagg ggactggaca gcagacccaa cctggagaac    1800
tgggtcccca ggaggggggct ctgagagtga agcaggttcc cccctggtc tggacatgga     1860 cacatttgac agtggctttg caggttcaga ctgtggcagc cccgtggaga ctgatgaagg    1920
accccctcga agctatctcc gccagtgggt ggtcaggacc cctccacctg tggacagtgg    1980
agcccagagc agctagcata taataaccag ctatagtgag aagaggcctc tgagcctggc    2040
atttacagtg tgaacatgta ggggtgtgtg tgtgtgtgtg tgtgtgtgtg tgtgtgtgtg    2100
tgtgtgtgtg tgtgtgtgtg tgtcttgggt tgtgtgttag cacatccatg ttgggatttg    2160
gtctgttgct atgtattgta atgctaaatt ctctacccaa agttctaggc ctacgagtga    2220
attctcatgt ttacaaactt gctgtgtaaa ccttgttcct taatttaata ccattggtta    2280
aataaaattg gctgcaacca attactggag ggattagagg taggggggctt ttgagttacc    2340 tgtttggaga tggagaagga gagaggagag accaagagga gaaggaggaa ggagaggaga    2400
ggagaggaga ggagaggaga ggagaggaga ggagaggaga ggagaggaga ggctgccgtg    2460
aggggagagg gaccatgagc ctgtggccag gagaaacagc aagtatctgg ggtacactgg    2520
tgaggaggtg gccaggccag cagttagaag agtagattag gggtgacctc cagtatttgt    2580
caaagccaat taaataaca aaaaaaaaaa aaaagcggcc gctctaga                  2628
```

<210> SEQ ID NO 10
<211> LENGTH: 529
<212> TYPE: PRT
<213> ORGANISM: Mouse

<400> SEQUENCE: 10

```
Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
```

```
                180             185             190
Asp Ser Ser Tyr Gln Leu Gln Val Arg Ala Ala Pro Gln Pro Gly Thr
        195                 200                 205
Ser Phe Arg Gly Thr Trp Ser Glu Trp Ser Asp Pro Val Ile Phe Gln
    210                 215                 220
Thr Gln Ala Gly Glu Pro Glu Ala Gly Trp Asp Pro His Met Leu Leu
225                 230                 235                 240
Leu Leu Ala Val Leu Ile Ile Val Leu Val Phe Met Gly Leu Lys Ile
                245                 250                 255
His Leu Pro Trp Arg Leu Trp Lys Lys Ile Trp Ala Pro Val Pro Thr
            260                 265                 270
Pro Glu Ser Phe Phe Gln Pro Leu Tyr Arg Glu His Ser Gly Asn Phe
        275                 280                 285
Lys Lys Trp Val Asn Thr Pro Phe Thr Ala Ser Ser Ile Glu Leu Val
    290                 295                 300
Pro Gln Ser Ser Thr Thr Thr Ser Ala Leu His Leu Ser Leu Tyr Pro
305                 310                 315                 320
Ala Lys Glu Lys Lys Phe Pro Gly Leu Pro Gly Leu Glu Glu Gln Leu
                325                 330                 335
Glu Cys Asp Gly Met Ser Glu Pro Gly His Trp Cys Ile Ile Pro Leu
            340                 345                 350
Ala Ala Gly Gln Ala Val Ser Ala Tyr Ser Glu Glu Arg Asp Arg Pro
        355                 360                 365
Tyr Gly Leu Val Ser Ile Asp Thr Val Thr Val Gly Asp Ala Glu Gly
    370                 375                 380
Leu Cys Val Trp Pro Cys Ser Cys Glu Asp Asp Gly Tyr Pro Ala Met
385                 390                 395                 400
Asn Leu Asp Ala Gly Arg Glu Ser Gly Pro Asn Ser Glu Asp Leu Leu
                405                 410                 415
Leu Val Thr Asp Pro Ala Phe Leu Ser Cys Gly Cys Val Ser Gly Ser
            420                 425                 430
Gly Leu Arg Leu Gly Gly Ser Pro Gly Ser Leu Leu Asp Arg Leu Arg
        435                 440                 445
Leu Ser Phe Ala Lys Glu Gly Asp Trp Thr Ala Asp Pro Thr Trp Arg
    450                 455                 460
Thr Gly Ser Pro Gly Gly Gly Ser Glu Ser Glu Ala Gly Ser Pro Pro
465                 470                 475                 480
Gly Leu Asp Met Asp Thr Phe Asp Ser Gly Phe Ala Gly Ser Asp Cys
                485                 490                 495
Gly Ser Pro Val Glu Thr Asp Glu Gly Pro Pro Arg Ser Tyr Leu Arg
            500                 505                 510
Gln Trp Val Val Arg Thr Pro Pro Val Asp Ser Gly Ala Gln Ser
        515                 520                 525
Ser
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 11
agcatcaagc cggctccccc                                          20

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 12
ctccattcac tccaggtccc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 13
ttgaacgtga ctgrggcctt                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Murine
      MU-1 cDNA Internal Oligonucleotide

<400> SEQUENCE: 14
tgaatgaagt gcctggctga                                              20

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: 5' PCR
      Primer

<400> SEQUENCE: 15
cacaaagctt cagtatgagc tgcagtacag gaaccgggga                        40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: 3' PCR
      primer

<400> SEQUENCE: 16
cacaggatcc ctttaactcc tctgactggg tctgaaagat                        40

<210> SEQ ID NO 17
<211> LENGTH: 224
<212> TYPE: PRT
<213> ORGANISM: Unknown Organism
<220> FEATURE:
<221> NAME/KEY: UnknownOrganism
<222> LOCATION: (1)..(224)
<223> OTHER INFORMATION: Description of Unknown Organism: Second
      polypeptide comprising an Fc region

<400> SEQUENCE: 17

His Thr Cys Pro Pro Cys Pro Ala Pro Glu Ala Leu Gly Ala Pro Ser
1               5                   10                  15
```

```
Val Phe Leu Phe Pro Pro Lys Pro Lys Asp Thr Leu Met Ile Ser Arg
             20                  25                  30

Thr Pro Glu Val Thr Cys Val Val Asp Val Ser His Glu Asp Pro
         35                  40                  45

Glu Val Lys Phe Asn Trp Tyr Val Asp Gly Val Glu Val His Asn Ala
 50                  55                  60

Lys Thr Lys Pro Arg Glu Glu Gln Tyr Asn Ser Thr Tyr Arg Val Val
 65                  70                  75                  80

Ser Val Leu Thr Val Leu His Gln Asp Trp Leu Asn Gly Lys Glu Tyr
             85                  90                  95

Lys Cys Lys Val Ser Asn Lys Ala Leu Pro Val Pro Ile Glu Lys Thr
            100                 105                 110

Ile Ser Lys Ala Lys Gly Gln Pro Arg Glu Pro Gln Val Tyr Thr Leu
            115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly Lys
    210                 215                 220

<210> SEQ ID NO 18
<211> LENGTH: 617
<212> TYPE: DNA
<213> ORGANISM: Human

<400> SEQUENCE: 18
gctgaagtga aaacgagacc aaggtctagc tctactgttg gtacttatga gatccagtcc      60
tggcaacatg gagaggattg tcatctgtct gatggtcatc ttcttgggga cactggtcca     120
caaatcaagc tcccaaggtc aagatcgcca catgattaga atgcgtcaac ttatagatat     180
tgttgatcag ctgaaaaatt atgtgaatga cttggtccct gaatttctgc cagctccaga     240
agatgtagag acaaactgtg agtggtcagc ttttcctgc tttcagaagg cccaactaaa      300
gtcagcaaat acaggaaaca atgaaaggat aatcaatgta tcaattaaaa agctgaagag     360
gaaaccacct tccacaaatg cagggagaag acagaaacac agactaacat gcccttcatg     420
tgattcttat gagaaaaaac cacccaaaga attcctagaa agattcaaat cacttctcca     480
aaagatgatt catcagcatc tgtcctctag aacacacgga agtgaagatt cctgaggatc     540
taacttgcag ttggacacta tgttacatac tctaatatag tagtgaaagt catttctttg     600
tattccaagt ggaggag                                                    617

<210> SEQ ID NO 19
<211> LENGTH: 162
<212> TYPE: PRT
<213> ORGANISM: Human

<400> SEQUENCE: 19

Met Arg Ser Ser Pro Gly Asn Met Glu Arg Ile Val Ile Cys Leu Met
 1               5                  10                  15
```

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
            35                  40                  45

Leu Lys Asn Tyr Val Asn Asp Leu Val Pro Glu Phe Leu Pro Ala Pro
        50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
            115                 120                 125

Glu Lys Lys Pro Pro Lys Glu Phe Leu Glu Arg Phe Lys Ser Leu Leu
        130                 135                 140

Gln Lys Met Ile His Gln His Leu Ser Ser Arg Thr His Gly Ser Glu
145                 150                 155                 160

Asp Ser

<210> SEQ ID NO 20
<211> LENGTH: 7
<212> TYPE: PRT
<213> ORGANISM: Human

<400> SEQUENCE: 20

Glu Asp Asp Gly Tyr Pro Ala
1               5

<210> SEQ ID NO 21
<211> LENGTH: 16
<212> TYPE: PRT
<213> ORGANISM: Human

<400> SEQUENCE: 21

Met Pro Leu Leu Leu Leu Leu Leu Leu Pro Ser Pro Leu His Pro
1               5                   10                  15

<210> SEQ ID NO 22
<211> LENGTH: 786
<212> TYPE: DNA
<213> ORGANISM: Human

<400> SEQUENCE: 22
atgaaattct tagtcaacgt tgcccttgtt tttatggtcg tgtacatttc ttacatctat     60
gccggcagcg gacaccacca tcatcaccac ggtagcggcg actataaaga cgatgacgat    120
aagggttccg gatgccccga cctcgtctgc tacaccgatt acctccagac ggtcatctgc    180
atcctggaaa tgtggaacct ccaccccagc acgctcaccc ttacctggca agaccagtat    240
gaagagctga aggacgaggc cacctcctgc agcctccaca gtcggcccca caatgccacg    300
catgccacct acacctgcca catggatgta ttccacttca tggccgacga cattttcagt    360
gtcaacatca cagaccagtc tggcaactac tcccaggagt gtggcagctt ctctcctggct    420 gagagcatca agccggctcc ccctttcaac gtgactgtga ccttctcagg acagtataat    480
atctcctggc gctcagatta cgaagaccct gccttctaca tgctgaaggg caagcttcag    540
tatgagctgc agtacaggaa ccggggagac ccctgggctg tgagtccgag agaaagctg    600

```
atctcagtgg actcaagaag tgtctccctc ctcccctgg agttccgcaa agactcgagc    660
tatgagctgc aggtgcgggc agggcccatg cctggctcct cctaccaggg gacctggagt    720
gaatggagtg acccggtcat ctttcagacc cagtcagagg agttaaagga aggctggaac    780
taatga                                                                786
```

<210> SEQ ID NO 23
<211> LENGTH: 260
<212> TYPE: PRT
<213> ORGANISM: Human

<400> SEQUENCE: 23

```
Met Lys Phe Leu Val Asn Val Ala Leu Val Phe Met Val Val Tyr Ile
 1               5                  10                  15

Ser Tyr Ile Tyr Ala Gly Ser Gly His His His His His His Gly Ser
            20                  25                  30

Gly Asp Tyr Lys Asp Asp Asp Asp Lys Gly Ser Gly Cys Pro Asp Leu
        35                  40                  45

Val Cys Tyr Thr Asp Tyr Leu Gln Thr Val Ile Cys Ile Leu Glu Met
50                  55                  60

Trp Asn Leu His Pro Ser Thr Leu Thr Leu Thr Trp Gln Asp Gln Tyr
65                  70                  75                  80

Glu Glu Leu Lys Asp Glu Ala Thr Ser Cys Ser Leu His Arg Ser Ala
                85                  90                  95

His Asn Ala Thr His Ala Thr Tyr Thr Cys His Met Asp Val Phe His
            100                 105                 110

Phe Met Ala Asp Asp Ile Phe Ser Val Asn Ile Thr Asp Gln Ser Gly
        115                 120                 125

Asn Tyr Ser Gln Glu Cys Gly Ser Phe Leu Leu Ala Glu Ser Ile Lys
130                 135                 140

Pro Ala Pro Pro Phe Asn Val Thr Val Thr Phe Ser Gly Gln Tyr Asn
145                 150                 155                 160

Ile Ser Trp Arg Ser Asp Tyr Glu Asp Pro Ala Phe Tyr Met Leu Lys
                165                 170                 175

Gly Lys Leu Gln Tyr Glu Leu Gln Tyr Arg Asn Arg Gly Asp Pro Trp
            180                 185                 190

Ala Val Ser Pro Arg Arg Lys Leu Ile Ser Val Asp Ser Arg Ser Val
        195                 200                 205

Ser Leu Leu Pro Leu Glu Phe Arg Lys Asp Ser Ser Tyr Glu Leu Gln
210                 215                 220

Val Arg Ala Gly Pro Met Pro Gly Ser Ser Tyr Gln Gly Thr Trp Ser
225                 230                 235                 240

Glu Trp Ser Asp Pro Val Ile Phe Gln Thr Gln Ser Glu Glu Leu Lys
                245                 250                 255

Glu Gly Trp Asn
            260
```

<210> SEQ ID NO 24
<211> LENGTH: 1426
<212> TYPE: DNA
<213> ORGANISM: Human

<400> SEQUENCE: 24

```
gcggccgcac caccatgccg cgtggctggg ccgcccctt gctcctgctg ctgctccagg    60
gaggctgggg ctgccccgac ctcgtctgct acaccgatta cctccagacg gtcatctgca    120
```

```
tcctggaaat gtggaacctc cacccccagca cgctcaccct tacctggcaa gaccagtatg    180
aagagctgaa ggacgaggcc acctcctgca gcctccacag gtcggcccac aatgccacgc    240
atgccaccta cacctgccac atggatgtat tccacttcat ggccgacgac attttcagtg    300
tcaacatcac agaccagtct ggcaactact cccaggagtg tggcagcttt ctcctggctg    360
agagcatcaa gccggctccc cctttcaacg tgactgtgac cttctcagga cagtataata    420
tctcctggcg ctcagattac gaagaccctg ccttctacat gctgaagggc aagcttcagt    480
atgagctgca gtacaggaac cggggagacc cctgggctgt gagtccgagg agaaagctga    540
tctcagtgga ctcaagaagt gtctccctcc tccccctgga gttccgcaaa gactcgagct    600
atgagctgca ggtgcgggca gggcccatgc ctggctcctc ctaccagggg acctggagtg    660
aatggagtga cccggtcatc tttcagaccc agtcagagga gttaaaggaa ggctggaacg    720
gctccggctc tagagacaaa actcacacat gcccaccgtg cccagcacct gaactcctgg    780
ggggaccgtc agtcttcctc ttccccccaa aacccaagga caccctcatg atctcccgga    840
cccctgaggt cacatgcgtg gtggtggacg tgagccacga agaccctgag gtcaagttca    900
actggtacgt ggacggcgtg gaggtgcata atgccaagac aaagccgcgg gaggagcagt    960
acaacagcac gtaccgtgtg gtcagcgtcc tcaccgtcct gcaccaggac tggctgaatg   1020
gcaaggagta caagtgcaag gtctccaaca aagccctccc agtccccatc gagaaaacca   1080
tctccaaagc caaagggcag ccccgagaac acaggtgta ccctgccc ccatcccggg   1140 aggagatgac caagaaccag gtcagcctga cctgcctggt caaaggcttc tatcccagcg   1200
acatcgccgt ggagtgggag agcaatgggc agccggagaa caactacaag accacgcctc   1260
ccgtgctgga ctccgacggc tccttcttcc tctatagcaa gctcaccgtg gacaagagca   1320
ggtggcagca ggggaacgtc ttctcatgct ccgtgatgca tgaggctctg cacaaccact   1380
acacgcagaa gagcctctcc ctgtccccgg gtaaatgagt gaattc               1426
```

<210> SEQ ID NO 25
<211> LENGTH: 467
<212> TYPE: PRT
<213> ORGANISM: Human

<400> SEQUENCE: 25

```
Met Pro Arg Gly Trp Ala Ala Pro Leu Leu Leu Leu Leu Leu Gln Gly
  1               5                  10                  15

Gly Trp Gly Cys Pro Asp Leu Val Cys Tyr Thr Asp Tyr Leu Gln Thr
             20                  25                  30

Val Ile Cys Ile Leu Glu Met Trp Asn Leu His Pro Ser Thr Leu Thr
         35                  40                  45

Leu Thr Trp Gln Asp Gln Tyr Glu Glu Leu Lys Asp Glu Ala Thr Ser
     50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Asp Ile Phe Ser Val
                 85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140
```

```
Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
            165                 170                 175

Ser Val Asp Ser Arg Ser Val Ser Leu Leu Pro Leu Glu Phe Arg Lys
        180                 185                 190

Asp Ser Ser Tyr Glu Leu Gln Val Arg Ala Gly Pro Met Pro Gly Ser
    195                 200                 205

Ser Tyr Gln Gly Thr Trp Ser Glu Trp Ser Asp Pro Val Ile Phe Gln
210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
        260                 265                 270

Ile Ser Arg Thr Pro Glu Val Thr Cys Val Val Val Asp Val Ser His
    275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Val Pro Ile
        340                 345                 350

Glu Lys Thr Ile Ser Lys Ala Lys Gly Gln Pro Arg Glu Pro Gln Val
    355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
        420                 425                 430

Asp Lys Ser Arg Trp Gln Gln Gly Asn Val Phe Ser Cys Ser Val Met
    435                 440                 445

His Glu Ala Leu His Asn His Tyr Thr Gln Lys Ser Leu Ser Leu Ser
450                 455                 460

Pro Gly Lys
465

<210> SEQ ID NO 26
<211> LENGTH: 1499
<212> TYPE: DNA
<213> ORGANISM: Human

<400> SEQUENCE: 26
gcggccgcac caccatgccg cgtggctggg ccgccccctt gctcctgctg ctgctccagg      60
gaggctgggg ctgccccgac ctcgtctgct acaccgatta cctccagacg gtcatctgca     120
tcctggaaat gtggaacctc caccccagca cgctcaccct tacctggcaa gaccagtatg     180
aagagctgaa ggacgaggcc acctcctgca gcctccacag gtcggcccac aatgccacgc     240
```

-continued

```
atgccaccta cacctgccac atggatgtat tccacttcat ggccgacgac attttcagtg      300
tcaacatcac agaccagtct ggcaactact cccaggagtg tggcagcttt ctcctggctg      360
agagcatcaa gccggctccc cctttcaacg tgactgtgac cttctcagga cagtataata     420
tctcctggcg ctcagattac gaagaccctg ccttctacat gctgaagggc aagcttcagt     480
atgagctgca gtacaggaac cggggagacc cctgggctgt gagtccgagg agaaagctga     540
tctcagtgga ctcaagaagt gtctccctcc tccccctgga gttccgcaaa gactcgagct     600
atgagctgca ggtgcgggca gggcccatgc ctggctcctc ctaccagggg acctggagtg     660
aatggagtga cccggtcatc tttcagaccc agtcagagga gttaaaggaa ggctggaacg     720
gctccggctc tagagacaaa actcacacat gcccaccgtg cccagcacct gaactcctgg     780
ggggaccgtc agtcttcctc ttccccccaa acccaagga caccctcatg atctcccgga     840
cccctgaggt cacatgcgtg gtggtggacg tgagccacga agaccctgag gtcaagttca     900
actggtacgt ggacggcgtg gaggtgcata atgccaagac aaagccgcgg gaggagcagt     960
acaacagcac gtaccgtgtg gtcagcgtcc tcaccgtcct gcaccaggac tggctgaatg    1020
gcaaggagta caagtgcaag gtctccaaca aagccctccc agtccccatc gagaaaacca    1080
tctccaaagc caaagggcag ccccgagaac acaggtgta caccctgccc ccatcccggg    1140
aggagatgac caagaaccag gtcagcctga cctgcctggt caaaggcttc tatcccagcg    1200
acatcgccgt ggagtgggag agcaatgggc agccggagaa caactacaag accacgcctc    1260
ccgtgctgga ctccgacggc tccttcttcc tctatagcaa gctcaccgtg gacaagagca    1320
ggtggcagca ggggaacgtc ttctcatgct ccgtgatgca tgaggctctg cacaaccact    1380
acacgcagaa gagcctctcc ctgtccccgg gtaaatcagg aatggcatca atgacaggag    1440
gtcaacaaat gggttctgga tctcatcatc atcatcatca ttctggaggt tgagaattc     1499
```

```
<210> SEQ ID NO 27
<211> LENGTH: 492
<212> TYPE: PRT
<213> ORGANISM: Human

<400> SEQUENCE: 27
```

```
Met Pro Arg Gly Trp Ala Ala Pro Leu Leu Leu Leu Leu Gln Gly
 1               5                  10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
             35                  40                  45

Leu Thr Trp Gln Asp Gln Tyr Glu Glu Leu Lys Asp Glu Ala Thr Ser
     50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Ile Phe Ser Val
                 85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Phe Asn Val Thr Val
         115                 120                 125

Thr Phe Ser Gly Gln Tyr Asn Ile Ser Trp Arg Ser Asp Tyr Glu Asp
     130                 135                 140

Pro Ala Phe Tyr Met Leu Lys Gly Lys Leu Gln Tyr Glu Leu Gln Tyr
```

```
            145                 150                 155                 160
Arg Asn Arg Gly Asp Pro Trp Ala Val Ser Pro Arg Lys Leu Ile
                165                 170                 175
Ser Val Asp Ser Arg Val Ser Leu Leu Pro Leu Glu Phe Arg Lys
                180                 185                 190
Asp Ser Ser Tyr Glu Leu Gln Val Arg Ala Gly Pro Met Pro Gly Ser
                195                 200                 205
Ser Tyr Gln Gly Thr Trp Ser Glu Trp Ser Asp Pro Val Ile Phe Gln
                210                 215                 220
Thr Gln Ser Glu Glu Leu Lys Glu Gly Trp Asn Gly Ser Gly Ser Arg
225                 230                 235                 240
Asp Lys Thr His Thr Cys Pro Pro Cys Pro Ala Pro Glu Leu Leu Gly
                245                 250                 255
Gly Pro Ser Val Phe Leu Phe Pro Pro Lys Pro Lys Asp Thr Leu Met
                260                 265                 270
Ile Ser Arg Thr Pro Glu Val Thr Cys Val Val Val Asp Val Ser His
                275                 280                 285
Glu Asp Pro Glu Val Lys Phe Asn Trp Tyr Val Asp Gly Val Glu Val
                290                 295                 300
His Asn Ala Lys Thr Lys Pro Arg Glu Glu Gln Tyr Asn Ser Thr Tyr
305                 310                 315                 320
Arg Val Val Ser Val Leu Thr Val Leu His Gln Asp Trp Leu Asn Gly
                325                 330                 335
Lys Glu Tyr Lys Cys Lys Val Ser Asn Lys Ala Leu Pro Val Pro Ile
                340                 345                 350
Glu Lys Thr Ile Ser Lys Ala Lys Gly Gln Pro Arg Glu Pro Gln Val
                355                 360                 365
Tyr Thr Leu Pro Pro Ser Arg Glu Glu Met Thr Lys Asn Gln Val Ser
                370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
                405                 410                 415
Val Leu Asp Ser Asp Gly Ser Phe Phe Leu Tyr Ser Lys Leu Thr Val
                420                 425                 430
Asp Lys Ser Arg Trp Gln Gln Gly Asn Val Phe Ser Cys Ser Val Met
                435                 440                 445
His Glu Ala Leu His Asn His Tyr Thr Gln Lys Ser Leu Ser Leu Ser
                450                 455                 460
Pro Gly Lys Ser Gly Met Ala Ser Met Thr Gly Gly Gln Gln Met Gly
465                 470                 475                 480
Ser Gly Ser His His His His His His Ser Gly Gly
                485                 490
```

<210> SEQ ID NO 28
<211> LENGTH: 1426
<212> TYPE: DNA
<213> ORGANISM: Human

<400> SEQUENCE: 28

```
gcggccgcac caccatgccg cgtggctggg ccgccccctt gctcctgctg ctgctccagg    60
gaggctgggg ctgccccgac ctcgtctgct acaccgatta cctccagacg gtcatctgca   120
tcctggaaat gtggaacctc caccccagca cgctcaccct tacctggcaa gaccagtatg   180
```

```
aagagctgaa ggacgaggcc acctcctgca gcctccacag gtcggcccac aatgccacgc    240
atgccaccta cacctgccac atggatgtat tccacttcat ggccgacgac attttcagtg    300
tcaacatcac agaccagtct ggcaactact cccaggagtg tggcagcttt ctcctggctg    360
agagcatcaa gccggctccc ccttttcaacg tgactgtgac cttctcagga cagtataata   420
tctcctggcg ctcagattac gaagaccctg ccttctacat gctgaagggc aagcttcagt    480
atgagctgca gtacaggaac cggggagacc cctgggctgt gagtccgagg agaaagctga    540
tctcagtgga ctcaagaagt gtctccctcc tcccctgga gttccgcaaa gactcgagct     600
atgagctgca ggtgcgggca gggcccatgc ctggctcctc ctaccagggg acctggagtg    660
aatggagtga cccggtcatc tttcagaccc agtcagagga gttaaaggaa ggctggaacg    720
gctccggctc tagagacaaa actcacacat gccaccgtg cccagcacct gaagccctgg     780
gggcaccgtc agtcttcctc ttcccccaa aacccaagga caccctcatg atctcccgga    840
cccctgaggt cacatgcgtg gtggtggacg tgagccacga agaccctgag gtcaagttca    900
actggtacgt ggacggcgtg gaggtgcata atgccaagac aaagccgcgg gaggagcagt    960
acaacagcac gtaccgtgtg gtcagcgtcc tcaccgtcct gcaccaggac tggctgaatg   1020
gcaaggagta caagtgcaag gtctccaaca agcccctccc agcccccatc gagaaaacca   1080
tctccaaagc caaagggcag ccccgagaac acaggtgta caccctgccc ccatcccggg    1140
aggagatgac caagaaccag gtcagcctga cctgcctggt caaaggcttc tatcccagcg   1200
acatcgccgt ggagtgggag agcaatgggc agccggagaa caactacaag accacgcctc   1260
ccgtgctgga ctccgacggc tccttcttcc tctatagcaa gctcaccgtg gacaagagca   1320
ggtggcagca ggggaacgtc ttctcatgct ccgtgatgca tgaggctctg cacaaccact   1380
acacgcagaa gagcctctcc ctgtccccgg gtaaatgagt gaattc                  1426
```

<210> SEQ ID NO 29
<211> LENGTH: 467
<212> TYPE: PRT
<213> ORGANISM: Human

<400> SEQUENCE: 29

```
Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
            20                  25                  30

Val Ile Cys Ile Leu Glu Met Trp Asn Leu His Pro Ser Thr Leu Thr
        35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Asp Ile Phe Ser Val
                85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160
```

```
Arg Asn Arg Gly Asp Pro Trp Ala Val Ser Pro Arg Lys Leu Ile
            165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
            195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Gly Ser Gly Ser Arg
225                 230                 235                 240

Asp Lys Thr His Thr Cys Pro Pro Cys Pro Ala Pro Glu Ala Leu Gly
                245                 250                 255

Ala Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys
465

<210> SEQ ID NO 30
<211> LENGTH: 741
<212> TYPE: DNA
<213> ORGANISM: Human

<400> SEQUENCE: 30
atgccgcgtg gctgggccgc ccccttgctc ctgctgctgc tccagggagg ctggggctgc     60
cccgacctcg tctgctacac cgattacctc cagacggtca tctgcatcct ggaaatgtgg    120
aacctccacc ccagcacgct caccctaacc tggcaagacc agtatgaaga gctgaaggac    180
gaggccacct cctgcagcct ccacaggtcg gcccacaatg ccacgcatgc cacctacacc    240
tgccacatgg atgtattcca cttcatggcc gacgacattt tcagtgtcaa catcacagac    300
```

-continued

```
cagtctggca actactccca ggagtgtggc agctttctcc tggctgagag catcaagccg    360
gctccccctt tcaacgtgac tgtgaccttc tcaggacagt ataatatctc ctggcgctca    420
gattacgaag accctgcctt ctacatgctg aagggcaagc ttcagtatga gctgcagtac    480
aggaaccggg gagacccctg ggctgtgagt ccgaggagaa agctgatctc agtggactca    540
agaagtgtct ccctcctccc cctggagttc gcaaagact cgagctatga gctgcaggtg     600
cgggcagggc ccatgcctgg ctcctcctac caggggacct ggagtgaatg gagtgacccg    660
gtcatctttc agacccagtc agaggagtta aaggaaggct ggaacaaaac cgaaacctcc    720
caggttgctc cggcataatg a                                              741
```

<210> SEQ ID NO 31
<211> LENGTH: 245
<212> TYPE: PRT
<213> ORGANISM: Human

<400> SEQUENCE: 31

```
Met Pro Arg Gly Trp Ala Ala Pro Leu Leu Leu Leu Leu Gln Gly
1               5                   10                  15
Gly Trp Gly Cys Pro Asp Leu Val Cys Tyr Thr Asp Tyr Leu Gln Thr
            20                  25                  30
Val Ile Cys Ile Leu Glu Met Trp Asn Leu His Pro Ser Thr Leu Thr
        35                  40                  45
Leu Thr Trp Gln Asp Gln Tyr Glu Glu Leu Lys Asp Glu Ala Thr Ser
    50                  55                  60
Cys Ser Leu His Arg Ser Ala His Asn Ala Thr His Ala Thr Tyr Thr
65                  70                  75                  80
Cys His Met Asp Val Phe His Phe Met Ala Asp Asp Ile Phe Ser Val
                85                  90                  95
Asn Ile Thr Asp Gln Ser Gly Asn Tyr Ser Gln Glu Cys Gly Ser Phe
            100                 105                 110
Leu Leu Ala Glu Ser Ile Lys Pro Ala Pro Pro Phe Asn Val Thr Val
        115                 120                 125
Thr Phe Ser Gly Gln Tyr Asn Ile Ser Trp Arg Ser Asp Tyr Glu Asp
    130                 135                 140
Pro Ala Phe Tyr Met Leu Lys Gly Lys Leu Gln Tyr Glu Leu Gln Tyr
145                 150                 155                 160
Arg Asn Arg Gly Asp Pro Trp Ala Val Ser Pro Arg Arg Lys Leu Ile
                165                 170                 175
Ser Val Asp Ser Arg Ser Val Ser Leu Leu Pro Leu Glu Phe Arg Lys
            180                 185                 190
Asp Ser Ser Tyr Glu Leu Gln Val Arg Ala Gly Pro Met Pro Gly Ser
        195                 200                 205
Ser Tyr Gln Gly Thr Trp Ser Glu Trp Ser Asp Pro Val Ile Phe Gln
    210                 215                 220
Thr Gln Ser Glu Glu Leu Lys Glu Gly Trp Asn Lys Thr Glu Thr Ser
225                 230                 235                 240
Gln Val Ala Pro Ala
                245
```

<210> SEQ ID NO 32
<211> LENGTH: 1413
<212> TYPE: DNA
<213> ORGANISM: Human

<400> SEQUENCE: 32

-continued

```
atgccgcgtg gctgggccgc ccccttgctc ctgctgctgc tccagggagg ctggggctgc    60
cccgacctcg tctgctacac cgattacctc cagacggtca tctgcatcct ggaaatgtgg   120
aacctccacc ccagcacgct caccttacc tggcaagacc agtatgaaga gctgaaggac   180
gaggccacct cctgcagcct ccacaggtcg gcccacaatg ccacgcatgc cacctacacc   240
tgccacatgg atgtattcca cttcatggcc gacgacattt tcagtgtcaa catcacagac   300
cagtctggca actactccca ggagtgtggc agctttctcc tggctgagag catcaagccg   360
gctccccctt tcaacgtgac tgtgaccttc tcaggacagt ataatatctc ctggcgctca   420
gattacgaag accctgcctt ctacatgctg aagggcaagc ttcagtatga gctgcagtac   480
aggaaccggg gagacccctg ggctgtgagt ccgaggagaa agctgatctc agtggactca   540
agaagtgtct ccctcctccc cctggagttc cgcaaagact cgagctatga gctgcaggtg   600
cgggcagggc ccatgcctgg ctcctcctac caggggacct ggagtgaatg gagtgacccg   660
gtcatctttc agacccagtc agaggagtta aggaaggct ggaacgatga cgatgacaag   720
ggctccggcg acaaaactca cacatgccca ccgtgcccag cacctgaagc cctgggggca   780
ccgtcagtct tcctcttccc cccaaaaccc aaggacaccc tcatgatctc ccggacccct   840
gaggtcacat gcgtggtggt ggacgtgagc cacgaagacc ctgaggtcaa gttcaactgg   900
tacgtggacg gcgtggaggt gcataatgcc aagacaaagc cgcgggagga gcagtacaac   960
agcacgtacc gtgtggtcag cgtcctcacc gtcctgcacc aggactggct gaatggcaag  1020
gagtacaagt gcaaggtctc caacaaagcc ctcccagccc ccatcgagaa aaccatctcc  1080
aaagccaaag ggcagccccg agaaccacag gtgtacaccc tgcccccatc ccgggaggag  1140
atgaccaaga accaggtcag cctgacctgc ctggtcaaag gcttctatcc agcgacatc  1200
gccgtggagt gggagagcaa tgggcagccg gagaacaact acaagaccac gcctcccgtg  1260
ctggactccg acggctcctt cttcctctat agcaagctca ccgtggacaa gagcaggtgg  1320
cagcagggga acgtcttctc atgctccgtg atgcatgagg ctctgcacaa ccactacacg  1380
cagaagagcc tctccctgtc cccgggtaaa tga                              1413
```

<210> SEQ ID NO 33
<211> LENGTH: 470
<212> TYPE: PRT
<213> ORGANISM: Human

<400> SEQUENCE: 33

```
Met Pro Arg Gly Trp Ala Ala Pro Leu Leu Leu Leu Leu Leu Gln Gly
1               5                   10                  15
Gly Trp Gly Cys Pro Asp Leu Val Cys Tyr Thr Asp Tyr Leu Gln Thr
            20                  25                  30
Val Ile Cys Ile Leu Glu Met Trp Asn Leu His Pro Ser Thr Leu Thr
        35                  40                  45
Leu Thr Trp Gln Asp Gln Tyr Glu Glu Leu Lys Asp Glu Ala Thr Ser
    50                  55                  60
Cys Ser Leu His Arg Ser Ala His Asn Ala Thr His Ala Thr Tyr Thr
65                  70                  75                  80
Cys His Met Asp Val Phe His Phe Met Ala Asp Asp Ile Phe Ser Val
                85                  90                  95
Asn Ile Thr Asp Gln Ser Gly Asn Tyr Ser Gln Glu Cys Gly Ser Phe
            100                 105                 110
Leu Leu Ala Glu Ser Ile Lys Pro Ala Pro Pro Phe Asn Val Thr Val
```

```
                 115                 120                 125
Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Lys Leu Ile
                165                 170                 175

Ser Val Asp Ser Arg Ser Val Ser Leu Leu Pro Leu Glu Phe Arg Lys
                180                 185                 190

Asp Ser Ser Tyr Glu Leu Gln Val Arg Ala Gly Pro Met Pro Gly Ser
                195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Asp Asp Asp Lys
225                 230                 235                 240

Gly Ser Gly Asp Lys Thr His Thr Cys Pro Pro Cys Pro Ala Pro Glu
                245                 250                 255

Ala Leu Gly Ala Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 34
<211> LENGTH: 1754
<212> TYPE: DNA
<213> ORGANISM: Mouse

<400> SEQUENCE: 34
atgccccggg gcccagtggc tgccttactc ctgctgattc tccatggagc ttggagctgc      60
ctggacctca cttgctacac tgactacctc tggaccatca cctgtgtcct ggagacacgg     120
```

-continued

```
agccccaacc ccagcatact cagtctcacc tggcaagatg aatatgagga acttcaggac      180
caagagacct tctgcagcct acacaggtct ggccacaaca ccacacatat atggtacacg      240
tgccatatgc gcttgtctca attcctgtcc gatgaagttt tcattgtcaa tgtgacggac      300
cagtctggca caactccca agagtgtggc agctttgtcc tggctgagag catcaaacca      360
gctcccccct gaacgtgac tgtggccttc tcaggacgct atgatatctc ctggactca       420 gcttatgacg aaccctccaa ctacgtgctg aggggcaagc tacaatatga gctgcagtat    480
cggaacctca gagaccccta tgctgtgagg ccggtgacca agctgatctc agtggactca    540
agaaacgtct ctcttctccc tgaagagttc cacaaagatt ctagctacca gctgcaggtg    600
cgggcagcgc ctcagccagg cacttcattc agggggacct ggagtgagtg gagtgacccc    660
gtcatctttc agacccaggc tggggagccc gaggcaggct gggacggctc cggctctaga    720
gagccccgcg gaccgacaat caagccctgt cctccatgca aatgcccagg taagtcacta    780
gaccagagct ccactcccgg gagaatggta agtgctataa acatccctgc actagaggat    840
aagccatgta cagatccatt tccatctctc ctcatcagca cctaacctcg agggtggacc    900
atccgtcttc atcttccctc caaagatcaa ggatgtactc atgatctccc tgagccccat    960
agtcacatgt gtggtggtgg atgtgagcga ggatgaccca gatgtccaga tcagctggtt    1020
tgtgaacaac gtggaagtac acacagctca gacacaaacc catagagagg attacaacag    1080
tactctccgg gtggtcagtg ccctcccccat ccagcaccag gactggatga gtggcaaggc    1140
tttcgcatgc gccgtcaaca caaagacct cccagcgccc atcgagagaa ccatctcaaa     1200
acccaaaggt gagagctgca gcctgactgc atggggctg ggatgggcat aaggataaag     1260
gtctgtgtgg acagccttct gcttcagcca tgaccttgt gtatgtttct accctcacag     1320
ggtcagtaag agctccacag gtatatgtct tgcctccacc agaagaagag atgactaaga    1380
aacaggtcac tctgacctgc atggtcacag acttcatgcc tgaagacatt tacgtggagt    1440
ggaccaacaa cgggaaaaca gagctaaact acaagaacac tgaaccagtc ctggactctg    1500
atggttctta cttcatgtac agcaagctga gagtggaaaa aagaactgg gtggaaagaa    1560 atagctactc ctgttcagtg gtccacgagg gtctgcacaa tcaccacacg actaagagct    1620
tctcccggac tccgggtaaa tgagctcagc acccacaaaa ctctcaggtc caaagagaca    1680
cccacactca tctccatgct tcccttgtat aaataaagca cccagcaatg cctgggacca    1740
tgtaatagga attc                                                       1754
```

<210> SEQ ID NO 35
<211> LENGTH: 240
<212> TYPE: PRT
<213> ORGANISM: Mouse

<400> SEQUENCE: 35

```
Met Pro Arg Gly Pro Val Ala Ala Leu Leu Leu Ile Leu His Gly
1               5                   10                  15

Ala Trp Ser Cys Leu Asp Leu Thr Cys Tyr Thr Asp Tyr Leu Trp Thr
            20                  25                  30

Ile Thr Cys Val Leu Glu Thr Arg Ser Pro Asn Pro Ser Ile Leu Ser
        35                  40                  45

Leu Thr Trp Gln Asp Glu Tyr Glu Glu Leu Gln Asp Gln Glu Thr Phe
    50                  55                  60

Cys Ser Leu His Arg Ser Gly His Asn Thr Thr His Ile Trp Tyr Thr
65                  70                  75                  80
```

```
Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Leu Asn Val Thr Val
        115                 120                 125

Ala Phe Ser Gly Arg Tyr Asp Ile Ser Trp Asp Ser Ala Tyr Asp Glu
        130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
210                 215                 220

Thr Gln Ala Gly Glu Pro Glu Ala Gly Trp Asp Gly Ser Gly Ser Arg
225                 230                 235                 240
```

<210> SEQ ID NO 36
<211> LENGTH: 795
<212> TYPE: DNA
<213> ORGANISM: Mouse

<400> SEQUENCE: 36

```
ctgcaggtcg acaccaccat gccccggggc ccagtggctg ccttactcct gctgattctc      60
catggagctt ggagctgcct ggacctcact tgctacactg actacctctg gaccatcacc     120
tgtgtcctgg agacacggag ccccaacccc agcatactca gtctcacctg caagatgaa     180
tatgaggaac ttcaggacca agagaccttc tgcagcctac acaggtctgg ccacaacacc     240
acacatatat ggtacacgtg ccatatgcgc ttgtctcaat tcctgtccga tgaagttttc     300
attgtcaatg tgacggacca gtctggcaac aactcccaag agtgtggcag ctttgtcctg     360
gctgagagca tcaaaccagc tccccccttg aacgtgactg tggccttctc aggacgctat     420
gatatctcct gggactcagc ttatgacgaa ccctccaact acgtgctgag gggcaagcta     480
caatatgagc tgcagtatcg gaacctcaga gaccctatg ctgtgaggcc ggtgaccaag     540
ctgatctcag tggactcaag aaacgtctct cttctccctg aagagttcca caaagattct     600
agctaccagc tgcaggtgcg ggcagcgcct cagccaggca cttcattcag ggggacctgg     660
agtgagtgga gtgaccccgt catctttcag acccaggctg gggagcccga ggcaggctgg     720
gacggcagcg gacaccacca tcatcaccac ggtagcggcg actataaaga cgatgacgat     780
aagtagtgag aattc                                                      795
```

<210> SEQ ID NO 37
<211> LENGTH: 255
<212> TYPE: PRT
<213> ORGANISM: Mouse

<400> SEQUENCE: 37

```
Met Pro Arg Gly Pro Val Ala Ala Leu Leu Leu Leu Ile Leu His Gly
1               5                   10                  15

Ala Trp Ser Cys Leu Asp Leu Thr Cys Tyr Thr Asp Tyr Leu Trp Thr
```

```
                    20                  25                  30
Ile Thr Cys Val Leu Glu Thr Arg Ser Pro Asn Pro Ser Ile Leu Ser
            35                  40                  45

Leu Thr Trp Gln Asp Glu Tyr Glu Leu Gln Asp Gln Glu Thr Phe
50                  55                  60

Cys Ser Leu His Arg Ser Gly His Asn Thr Thr His Ile Trp Tyr Thr
65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
                100                 105                 110

Val Leu Ala Glu Ser Ile Lys Pro Ala Pro Pro Leu Asn Val Thr Val
                115                 120                 125

Ala Phe Ser Gly Arg Tyr Asp Ile Ser Trp Asp Ser Ala Tyr Asp Glu
130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
                180                 185                 190

Asp Ser Tyr Gln Leu Gln Val Arg Ala Ala Pro Gln Pro Gly Thr
                195                 200                 205

Ser Phe Arg Gly Thr Trp Ser Glu Trp Ser Asp Pro Val Ile Phe Gln
            210                 215                 220

Thr Gln Ala Gly Glu Pro Glu Ala Gly Trp Asp Gly Ser Gly His His
225                 230                 235                 240

His His His His Gly Ser Gly Asp Tyr Lys Asp Asp Asp Lys
                245                 250                 255

<210> SEQ ID NO 38
<211> LENGTH: 792
<212> TYPE: DNA
<213> ORGANISM: Mouse

<400> SEQUENCE: 38
atgaaattct tagtcaacgt tgcccttgtt tttatggtcg tgtacatttc ttacatctat      60
gccggcagcg gacaccacca tcatcaccac ggtagcggcg actataaaga cgatgacgat     120
aagggttccg gatgcctgga cctcacttgc tacactgact acctctggac catcacctgt     180
gtcctggaga cacggagccc caaccccagc atactcagtc tcacctggca agatgaatat     240
gaggaacttc aggaccaaga gaccttctgc agcctacaca ggtctggcca caacaccaca     300
catatatggt acacgtgcca tatgcgcttg tctcaattcc tgtccgatga agttttcatt     360
gtcaatgtga cggaccagtc tggcaacaac tcccaagagt gtggcagctt tgtcctggct     420
gagagcatca aaccagctcc ccccttgaac gtgactgtgg ccttctcagg acgctatgat     480
atctcctggg actcagctta tgacgaaccc tccaactacg tgctgagggg caagctacaa     540
tatgagctgc agtatcggaa cctcagagac ccctatgctg tgaggccggt gaccaagctg     600
atctcagtgg actcaagaaa cgtctctctt ctccctgaag agttccacaa agattctagc     660
taccagctgc aggtgcgggc agcgcctcag ccaggcactt cattcagggg gacctggagt     720
gagtggagtg acccccgtcat ctttcagacc caggctgggg agcccgaggc aggctgggac     780
tagtgagaat tc                                                         792
```

<210> SEQ ID NO 39
<211> LENGTH: 260
<212> TYPE: PRT
<213> ORGANISM: Mouse

<400> SEQUENCE: 39

Met Lys Phe Leu Val Asn Val Ala Leu Val Phe Met Val Val Tyr Ile
1               5                   10                  15

Ser Tyr Ile Tyr Ala Gly Ser Gly His His His His His His Gly Ser
            20                  25                  30

Gly Asp Tyr Lys Asp Asp Asp Lys Gly Ser Gly Cys Leu Asp Leu
        35                  40                  45

Thr Cys Tyr Thr Asp Tyr Leu Trp Thr Ile Thr Cys Val Leu Glu Thr
    50                  55                  60

Arg Ser Pro Asn Pro Ser Ile Leu Ser Leu Thr Trp Gln Asp Glu Tyr
65                  70                  75                  80

Glu Glu Leu Gln Asp Gln Glu Thr Phe Cys Ser Leu His Arg Ser Gly
                85                  90                  95

His Asn Thr Thr His Ile Trp Tyr Thr Cys His Met Arg Leu Ser Gln
            100                 105                 110

Phe Leu Ser Asp Glu Val Phe Ile Val Asn Val Thr Asp Gln Ser Gly
        115                 120                 125

Asn Asn Ser Gln Glu Cys Gly Ser Phe Val Leu Ala Glu Ser Ile Lys
130                 135                 140

Pro Ala Pro Pro Leu Asn Val Thr Val Ala Phe Ser Gly Arg Tyr Asp
145                 150                 155                 160

Ile Ser Trp Asp Ser Ala Tyr Asp Glu Pro Ser Asn Tyr Val Leu Arg
                165                 170                 175

Gly Lys Leu Gln Tyr Glu Leu Gln Tyr Arg Asn Leu Arg Asp Pro Tyr
            180                 185                 190

Ala Val Arg Pro Val Thr Lys Leu Ile Ser Val Asp Ser Arg Asn Val
        195                 200                 205

Ser Leu Leu Pro Glu Glu Phe His Lys Asp Ser Ser Tyr Gln Leu Gln
210                 215                 220

Val Arg Ala Ala Pro Gln Pro Gly Thr Ser Phe Arg Gly Thr Trp Ser
225                 230                 235                 240

Glu Trp Ser Asp Pro Val Ile Phe Gln Thr Gln Ala Gly Glu Pro Glu
                245                 250                 255

Ala Gly Trp Asp
            260

<210> SEQ ID NO 40
<211> LENGTH: 9
<212> TYPE: PRT
<213> ORGANISM: Mouse

<400> SEQUENCE: 40

Ser Val Tyr Asp Phe Phe Val Trp Leu
1               5

<210> SEQ ID NO 41
<211> LENGTH: 8
<212> TYPE: PRT
<213> ORGANISM: Mouse

<400> SEQUENCE: 41

-continued

```
Ser Ile Ile Asn Phe Glu Lys Leu
1               5

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: 5' PCR
      Primer

<400> SEQUENCE: 42
gccttctcag gacgctatga t                                           21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: 5' PCR
      Primer

<400> SEQUENCE: 43
ccctacagca cgtagttgga                                             20

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: PCR Probe

<400> SEQUENCE: 44
tcctgggact cagcttatga cgaacc                                      26
```

METHODS AND COMPOSITIONS FOR MODULATING INTERLEUKIN-21 RECEPTOR ACTIVITY

RELATED APPLICATIONS

This application is a continuation-in-part of co-pending U.S. Ser. No. 09/972,218, filed on Oct. 4, 2001, which is a continuation-in-part of U.S. Ser. No. 09/569,384, filed on May 11, 2000 (pending), which is a continuation-in-part of U.S. Ser. No. 09/560,766, filed Apr. 28, 2000 (abandoned), which is a continuation of U.S. Ser. No. 09/040,005, filed on Mar. 17, 1998, which is now issued as U.S. Pat. No. 6,057,128. This application also claims the benefit of provisional application U.S. Ser. No. 60/373,746, filed on Apr. 17, 2002. The contents of all of these applications are hereby incorporated by reference in their entirety.

FIELD OF THE INVENTION

The present invention relates to methods and compositions for modulating interleukin-21 (IL-21)/IL-21 receptor (MU-1) activity using IL-21 receptor agonists and antagonists. The methods and compositions disclosed herein are useful as immunotherapeutical agents.

BACKGROUND OF THE INVENTION

Human IL-21 is cytokine about a 131-amino acids in length that shows sequence homology to IL-2, IL-4 and IL-15 (Parrish-Novak et al. (2000) *Nature* 408:57–63). Despite low sequence homology among interleukin cytokines, cytokines share a common fold into a "four-helix-bundle" structure that is representative of the family. Most cytokines bind either the class I or the class II cytokine receptors. Class II cytokine receptors include the receptors for IL-10 and the interferons, whereas class I cytokine receptors include the receptors for IL2-IL7, IL-9, IL-11–13, and IL-15, as well as hematopoietic growth factors, leptin and growth hormone (Cosman, D. (1993) *Cytokine* 5:95–106).

Human IL-21R is a class I cytokine receptor that is expressed in lymphoid tissues, in particular by NK, B and T cells (Parrish-Novak et al. (2000) supra). The nucleotide and amino acid sequences encoding human interleukin-21 (IL-21) and its receptor (IL-21R) are described in WO 00/53761; WO 01/85792; Parrish-Novak et al. (2000) supra; Ozaki et al. (2000) *Proc. Natl. Acad. Sci. USA* 97:11439–114444. IL-21R has the highest sequence homology to IL-2 receptor β chain and IL-4 receptor α chain (Ozaki et al. (2000) supra). Upon ligand binding, IL-21R associates with the common gamma cytokine receptor chain (γc) that is shared by receptors for IL-2, IL-3, IL-4, IL-7, IL-9, IL-13 and IL-15 (Ozaki et al. (2000) supra; Asao et al. (2001) *J. Immunol.* 167:1–5). The widespread lymphoid distribution of IL-21R suggests that IL-21 may play a role in immune regulation. Indeed, in vitro studies have shown that IL-21 significantly modulates the function of B cells, CD4$^+$ and CD8$^+$ T cells, and NK cells (Parrish-Novak et al. (2000) supra; Kasaian, M. T. et al. (2002) *Immunity.* 16:559–569). Nevertheless, evidence supporting a regulatory effect of IL-21 in vivo is limited.

SUMMARY OF THE INVENTION

Methods and compositions for modulating the activity of, and/or an interaction between, an interleukin-21 (IL-21) and an IL-21 receptor (also referred to herein as "IL-21R" or "MU-1") using agonists or antagonists of IL-21 or IL-21R are disclosed (also referred to herein as an "IL-21/IL-21R agonist" or "agonist," and "IL-21/IL-21R antagonist" or "antagonist," respectively).

In one embodiment, Applicants have shown that reducing IL-21R activity by using an IL-21 antagonist, e.g., a fusion protein that includes the extracellular domain of the IL-21R fused to an Fc immunoglobulin region, ameliorates inflammatory symptoms in collagen-induced arthritis (CIA) animal models (Example 7). Expression of IL-21R mRNA is upregulated in the paws of CIA mice (Example 8). Accordingly, antagonists of IL-21/IL-21R activity can be used to induce immune suppression in vivo, e.g., for treating or preventing immune cell-associated pathologies (e.g., pathologies associated with aberrant activity of one or more of mature T cells (mature CD8+, mature CD4+ T cells), mature NK cells, B cells, macrophages and megakaryocytes, including transplant rejection and autoimmune disorders, e.g., arthritis (including rheumatoid arthritis).

Accordingly, in one aspect, the invention features a method of treating (e.g., curing, suppressing, ameliorating, delaying or preventing the onset of, or preventing recurrence or relapse of) or preventing an immune cell-associated disease, e.g., rheumatoid arthritis, in a subject, the method includes: administering to the subject an IL-21/IL-21R antagonist, in an amount sufficient to inhibit or reduce immune cell activity and/or cell number, thereby treating or preventing the immune cell-associated disease, e.g., rheumatoid arthritis,.

The IL-21/IL-21R antagonist can be administered to the subject, alone or in combination, with other therapeutic modalities as described herein. Preferably, the subject is a mammal, e.g., a human suffering from an immune cell-associated pathology (e.g., pathology associated with aberrant activity of one or more of mature T cells (mature CD8+, mature CD4+ T cells), mature NK cells, B cells, macrophages and megakaryocytes, including transplant rejection and autoimmune disorders. For example, the method can be used to treat or prevent, in a subject, an immune cell-associated disorders, e.g., a disorder chosen from one or more of: transplant rejection or an autoimmune disorder (e.g., including, for example, diabetes mellitus (type I), arthritis (including rheumatoid arthritis, juvenile rheumatoid arthritis, osteoarthritis, psoriatic arthritis, and ankylosing spondylitis), multiple sclerosis, myasthenia gravis, vasculitis, systemic lupus erythematosis, autoimmune thyroiditis, dermatitis (including atopic dermatitis and eczematous dermatitis), psoriasis, scleroderma, asthma, allergy, IBD or Crohn's disease). Treatment of an arthritic disorder, e.g., a disorder chosen from one or more of rheumatoid arthritis, juvenile rheumatoid arthritis, osteoarthritis, psoriatic arthritis, or ankylosing spondylitis (preferably, rheumatoid arthritis) using the IL-21- or IL-21R antagonists of the present invention is preferred.

In one embodiment, the IL-21/IL-21R antagonist interacts with, e.g., binds to, IL-21 or IL-21R, preferably, mammalian, e.g., human IL-21 or IL-21R (referred to herein as an "IL21 antagonist" and "IL-21R antagonist," respectively), and reduces or inhibits one or more IL-21 and/or IL-21R activities. Preferred antagonists bind to IL-21 or IL-21R with high affinity, e.g., with an affinity constant of at least about $10^7$ M$^{-1}$, preferably about $10^8$ M$^{-1}$, and more preferably, about $10^9$ M$^{-1}$ to $10^{10}$ M$^{-1}$ or stronger.

For example, an IL-21/IL-21R antagonist can reduce and/or inhibit IL-21R activity by neutralizing IL-21. In one embodiment, the antagonist can be a fusion protein that includes a fragment of an IL-21R fused to a non-IL21R fragment, e.g., an immunoglobulin Fc region. In other embodiments, the antagonist is an anti-IL21R or anti-IL21 antibody or an antigen-binding fragment thereof, a soluble form of the IL-21 receptor, a peptide or a small molecule inhibitor.

In one embodiment, the IL-21/IL-21R antagonist is an anti-IL21R or anti-IL21 antibody, or an antigen-binding fragment thereof. E.g., the antibody is a monoclonal or single specificity antibody, that binds to IL-21, e.g., human IL-21, or an IL-21 receptor, e.g., human IL-21 receptor polypeptide, or an antigen-binding fragment thereof (e.g., an Fab, F(ab')2, Fv or a single chain Fv fragment). Preferably, the antibody is a human, humanized, chimeric, or in vitro generated antibody to human IL-21 or human IL-21 receptor polypeptide. Preferably, the antibody is a neutralizing antibody.

In other embodiments, the IL-21/IL-21R antagonist includes full length, or a fragment of an IL-21 polypeptide, e.g., an inhibitory IL-21 receptor-binding domain of an IL-21 polypeptide, e.g., a human IL-21 polypeptide (e.g., a human IL-21 polypeptide as described herein having an amino acid sequence shown as SEQ ID NO:19) or a sequence at least 85%, 90%, 95%, 98% or more identical thereto; or encoded by a corresponding nucleotide sequence shown as SEQ ID NO:18 or a sequence at least 85%, 90%, 95%, 98% or more identical thereto. Alternatively, the antagonist includes full length (e.g., from about amino acids 1–538 or 20–538 of SEQ ID NO:2; or from about amino acids 1–529 or 20–529 of SEQ ID NO:10), or a fragment of an IL-21 receptor polypeptide, e.g., an IL-21-binding domain of an IL-21 receptor polypeptide, e.g., a soluble fragment of an IL-21R (e.g., a fragment of an IL-21R comprising the extracellular domain of murine or human IL-21R; e.g., from about amino acids 1–235, 1–236, 20–235, 20–236 of SEQ ID NO:2 (human), or from about amino acids 1–236, 20–236 of SEQ ID NO:10 (murine), or encoded by the corresponding nucleotides of SEQ ID NO:1 or 9, or a sequence at least 85%, 90%, 95%, 98% or more identical thereto.

In one embodiment, the antagonist is a fusion protein comprising the aforesaid IL-21 or Il-21 receptor polypeptides or fragments thereof and, e.g., fused to, a second moiety, e.g., a polypeptide (e.g., an immunoglobulin chain, a GST, Lex-A or MBP polypeptide sequence). In a preferred embodiment, the fusion protein includes at least a fragment of an IL-21R polypeptide, which is capable of binding IL-21, e.g., a soluble fragment of an IL-21R (e.g., a fragment of an IL-21R comprising the extracellular domain of murine or human IL-21R; e.g., from about amino acids acids 1–235, 1–236, 20–235, 20–236 of SEQ ID NO:2 (human), or from about amino acids 1–236, 20–236 of SEQ ID NO:10 (murine), or encoded by the corresponding nucleotides of SEQ ID NO:1 or 9, or a sequence at least 85%, 90%, 95%, 98% or more identical thereto) and, e.g., fused to, a second moiety, e.g., a polypeptide (e.g., an immunoglobulin chain, an Fc fragment, a heavy chain constant regions of the various isotypes, including: IgG1, IgG2, IgG3, IgG4, IgM, IgA1, IgA2, IgD, and IgE). For example, the fusion protein can include the extracellular domain of human IL-21R, e.g., from about amino acids 1–235, 1–236, 20–235, 20–236 of SEQ ID NO:2, and, e.g., fused to, a human immunoglobulin Fc chain (e.g., human IgG, e.g., human IgG1 or a mutated form of human IgG1). In one embodiment, the human Fc sequence has been mutated at one or more amino acids, e.g., mutated at residues 254 and 257 of SEQ ID NO:28, from the wild type sequence to reduce Fc receptor binding. In other embodiments, the fusion protein can include the extracellular domain of murine IL-21R, e.g., from about amino acids 1–236, 20–235 of SEQ ID NO:10 (murine), and, e.g., fused to, a murine immunoglobulin Fc chain (e.g., murine IgG, e.g., murine IgG2a or a mutated form of murine IgG2a).

The fusion proteins may additionally include a linker sequence joining the first moiety, e.g., an IL-21R fragment, to the second moiety, e.g., the immunoglobulin fragment. In other embodiments, additional amino acid sequences can be added to the N- or C-terminus of the fusion protein to facilitate expression, steric flexibility, detection and/or isolation or purification.

Examples of antagonistic fusion proteins that can be used in the methods of the invention are shown in FIGS. 7–15. In one embodiment, the fusion protein includes an amino acid sequence chosen from, e.g., SEQ ID NO:23, SEQ ID NO:25, SEQ ID NO:27, SEQ ID NO:29, SEQ ID NO:31, SEQ ID NO:33, SEQ ID NO:35, SEQ ID NO:37, or SEQ ID NO:39, or a sequence at least 85%, 90%, 95%, 98% or more identical thereto. In other embodiments, the fusion protein includes an amino acid sequence encoded by a nucleotide sequence chosen from, e.g., SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, or a sequence at least 85%, 90%, 95%, 98% or more identical thereto. Preferred fusion proteins have the amino acid sequence shown as SEQ ID NO:25 or SEQ ID NO:29 (FIGS. 8A–8C and 10A–10C, respectively), or a sequence at least 85%, 90%, 95%, 98% or more identical thereto. In other embodiments, the fusion protein includes an amino acid sequence encoded by a nucleotide sequence chosen from, e.g., SEQ ID NO:24 or SEQ ID NO:28 (FIGS. 8A–8C and 10A–10C, respectively), or a sequence at least 85%, 90%, 95%, 98% or more identical thereto. Most preferably, the fusion protein has the amino acid sequence shown as SEQ ID NO:29, or has an amino acid sequence encoded by a nucleotide sequence shown as SEQ ID NO:28 (FIGS. 10A–10C).

The IL-21/IL-21R antagonists described herein, e.g., the fusion protein described herein, can be derivatized or linked to another functional molecule, e.g., another peptide or protein (e.g., an Fab' fragment). For example, the fusion protein or an antibody, or antigen-binding portion, can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

In one embodiment, the IL-21/IL-21R antagonists described herein, e.g., the pharmaceutical compositions thereof, are administered in combination therapy, i.e., combined with other agents, e.g., therapeutic agents, which are useful for treating immune cell-associated pathological disorders, e.g., a disorder chosen from one or more of: arthritis (including rheumatoid arthritis, juvenile rheumatoid arthritis, osteoarthritis, psoriatic arthritis, or ankylosing spondylitis), or scleroderma, systemic lupus erythematosis, or vasculitis; preferably, rheumatoid arthritis). For example, the combination therapy can include one or more IL-21/IL-21R antagonists, e.g., an anti-IL-21- or anti-IL-21R antibody or an antigen-binding fragment thereof; an IL-21R fusion protein; a soluble IL-21 receptor; a peptide inhibitor or a small molecule inhibitor) co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more herein.

Examples of preferred additional therapeutic agents that can be co-administered and/or co-formulated with one or more IL-21/IL-21R antagonists, include, but are not limited to, one or more of: TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™, p55 kD TNF receptor-IgG fusion protein; TNF enzyme antagonists, e.g., TNFα converting enzyme (TACE) inhibitors); antagonists of IL-12, IL-15, IL-17, IL-18, IL-22; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Most preferred additional therapeutic agents that can be co-administered and/or co-formulated with one or more IL-21/IL-21R antagonists include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™; methotrexate, leflunomide, or a sirolimus (rapamycin) or an analog thereof, e.g., CCI-779.

Applicants have further shown that an IL-21/IL-21R agonist, e.g., an IL-21 polypeptide, stimulates immunity in vivo against immunogenic and non-immunogenic tumor cells (Example 9). The increased immunity is due in part by the IL-21-mediated potentiation of mature CD8+ T cell effector function. IL-21/IL-21R agonists can be used by themselves or in combination with an antigen, e.g., as an adjuvant (e.g., a vaccine adjuvant), to up-regulate an immune response in vivo, e.g., for example, for use in treating cancer or an infectious disorder in a subject.

Accordingly, the invention provides a method of treating (e.g., curing, suppressing, ameliorating, delaying or preventing the onset of, or preventing recurrence or relapse of) or preventing a cancer or an infectious disorder, in a subject, the method includes: administering to the subject an IL-21/IL-21R agonist, e.g., an agent that increases or potentiates IL-21/IL-21R activity, in an amount sufficient to increase immune cell (e.g., CD8+ cell) activity (e.g., effector cell activity) and/or cell number, thereby treating or preventing said disorder. Exemplary cancer disorders include, but are not limited to, a solid tumor, a soft tissue tumor (e.g., a lymphoma or a leukemia), and a metastatic lesion. Examples of infections disorders that can be treated or prevented include bacterial, viral and parasitic infections.

In one embodiment, a method for increasing the ability of a vaccine composition containing an antigen, e.g., an antigen from a pathogen, e.g., a bacterial, viral and parasitic pathogen, or a tumor cell, to elicit a protective immune response in a subject against the antigen by administering to the subject, either simultaneously with or sequentially, to the vaccine composition, an effective adjuvanting amount of an IL-21/IL-21R agonist (e.g., a IL-21 polypeptide or a biologically active fragment thereof, or a nucleic acid encoding the same). In one embodiment, the pathogen against which the vaccine is directed is an intracellular pathogen, e.g., a virus, bacterium, or protozoan. The pathogen may also be an extracellular parasite, e.g., a helminth or bacterium. The antigen may be a whole cell, a protein, a protein subunit or fragment.

Preferred IL-21/IL-21R agonists bind to IL-21 or IL-21R with high affinity, e.g., with an affinity constant of at least about $10^7$ M$^{-1}$, preferably about $10^8$ M$^{-1}$, and more preferably, about $10^9$ M$^{-1}$ to $10^{10}$ M$^{-1}$ or stronger.

In one embodiment, the IL-21/IL-21R agonist is an IL-21 polypeptide, e.g., a human IL-21 polypeptide, or an active fragment thereof (e.g., a human IL-21 polypeptide comprising the amino acid sequence shown as SEQ ID NO:19, or encoded by a nucleotide sequence shown as SEQ ID NO:18, or a sequence at least 85%, 90%, 95%, 98% or more identical thereto). In other embodiments, the IL-21/IL-21R agonist is a fusion protein comprising an IL-21 polypeptide, e.g., human IL-21 polypeptide, or a fragment thereof and, e.g., fused to, a second moiety, e.g., a polypeptide (e.g., an immunoglobulin chain, an Fc fragment, a heavy chain constant regions of the various isotypes, including: IgG1, IgG2, IgG3, IgG4, IgM, IgA1, IgA2, IgD, and IgE); an agonist antibody or antigen-binding fragment thereof, to the IL-21 receptor; or a small molecule or peptide agonist. In other embodiments, the IL-21/IL-21R agonist is an agent that increases the activity or levels of IL-21 by, e.g., increasing expression, processing and/or secretion of functional IL-21. Nucleic acids encoding the aforesaid IL-21/IL-21R agonists and/or antigen can also be administered to the subject.

The IL-21/IL-21R agonists described herein can be used, alone or in combination, with other therapeutic modalities. If desired, the IL-21/IL-21R agonist can be administered in conjunction with one or more additional agents that increase an immune response, e.g., an agent that enhances an immune response to a cancer or infectious disease, in the subject (e.g., an antigen, an antigenic peptide, alone or in combination with an antigen-presenting cell, e.g., a dendritic cell). For example, the IL-21/IL-21R agonist(s) can be administered by themselves, or in combination with an antigen, e.g., as an adjuvant (e.g., a vaccine adjuvant) and/or in combination with other cytokines (e.g., IL-2, GM-CSF and/or IL-15). The combination therapy can be carried out in any order, e.g., IL-15 and antigen can be co-administered to a subject, followed by boosting the immune response by administering IL-21 and the antigen.

Preferably, the subject is a mammal, e.g., a human suffering a cancer or an infectious disorder. The IL-21/IL-21R agonist is preferably designed to increase the immune response to a cancer or infectious disease. The infectious disease can be caused by, e.g., bacterial, parasitic or viral agents.

In another aspect, the invention features a method for modulating, e.g., increasing or decreasing, immune cell activity and/or number (e.g., the activity and/or number of one or more of: a mature T cell (mature, CD8+, CD4+ T cell), mature NK cell, B cell, macrophage or megakaryocyte; preferably, a mature CD8+ T cell or a macrophage) or a population of immune cells, e.g., a mixed or a substantially purified immune cell population. The method includes contacting an immune cell, e.g., an immune cell as described herein, with an IL-21/IL-21R agonist or antagonist, e.g., an agonist or antagonist as described herein, in an amount sufficient to modulate, e.g., increase or decrease, immune cell activity and/or number.

The subject method can be used on cells in culture, e.g. in vitro or ex vivo. For example, immune cells, e.g., T cells as described herein, can be cultured in vitro in culture medium and the contacting step can be effected by adding one or more IL-21/IL-21R agonist(s) or antagonist(s), e.g., an agonist or antagonist as described herein, to the culture medium. Alternatively, the method can be performed on cells (e.g., immune cells as described herein) present in a subject, e.g., as part of an in vivo (e.g., therapeutic or prophylactic) protocol.

The immune cell can be chosen from, e.g., one or more of: a mature T cell (mature, CD8+, CD4+, lymph node T cell, memory T cell), mature NK cell, B cell, antigen presenting cell (APC), e.g., a dendritic cell, macrophage or megakaryocyte, or a population of cells, e.g., a mixed or a substantially purified immune cell population. Preferably, the immune cell is a mature CD8+ T cell or a macrophage.

A change in immune cell activity includes any variation(s), e.g., increase/decrease, in one or more of: proliferation, cytokine secretion and/or production, survival, differentiation, cell responsiveness (e.g., desensitization), cytolytic activity, effector cell activity, gene expression, among others, of the immune cell contacted with an IL-21/IL-21R agonist or antagonist compared to a reference, e.g., an untreated immune cell. For example, contacting an immune cell with an IL-21/IL-21R agonist, e.g., an IL-21 polypeptide, can induce one or more of: proliferation, cytolytic activity, effector cell function, or cytokine secretion of one or more of: antigen- or anti-CD3 antibody stimulated thymocytes; lymph node T cells, mature CD4+ T cells, mature CD8+ T cells, or macrophages.

Responsiveness of immune cells, e.g., T cells, to stimulatory signals can also be modulated using an agonist or antagonist as described herein. For example, proliferation of T cells to alloantigens can be increased in the presence of an IL-21 polypeptide. IL-21 may also enhance proliferation and/or differentiation of mature CD8+ T cells. For example, priming of CD8+ T cells in the presence of IL-21 can generate effector cells with enhanced lytic (CTL) activity and/or increased ability to secrete cytokines, e.g., IFNγ. In other embodiments, IL-21/IL-21R agonist can be used to induce the proliferation and/or cytokine secretion of macrophages.

In one embodiment, a method for decreasing immune cell activity (e.g., the activity of one or more of: a mature T cell (mature, CD8+, CD4+, lymph node T cell, memory T cell), mature NK cell, B cell, antigen presenting cell (APC), e.g., a dendritic cell, macrophage or megakaryocyte, or a population of cells, e.g., a mixed or a substantially purified immune cell population, is provided. The method includes contacting the immune cell with an IL-21/IL-21R antagonist, e.g., an antagonist as described herein, in an amount sufficient to decrease immune cell activity.

In other embodiments, a method for increasing immune cell activity and/or number (e.g., the activity and/or number of one or more of: a mature T cell (mature, CD8+, CD4+, lymph node T cell, memory T cell), mature NK cell, B cell, antigen presenting cell (APC), e.g., a dendritic cell, macrophage or megakaryocyte, or a population of cells, e.g., a mixed or a substantially purified immune cell population, is provided. The method includes contacting an immune cell with an IL-21/IL-21R agonist, e.g., an agonist as described herein, in an amount sufficient to increase immune cell activity.

In another aspect, the invention features a fusion protein that includes at least a fragment of an IL-21R polypeptide, which is capable of binding an IL-21 polypeptide, e.g., a soluble fragment of an IL-21R (e.g., a fragment of an IL-21R comprising the extracellular domain of murine or human IL-21R; e.g., from about amino acids 1–235, 1–236, 20–235, 20–236 of SEQ ID NO:2 (human), or from about amino acids 1–236, 20–236 of SEQ ID NO:10 (murine), or encoded by the corresponding nucleotides of SEQ ID NO:1 or 9, or a sequence at least 85%, 90%, 95%, 98% or more identical thereto) and, e.g., fused to, a second moiety, e.g., a polypeptide (e.g., an immunoglobulin chain, an Fc fragment, a heavy chain constant regions of the various isotypes, including: IgG1, IgG2, IgG3, IgG4, IgM,, IgA1, IgA2, IgD, and IgE). For example, the fusion protein can include the extracellular domain of human IL-21R, e.g., from about amino acids 1–235, 1–236, 20–235, 20–236 of SEQ ID NO:2, and, e.g., fused to, a human immunoglobulin Fc chain (e.g., human IgG, e.g., human IgG1 or a mutated form of human IgG1). In one embodiment, the human Fc sequence has been mutated at one or more amino acids, e.g., mutated at residues 254 and 257 of SEQ ID NO:28, from the wild type sequence to reduce Fc receptor binding. In other embodiments, the fusion protein can include the extracellular domain of murine IL-21R, e.g., from about amino acids 1–236, 20–236 of SEQ ID NO:10 (murine), and, e.g., fused to, a murine immunoglobulin Fc chain (e.g., murine IgG, e.g., murine IgG2a or a mutated form of murine IgG2a). The fusion proteins may additionally include a linker sequence joining the IL-21R fragment to the second moiety. In other embodiments, additional amino acid sequences can be added to the N- or C-terminus of the fusion protein to facilitate expression, detection and/or isolation or purification.

The fusion protein described herein, can be derivatized or linked to another functional molecule, e.g., another peptide or protein (e.g., an Fab' fragment). For example, the fusion protein can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

Examples of antagonistic fusion proteins that can be used in the methods of the invention are shown in FIGS. 7–15. In one embodiment, the fusion protein includes an amino acid sequence chosen from, e.g., SEQ ID NO:23, SEQ ID NO:25, SEQ ID NO:27, SEQ ID NO:29, SEQ ID NO:31, SEQ ID NO:33, SEQ ID NO:35, SEQ ID NO:37, or SEQ ID NO:39, or a sequence at least 85%, 90%, 95%, 98% or more identical thereto. In other embodiments, the fusion protein includes an amino acid sequence encoded by a nucleotide sequence chosen from, e.g., SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, or a sequence at least 85%, 90%, 95%, 98% or more identical thereto. Preferred fusion proteins have the amino acid sequence shown as SEQ ID NO:25 or SEQ ID NO:29 (FIGS. 8A–8C and 10A–10C, respectively), or a sequence at least 85%, 90%, 95%, 98% or more identical thereto. In other embodiments, the fusion protein includes an amino acid sequence encoded by a nucleotide sequence chosen from, e.g., SEQ ID NO:24 or SEQ ID NO:28 (FIGS. 8A–8C and 10A–10C, respectively), or a sequence at least 85%, 90%, 95%, 98% or more identical thereto. Most preferably, the fusion protein has the amino acid sequence shown as SEQ ID NO:29, or has an amino acid sequence encoded by a nucleotide sequence shown as SEQ ID NO:28 (FIG. 10A–10C).

The invention also features nucleic acid sequences that encode the fusion proteins described herein.

In another aspect, the invention features host cells and vectors containing the nucleic acids of the invention. Preferably, the host cell is a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell. For example, nucleic acids encoding the fusion proteins described herein can be expressed in a transgenic animal. In one embodiment, the nucleic acids are placed under the control of a tissue-specific promoter (e.g., a mammary specific promoter) and the antibody is produced in the transgenic animal. For example, the fusion protein is secreted into the milk of the transgenic animal, such as a transgenic cow, pig, horse, sheep, goat or rodent.

In another aspect, the invention provides a process for producing a fusion protein, e.g., a fusion protein as described herein. The process comprises: (a) growing a culture of the host cell of the present invention in a suitable culture medium; and (b) purifying the fusion protein from the culture. Proteins produced according to these methods are also provided.

In another aspect, the invention provides, compositions, e.g., pharmaceutical compositions, which include a pharmaceutically acceptable carrier and at least one of IL-21/IL-21R agonist or an antagonist as described herein (e.g., a fusion protein described herein). In one embodiment, the compositions, e.g., pharmaceutical compositions, comprise a combination of two or more one of the aforesaid IL-21/IL-21R agonists or antagonists. Combinations of the IL-21/IL-21R agonists or antagonists and a drug, e.g., a therapeutic agent (e.g., one or more cytokine and growth factor inhibitors, immunosuppressants, anti-inflammatory agents, metabolic inhibitors, enzyme inhibitors, and/or cytotoxic or cytostatic agents, as described in more herein) or an antigen, e.g., an antigenic peptide and/or an antigen-presenting cell, are also within the scope of the invention.

In one embodiment, the pharmaceutical composition includes an IL-21/IL-21R antagonist agonist and at least one additional therapeutic agent, in a pharmaceutically-acceptable carrier. Examples of preferred additional therapeutic agents that can be co-formulated in a composition, e.g., a pharmaceutical composition, with one or more IL-21/IL-21R antagonists, include, but are not limited to, one or more of: TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™, p55 kD TNF receptor-IgG fusion protein; TNF enzyme antagonists, e.g., TNFα converting enzyme (TACE) inhibitors); antagonists of IL-12, IL-15, IL-17, IL-18, IL-22; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Most preferred additional therapeutic agents that can be co-administered and/or co-formulated with one or more IL-21/IL-21R antagonists include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™; methotrexate, leflunomide, or a sirolimus (rapamycin) or an analog thereof, e.g., CCI-779.

In another embodiment, a pharmaceutical composition useful as a vaccine comprising an antigen from a pathogenic microorganism, e.g., a viral, bacterial or parasitic microorganism, and an effective adjuvanting amount of an IL-21/IL-21R agonist, in a pharmaceutically acceptable carrier, is provided. In one embodiment, the resulting composition is capable of eliciting the vaccinated subject's immunity for a protective response to the pathogen. The IL-21/IL-21R agonist and antigen used in the composition may be a polypeptide or biologically active fragment thereof, or in a composition comprising nucleic acids encoding the same. These nucleic acids, together with the appropriate promoter sequences, may be employed directly as an antigen administered with, or close in time to, the IL-21/IL-21R agonist adjuvant. Alternatively, these nucleic acids sequences may be transduced in alternate vaccine strains of the pathogenic microorganism, and upon expression in vivo may provide the antigen of the vaccine.

In other embodiments, the invention provides a composition, e.g., a pharmaceutical composition, for the treatment or amelioration of a cancer, and a method for adjuvanting a cancer "vaccine," in a pharmaceutically acceptable carrier. A cancer vaccine may comprise an antigen expressed on the surface of a cancer or a tumor cell. This antigen may be naturally present on the cancer cell. Alternatively, the cancer cell may be manipulated ex vivo and transfected with a selected antigen, which it then expresses when introduced into the patient. An exemplary pharmaceutical composition described herein can contain a cancer- or a tumor cell-antigen (either alone as a protein, biologically active fragment thereof, or nucleic acid encoding same), or a cell, e.g., a cancer cell, transfected with the cancer or tumor cell antigen, in combination with an IL-21/IL-21R agonist (e.g., an agonist as described herein, a fragment thereof, or a nucleic acid encoding the same). In one embodiment, the co-administration of IL-21/IL-21 R agonist with the tumor cell antigen enhances the CD8+ T-cell effector cell activity of the tumor cell antigen.

Methods of producing the aforesaid compositions, e.g., vaccine compositions, are also encompassed by the present invention.

The following terms are used interchangeably herein: "MU-1" and "IL-21R," and peptides, polypeptides and proteins.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 1A–1B depict the full-length cDNA sequence of murine IL-21R/MU-1. The nucleotide sequence corresponds to nucleotides 1–2628 of SEQ ID NO:9.

FIGS. 2A–2B depict the amino acid sequences of murine and human IL-21R/MU-1. FIG. 2A depicts the amino acid sequence of murine IL-21R/MU-1 (corresponding to the amino acids 1–529 of SEQ ID NO:10). There is a predicted leader sequence at amino acids 1–19, which was predicted by Susan with score of 10.1 (bold-face type). There is a predicted transmembrane domain at amino acids 237–253 of SEQ ID NO:10 (underlined). Predicted signaling motifs include the following regions: Box 1: amino acids 265–274 and Box 2: amino acids 310–324 (bold and underlined); six tyrosine's are located at amino acid positions 281, 319, 361, 368, 397, and 510, of SEQ ID NO:10. The WSXWS motif (SEQ ID NO:8) is located at amino acid residue 214 to amino acid residue 218 (in large, bold-face type). Potential STAT docking sites include, amino acids 393–398 and amino acids 510–513 of SEQ ID NO:10.

FIG. 2B depicts the amino acid sequence of human MU-1 (corresponding to SEQ ID NO:2). The location of the predicted signal sequence (about amino acids 1–19 of SEQ ID NO:2); WSXWS motif (about amino acids 213–217 of SEQ ID NO:2); and transmembrane domain (about amino acids 236–252, 236–253, 236–254, of SEQ ID NO:2 (underlined)). Potential JAK binding sites, signaling motifs and STAT docking sites are also indicated. The approximate location of these sites is boxed.

FIGS. 3A–3C depict the GAP comparison of human and murine MU-1cDNA sequences (corresponding to nucleic acids 1–2665 of SEQ ID NO:1 and nucleic acids 1–2628 of SEQ ID NO:9, respectively). HuMU-1=human MU-1, murMU-1=murine MU-1. Gap Parameters: Gap Weight=50, Average Match=10.000, Length Weight=3, Average Mismatch=0.000. Percent Identity=66.116.

FIG. 4 depicts a GAP comparison of the human MU-1 protein (corresponding to amino acids 538 of SEQ ID NO:2) and the murine MU-1 protein (corresponding to amino acids 1–529 of SEQ ID NO:10). BLOSUM62 amino acid substitution matrix. (Henikoff, S. and Henikoff, J. G. (1992)). Amino acid substitution matrices from protein blocks (Proc. Natl. Acad. Sci. USA 89: 10915–10919). Gap parameters=Gap Weight: 8, Average Match=2.9 12, Length Weight=2, Average Mismatch=−2.003. Percent Identity=65.267.

FIG. 5 depicts a multiple sequence alignment of the amino acids of human MU-1 (corresponding to SEQ ID NO:2), murine MU-1 (corresponding to SEQ ID NO: 10), and human IL2beta chain (GENbank Accession No. M26062). Leader and transmembrane domains are underlined. Conserved cytokine receptor module motifs are indicated by bold-face type. Potential signaling regions are indicated by underlining and bold-face type.

FIGS. 7A–7B depict an alignment of the nucleotide and amino acid sequences of human IL-21R monomer (corresponding to amino acids 20–235 of SEQ ID NO:2) fused at the amino terminal to honey bee leader sequence and His6 tags (amino acids 1–44 of SEQ ID NO:23). The nucleotide and amino acid sequences are shown as SEQ ID NO:22 and SEQ ID NO:23, respectively.

FIGS. 8A–8C depict an alignment of the nucleotide and amino acid sequences of human IL-21R extracellular domain (corresponding to amino acids 1–235 of SEQ ID NO:2) fused at the C-terminus via a linker (corresponding to amino acids 236–243 of SEQ ID NO:25) to human immunoglobulin G1 (IgG1) Fc sequence (corresponding to amino acids 244–467 of SEQ ID NO:25). The nucleotide and amino acid sequences are shown as SEQ ID NO:24 and SEQ ID NO:25, respectively.

FIGS. 9A–9C depict an alignment of the nucleotide and amino acid sequences of human IL-21R extracellular domain (corresponding to amino acids 1–235 of SEQ ID NO:2) fused at the C-terminus via a linker (corresponding to amino acids 236–243 of SEQ ID NO:27) to human immunoglobulin G1 (IgG1) Fc sequence (corresponding to amino acids 244–467 of SEQ ID NO:27), and His6 sequence tag (corresponding to amino acids 468–492 of SEQ ID NO:27). The nucleotide and amino acid sequences are shown as SEQ ID NO:26 and SEQ ID NO:27, respectively.

FIGS. 10A–10C depicts an alignment of the nucleotide and amino acid sequences of human IL-21R extracellular domain (corresponding to amino acids 1–235 of SEQ ID NO:2) fused at the C-terminus via a linker (corresponding to amino acids 236–243 of SEQ ID NO:29) to human immunoglobulin G1 (IgG1) Fc mutated sequence. The human Fc sequence has been mutated at residues 254 and 257 from the wild type sequence to reduce Fc receptor binding. The nucleotide and amino acid sequences are shown as SEQ ID NO:28 and SEQ ID NO:29, respectively.

FIGS. 11A–11B depict an alignment of the nucleotide and amino acid sequences of human IL-21R extracellular domain (corresponding to amino acids 1–235 of SEQ ID NO:2) fused at the C-terminus to a rhodopsin sequence tag. The nucleotide and amino acid sequences are shown as SEQ ID NO:30 and SEQ ID NO:31, respectively.

FIGS. 12A–12C depict an alignment of the nucleotide and amino acid sequences of human IL-21R extracellular domain (corresponding to amino acids 1–235 of SEQ ID NO:2) fused at the C-terminus to an EK cleavage site and mutated IgG1 Fc region (corresponding to amino acids 236–470 of SEQ ID NO:33). The nucleotide and amino acid sequences are shown as SEQ ID NO:32 and SEQ ID NO:33, respectively.

FIGS. 13A–13B depict an alignment of the nucleotide and amino acid sequences of murine IL-21R extracellular domain fused at the C-terminus to mouse immunoglobulin G2a (IgG2a). The nucleotide (genomic) and amino acid sequences are shown as SEQ ID NO:34 and SEQ ID NO:35, respectively.

FIGS. 14A–14B depict an alignment of the nucleotide and amino acid sequences of murine IL-21R extracellular domain fused at the C-terminus to Flag and His6 sequence tags. The nucleotide (genomic) and amino acid sequences are shown as SEQ ID NO:36 and SEQ ID NO:37, respectively.

FIGS. 15A–15B depict an alignment of the nucleotide and amino acid sequences of (honey bee leader) murine IL-21R extracellular domain fused at the C-terminus to Flag and His6 sequence tags. The nucleotide (genomic) and amino acid sequences are shown as SEQ ID NO:38 and SEQ ID NO:39, respectively.

FIG. 20A shows the level of IL-21 secretion by transduced tumor cells. FIGS. 20(B, C) are bar graphs depicting the biological activity of IL-21 secreted by transduced tumor cells. Naïve splenocytes from either C57BL/6 (B) or Balb/C (C) mice were stimulated for 72 hours with the indicated concentrations of irradiated syngeneic tumor cells. The cultures were supplemented with sub-optimal amount of anti-CD3 and anti-CD28 mAb in 96-well plates. $^3$H thymidine was added during the last 6 hours of culture.

FIGS. 21A and 21B depict the number of B16F1-IL-21 and B16F1-GFP or MethA-IL-21 and MethA-GFP tumor cells, respectively, with respect to time in culture. FIG. 21C is a bar graph depicting expression of IL-21RmRNA in the transfected cells was normalized to cyclophilin values and expressed as relative unite (R.U.).

DETAILED DESCRIPTION OF THE INVENTION

Figure 2B:
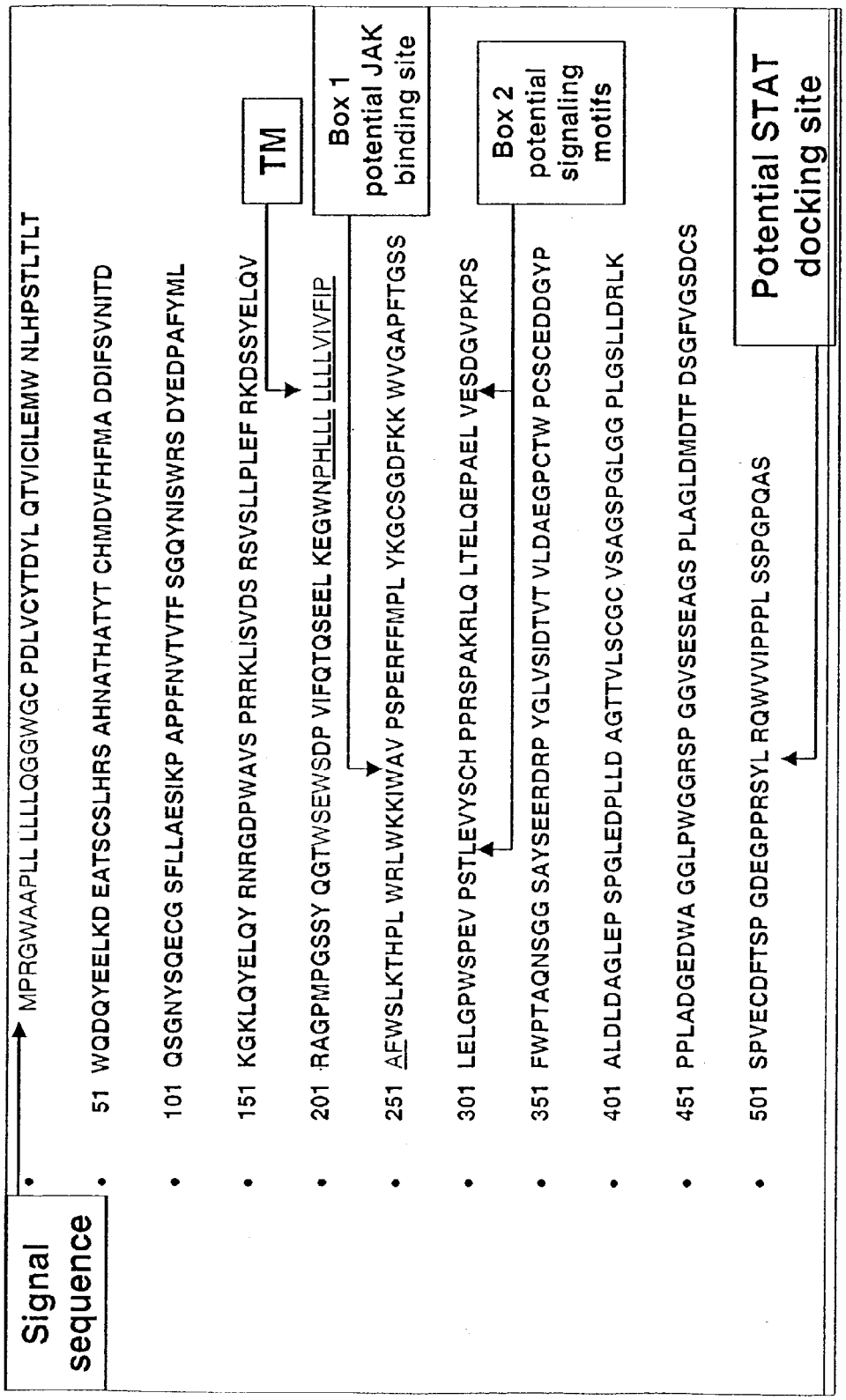
Figure 6:
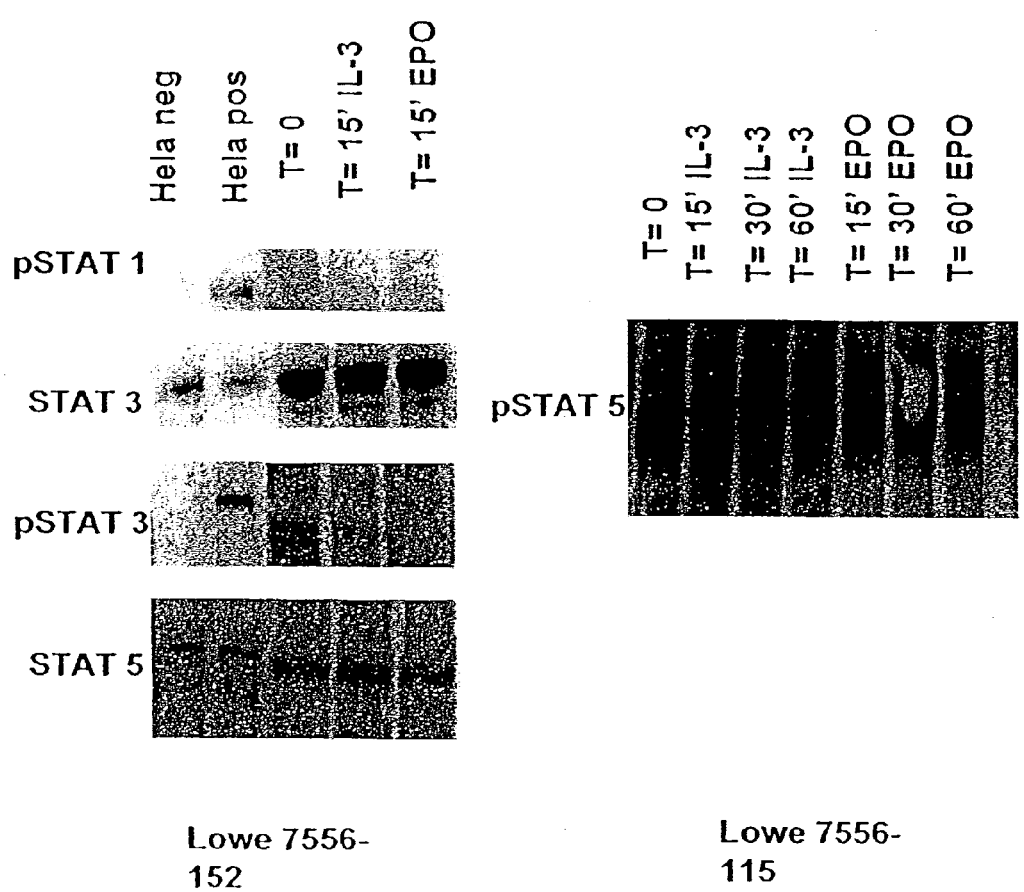
FIG. 6 depicts signaling through MU-1. MU-1 phosphorylates STAT 5 in Clone E7 EPO-MU-1 chimera. Under the conditions specified in Example 3, signaling through MU-1 results in the phosphorylation of STAT 5 at all time-points tested. Treatment of controls or the chimeric BAF-3 cells with IL-3 resulted in phosphorylation of STAT 3, but not STAT 1 or 5.

Methods and compositions for modulating interleukin-21 (IL-21)/IL-21 receptor (MU-1) activity using agonists or antagonists of IL-21 or IL-21 receptor ("IL-21R" or "MU-1"), are disclosed. IL-21/IL-21R antagonists can be used to induce immune suppression in vivo, e.g., for treating or preventing immune cell-associated pathologies (e.g., pathologies associated with aberrant activity of one or more of mature T cells (mature CD8+, mature CD4+ T cells), mature NK cells, B cells, macrophages and megakaryocytes, including transplant rejection and autoimmune disorders). IL-21/IL-21R agonists can be used by themselves or in combination with an antigen, e.g., as an adjuvant (e.g., a vaccine adjuvant), to up-regulate an immune response in vivo, e.g., for example, for use in treating cancer and infectious disorders.

In one embodiment, Applicants have shown that a reduction of IL-21R activity by using a neutralizing fusion protein that includes the extracellular domain of the IL-21R fused to an Fc immunoglobulin region ameliorates inflammatory symptoms in mouse collagen-induced arthritis (CIA) animal models (Example 7). Expression of IL-21R mRNA is upregulated in the paws of CIA mice (Example 8). Accordingly, IL-21R binding agents that antagonize IL-21/IL-21R activity can be used to induce immune suppression in vivo, e.g., for treating or preventing immune cell-associated pathologies (e.g., pathologies associated with aberrant activity of one or more of T cells (CD8+, CD4+ T cells), NK cells, B cells, macrophages and megakaryocytes, including transplant rejection and autoimmune disorders).

In other embodiments, Applicants have shown that agonistic IL-21R binding agent stimulate, primarily via stimulation of CD8+T cells, innate and adaptive immunity in vivo against immunogenic and non-immunogenic tumor cells (Example 9). Accordingly, binding agents that stimulate the IL-21/IL-21R pathway can be used by themselves or in combination with an antigen, e.g., as an adjuvant (e.g., a vaccine adjuvant), to up-regulate an immune response in vivo, e.g., for example, for use in treating cancer and infectious disorders.

In order that the present invention may be more readily understood, certain terms are first defined. Additional definitions are set forth throughout the detailed description.

The term "MU-1," "MU-1 protein," "interleukin-21 receptor" or "IL-21R," as used herein, refers to a class I cytokine family receptor, also known as NILR (WO 01/85792; Parrish-Novak et al. (2000) *Nature* 408:57–63; Ozaki et al. (2000) *Proc. Natl. Acad. Sci. USA* 97:11439–114444). MU-1 is homologous to the shared β chain of the IL-2 and IL-15 receptors, and IL-4α (Ozaki et al. (2000) supra). Upon ligand binding, IL-21R/MU-1 is capable of interacting with a common γ cytokine receptor chain (γc) (Asao et al. (2001) *J. Immunol.* 167:1–5), and inducing the phosphorylation of STAT1 and STAT3 (Asao et al. (2001) or STAT5 (Ozaki et al. (2000). MU-1 shows widespread lymphoid tissue distribution. The term "MU-1" refers to a receptor (preferably of mammalian, e.g., murine or human origin) which is capable of interacting with, e.g., binding to, IL-21 (preferably of mammalian, e.g., murine or human IL-21) and having one of the following features: (i) an amino acid sequence of a naturally occurring mammalian MU-1 polypeptide IL-21R/MU-1 or a fragment thereof, e.g., an amino acid sequence shown as SEQ ID NO:2 (human) or SEQ ID NO:10 (murine) or a fragment thereof; (ii) an amino acid sequence substantially homologous to, e.g., at least 85%, 90%, 95%, 98%, 99% homologous to, an amino acid sequence shown as SEQ ID NO:2 (human) or SEQ ID NO:10 (murine) or a fragment thereof; (iii) an amino acid sequence which is encoded by a naturally occurring mammalian IL-21R/MU-1 nucleotide sequence or a fragment thereof (e.g., SEQ ID NO:1 (human) or SEQ ID NO:9 (murine) or a fragment thereof); (iv) an amino acid sequence encoded by a nucleotide sequence which is substantially homologous to, e.g., at least 85%, 90%, 95%, 98%, 99% homologous to, a nucleotide sequence shown as SEQ ID NO:1 (human) or SEQ ID NO:9 (murine) or a fragment thereof; (v) an amino acid sequence encoded by a nucleotide sequence degenerate to a naturally occurring IL-21R/MU-1 nucleotide sequence or a fragment thereof, e.g., SEQ ID NO:1 (human) or SEQ ID NO:9 (murine) or a fragment thereof; or (vi) a nucleotide sequence that hybridizes to one of the foregoing nucleotide sequence sequences under stringent conditions, e.g., highly stringent conditions.

The IL-21R/MU-1 is of mammalian, preferably, human origin. The nucleotide sequence and the predicted amino acid sequence of human IL-21R/MU-1 are shown in SEQ ID NO:1 and SEQ ID NO:2, respectively. Analysis of the human IL-21R/MU-1 amino acid sequence (SEQ ID NO:2; FIG. 2B) revealed the following structural features: a leader sequence from about (about amino acids 1–19 of SEQ ID NO:2 (FIG. 2B)); WSXWS motif (about amino acids 213–217 of SEQ ID NO:2); transmembrane domain (about amino acids 236–252 of SEQ ID NO:2 (FIG. 2B)); an extracellular domain from about amino acids 1–235 of SEQ ID NO:2; and an intracellular domain from about 253–538 of SEQ ID NO:2. The mature human IL-21R/MU-1 is believed to have the sequence of amino acids 20–538 of SEQ ID NO:2.

The IL-21R/MU-1 cDNA was deposited with the American Type Culture Collection on Mar. 10, 1998, as accession number ATCC 98687.

Any form of IL-21R/MU-1 proteins of less than full length can be used in the methods and compositions of the present invention, provided that it retains the ability to bind to an IL-21 polypeptide. IL-21R/MU-1 proteins of less than full length, e.g., soluble IL-21R, can be produced by expressing a corresponding fragment of the polynucleotide encoding the full-length MU-1 protein in a host cell. These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

As used herein, a "soluble IL-21R/MU-1 polypeptide" is a IL-21R/MU-1 polypeptide incapable of anchoring itself in a membrane. Such soluble polypeptides include, for example, MU-1 or IL-21R polypeptides that lack a sufficient portion of their membrane spanning domain to anchor the polypeptide or are modified such that the membrane spanning domain is non-functional. E.g., a soluble fragment of an L-21R (e.g., a fragment of an IL-21R comprising the extracellular domain of murine or human IL-21R includes an amino acid sequence from about amino acids 1–235, 1–236, 20–235, 20–236 of SEQ ID NO:2 (human), or from about amino acids 1–236, 20–236 of SEQ ID NO:10 (murine). A soluble IL-21R/MU-1 polypeptide can additionally include, e.g., be fused to, a second moiety, e.g., a polypeptide (e.g., an immunoglobulin chain, a GST, Lex-A or MBP polypeptide sequence). For example, a fusion protein can includes at least a fragment of an IL-21R polypeptide, which is capable of binding IL-21, e.g., a soluble fragment of an IL-21R (e.g., a fragment of an IL-21R comprising the extracellular domain of murine or human IL-21R; e.g., from about amino acids acids 1–235, 1–236, 20–235, 20–236 of SEQ ID NO:2 (human), or from about amino acids 1–236, 20–236 of SEQ ID NO:10 (murine), fused to a second moiety, e.g., a polypeptide (e.g., an immunoglobulin chain, an Fc fragment, a heavy chain constant regions of the various isotypes, including: IgG1, IgG2, IgG3, IgG4, IgM, IgA1, IgA2, IgD, and IgE).

The term "interleukin-21" or "L-21" refers to a cytokine showing sequence homology to IL-2, IL-4 and IL-15 (Parrish-Novak et al. (2000) *Nature* 408:57–63). Despite low sequence homology among interleukin cytokines, cytokines share a common fold into a "four-helix-bundle" structure that is representative of the family. It is expressed primarily in activated CD4+ T cells, and has been reported to have effects on NK, B and T cells (Parrish-Novak et al. (2000) supra; Kasaian, M. T. et al. (2002) supra). Il-21 binds to IL-21R (also referred to herein as MU-1 and NILR). Upon IL-21 binding, activation of IL-21R leads to stat5 or stat3 signaling (Ozaki et al. (2000) supra). The term "IL-21" or "IL-21 polypeptide" refers to a protein (preferably of mammalian, e.g., murine or human origin) which is capable of interacting with, e.g., binding to, IL-21R (preferably of mammalian, e.g., murine or human IL-21) and having one of the following features: (i) an amino acid sequence of a naturally occurring mammalian IL-21 or a fragment thereof, e.g., an amino acid sequence shown as SEQ ID NO:19 (human) or a fragment thereof; (ii) an amino acid sequence substantially homologous to, e.g., at least 85%, 90%, 95%, 98%, 99% homologous to, an amino acid sequence shown as SEQ ID NO:19 (human) or a fragment thereof; (iii) an amino acid sequence which is encoded by a naturally occurring mammalian IL-21 nucleotide sequence or a fragment thereof (e.g., SEQ ID NO:18 (human) or a fragment thereof); (iv) an amino acid sequence encoded by a nucleotide sequence which is substantially homologous to, e.g., at least 85%, 90%, 95%, 98%, 99% homologous to, a nucleotide sequence shown as SEQ ID NO:18 (human) or a fragment thereof; (v) an amino acid sequence encoded by a nucleotide sequence degenerate to a naturally occurring IL-21 nucleotide sequence or a fragment thereof, e.g., SEQ ID NO:19 (human) or a fragment thereof; or (vi) a nucleotide sequence that hybridizes to one of the foregoing nucleotide sequence sequences under stringent conditions, e.g., highly stringent conditions.

The phrase "a biological activity of" a MU-1 or IL-21R polypeptide refers to one or more of the biological activities of the corresponding mature MU-1 protein, including, but not limited to, (1) interacting with, e.g., binding to, an IL-21 polypeptide (e.g., a human IL-21 polypeptide); (2) associating with signal transduction molecules, e.g., γc, jak1; (3) stimulating phosphorylation and/or activation of stat proteins, e.g., stat 5 and/or stat3; and/or (4) modulating, e.g., stimulating or decreasing, proliferation, differentiation, effector cell function, cytolytic activity, cytokine secretion, and/or survival of immune cells, e.g., T cells (CD8+, CD4+ T cells), NK cells, B cells, macrophages and megakaryocytes).

As used herein, a "IL-21/IL-21R agonist", that is useful in the method of the invention, refers to an agent which potentiates, induces or otherwise enhances one or biological activities of an IL-21R/MU-1 polypeptide. Preferably, the agonist interacts with, e.g., binds to, an IL-21R/MU-1 polypeptide.

As used herein, a "IL-21/IL-21R antagonist", that is useful in the method of the invention, refers to an agent which reduces, inhibits or otherwise diminishes one or biological activities of an IL-21R/MU-1 polypeptide. Preferably, the antagonist interacts with, e.g., binds to, an IL-21R/MU-1 polypeptide. Antagonism using an IL-21/IL-21R antagonist does not necessarily indicate a total elimination of the IL-21R/MU-1 polypeptide biological activity.

As used herein, a "therapeutically effective amount" of an IL-21/IL-21R agonist or antagonist refers to an amount of an agent which is effective, upon single or multiple dose administration to a subject, e.g., a human patient, at curing, reducing the severity of, ameliorating one or more symptoms of a disorder, or in prolonging the survival of the subject beyond that expected in the absence of such treatment.

As used herein, "a prophylactically effective amount" of an IL-21/IL-21R agonist or antagonist refers to an amount of an IL21/IL-21R agonist or antagonist which is effective, upon single- or multiple-dose administration to a subject, e.g., a human patient, in preventing or delaying the occurrence of the onset or recurrence of a disorder, e.g., a disorder as described herein.

The term "induce", "inhibit", "potentiate", "elevate", "increase", "decrease" or the like, e.g., which denote quantitative differences between two states, refer to at least statistically significant differences between the two states.

The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

As used herein, a "fusion protein" refers to a protein containing two or more operably associated, e.g., linked, moieties, e.g., protein moieties. Preferably, the moieties are covalently associated. The moieties can be directly associate, or connected via a spacer or linker.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901–917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, "isotype" refers to the antibody class (e.g., IgM or IgG1) that is encoded by heavy chain constant region genes.

The term "antigen-binding fragment" of an antibody (or simply "antibody portion," or "fragment"), as used herein, refers to one or more fragments of a full-length antibody that retain the ability to specifically bind to an antigen (e.g., CD3). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423–426; and Huston et al. (1988) *Proc. Natl. Acad. Sci. USA* 85:5879–5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

Sequences similar or homologous (e.g., at least about 85% sequence identity) to the sequences disclosed herein are also part of this application. In some embodiment, the sequence identity can be about 90%, 91%, 92%, 93%, 94%, 95%, 96%, 97%, 98%, 99% or higher. Alternatively, substantial identity exists when the nucleic acid segments will hybridize under selective hybridization conditions (e.g., highly stringent hybridization conditions), to the complement of the strand. The nucleic acids may be present in whole cells, in a cell lysate, or in a partially purified or substantially pure form.

Calculations of "homology" or "sequence identity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444–453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

As used herein, the term "hybridizes under stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×SSC at about 45° C., followed by one or more washes in 0.2×SSC, 0.1% SDS at 55° C. A further example of stringent hybridization conditions are hybridization in 6×SSC at about 45° C., followed by one or more washes in 0.2×SSC, 0.1% SDS at 60° C. Preferably, stringent hybridization conditions are hybridization in 6×SSC at about 45° C., followed by one or more washes in 0.2×SSC, 0.1% SDS at 65° C. Particularly preferred highly stringent conditions (and the conditions that should be used if the practitioner is uncertain about what conditions should be applied to determine if a molecule is within a hybridization limitation of the invention) are 0.5M sodium phosphate, 7% SDS at 65° C., followed by one or more washes at 0.2×SSC, 1% SDS at 65° C.

It is understood that the IL-21/IL-21R agonists and antagonists of the present invention may have additional conservative or non-essential amino acid substitutions, which do not have a substantial effect on their functions.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "recombinant host cell" (or simply "host cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

IL-21/IL-21R Agonists and Antagonists

In one embodiment, an IL-21R/MU-1 polypeptide or active fragments thereof may be fused to a second moiety, e.g., an immunoglobulin or a fragment thereof (e.g., an Fc binding fragment thereof). For example, soluble forms of the IL-21R/MU-1 may be fused through "linker" sequences to the Fc portion of an immunoglobulin. Other fusions proteins, such as those with GST, Lex-A or MBP, may also be used.

The fusion proteins may additionally include a linker sequence joining the IL-21 or IL-21R fragment to the second moiety. For example, the fusion protein can include a peptide linker, e.g., a peptide linker of about 4 to 20, more preferably, 5 to 10, amino acids in length; the peptide linker is 8 amino acids in length. Each of the amino acids in the peptide linker is selected from the group consisting of Gly, Ser, Asn, Thr and Ala; the peptide linker includes a Gly-Ser element. In other embodiments, the fusion protein includes a peptide linker and the peptide linker includes a sequence having the formula (Ser-Gly-Gly-Gly-Gly)y wherein y is 1, 2, 3, 4, 5, 6, 7, or 8.

In other embodiments, additional amino acid sequences can be added to the N- or C-terminus of the fusion protein to facilitate expression, detection and/or isolation or purification. For example, IL-21/IL-21R fusion protein may be linked to one or more additional moieties, e.g., GST, His6 tag, FLAG tag. For example, the fusion protein may additionally be linked to a GST fusion protein in which the fusion protein sequences are fused to the C-terminus of the GST (i.e., glutathione S-transferase) sequences. Such fusion proteins can facilitate the purification of the MU-1 fusion protein.

In another embodiment, the fusion protein is includes a heterologous signal sequence (i.e., a polypeptide sequence that is not present in a polypeptide encoded by a Mu-1 nucleic acid) at its N-terminus. For example, the native Mu-1 signal sequence can be removed and replaced with a signal sequence from another protein. In certain host cells (e.g., mammalian host cells), expression and/or secretion of Mu-1 can be increased through use of a heterologous signal sequence.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A Mu-1 encoding nucleic acid can be cloned into such an expression vector such that the fusion moiety is linked in-frame to the immunoglobulin protein.

In some embodiments, MU-1 fusion polypeptides exist as oligomers, such as dimers or trimers.

The first polypeptide, and/or nucleic acids encoding the first polypeptide, can be constructed using methods known in the art.

In some embodiments, the Mu-1 polypeptide moiety is provided as a variant Mu-1 polypeptide having a mutation in the naturally-occurring Mu-1 sequence (wild type) that results in higher affinity (relative to the non-mutated sequence) binding of the Mu-1 polypeptide to a IL-21.

In some embodiments, the Mu-1 polypeptide moiety is provided as a variant Mu-1 polypeptide having mutations in the naturally-occurring Mu-1 sequence (wild type) that results in a Mu-1 sequence more resistant to proteolysis (relative to the non-mutated sequence).

In some embodiments, the first polypeptide includes full-length Mu-1 polypeptide. Alternatively, the first polypeptide comprise less than full-length Mu-1 polypeptide.

A signal peptide that can be included in the fusion protein is MPLLLLLLLLPSPLHP (SEQ ID NO:21). If desired, one or more amino acids can additionally be inserted between the first polypeptide moiety comprising the Mu-1 moiety and the second polypeptide moiety.

The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second Mu-1 polypeptide. In preferred embodiments, the second polypeptide includes at least a region of an immunoglobulin polypeptide. Immunoglobulin fusion polypeptide are known in the art and are described in e.g., U.S. Pat. Nos. 5,516,964; 5,225,538; 5,428,130; 5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light chain, Fab, $Fab_2$, Fv, or Fc. Preferably, the second polypeptide includes the heavy chain of an immunoglobulin polypeptide. More preferably, the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity (see for example, U.S. Pat. No. 6,136,310). Methods for assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

A preferred second polypeptide sequence includes the amino acid sequence of SEQ ID NO: 17. This sequence includes an Fc region. Underlined amino acids are those that differ from the amino acid found in the corresponding position of the wild-type immunoglobulin sequence:

```
HTCPPCPAPEALGAPSVFLFPPKPKDTLMISRTPEVTCVVVDVSHEDPEV  (SEQ ID NO:17)

KFNWYVDGVEVHNAKTKPREEQYNSTYRVVSVLTVLHQDWLNGKEYKCKV

SNKALPVPIEKTISKAKGQPREPQVYTLPPSREEMTKNQVSLTCLVKGFY

PSDIAVEWESNGQPENNYKTTPPVLDSDGSFFLYSKLTVDKSRWQQGNVF

SCSVMHEALHNHYTQKSLSLSPGK
```

Examples of antagonistic fusion proteins that can be used in the methods of the invention are shown in FIGS. 7–15. In one embodiment, the fusion protein includes an amino acid sequence chosen from, e.g., SEQ ID NO:23, SEQ ID NO:25, SEQ ID NO:27, SEQ ID NO:29, SEQ ID NO:31, SEQ ID NO:33, SEQ ID NO:35, SEQ ID NO:37, or SEQ ID NO:39, or a sequence at least 85%, 90%, 95%, 98% or more identical thereto. In other embodiments, the fusion protein includes an amino acid sequence encoded by a nucleotide sequence chosen from, e.g., SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, or a sequence at least 85%, 90%, 95%, 98% or more identical thereto. Preferred fusion proteins have the amino acid sequence shown as SEQ ID NO:25 or SEQ ID NO:29 (FIGS. 8A–8C and 10A–10C, respectively), or a sequence at least 85%, 90%, 95%, 98% or more identical thereto. In other embodiments, the fusion protein includes an amino acid sequence encoded by a nucleotide sequence chosen from, e.g., SEQ ID NO:24 or SEQ ID NO:28 (FIGS. 8A–8C and 10A–10C, respectively), or a sequence at least 85%, 90%, 95%, 98% or more identical thereto. Most preferably, the fusion protein has the amino acid sequence shown as SEQ ID NO:29, or has an amino acid sequence encoded by a nucleotide sequence shown as SEQ ID NO:28 (FIGS. 10A–10C).

In other embodiments, the IL-21/IL-21R agonists or antagonists are antibodies, or antigen-binding fragments thereof, that bind to IL-21 or IL-21R, preferably, mammalian (e.g., human or murine) IL-21 or IL-21R.

MU-1 proteins of the invention may also be used to immunize animals to obtain polyclonal and monoclonal antibodies which specifically react with the MU-1 protein and which may inhibit binding of ligands to the receptor. Such antibodies may be obtained using the entire MU-1 as an immunogen, or by using fragments of MU-1. Smaller fragments of the MU-1 may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Neutralizing or non-neutralizing antibodies (preferably monoclonal antibodies) binding to MU-1 protein may also be useful in the treatment of conditions described above. These neutralizing monoclonal antibodies may be capable of blocking ligand binding to the MU-1 receptor chain.

The present invention further provides for compositions comprising an antibody that specifically reacts with an IL-21 or an IL-21R.

Human monoclonal antibodies (mAbs) directed against IL-21 or IL-21R can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368: 856–859; Green, L. L. et al. 1994 *Nature Genet.* 7:13–21; Morrison, S. L. et al. 1994 *Proc. Natl. Acad. Sci. USA* 81:6851–6855; Bruggeman et al. 1993 *Year Immunol* 7:33–40; Tuaillon et al. 1993 *PNAS* 90:3720–3724; Brugge-man et al. 1991 *Eur J Immunol* 21:1323–1326). Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. 1989 *Science* 246:1275; and Orlandi et al. 1989 *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primer to a conserved 3' constant region primer can be used for PCR amplification of the heavy and light chain variable regions from a number of murine antibodies (Larrick et al.,1991, *Biotechniques* 11: 152–156). A similar strategy can also been used to amplify human heavy and light chain variable regions from human antibodies (Larrick et al., 1991, *Methods: Companion to Methods in Enzymology* 2:106–110).

Chimeric antibodies, including chimeric immunoglobulin chains, can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041–1043); Liu et al. (1987) PNAS 84:3439–3443; Liu et al., 1987, J. Immunol. 139:3521–3526; Sun et al. (1987) PNAS 84:214–218; Nishimura et al., 1987, Canc. Res. 47:999–1005; Wood et al. (1985) Nature 314:446–449; and Shaw et al., 1988, J. Natl Cancer Inst. 80:1553–1559).

An antibody or an immunoglobulin chain can be humanized by methods known in the art. Humanized antibodies, including humanized immunoglobulin chains, can be generated by replacing sequences of the Fv variable region which are not directly involved in antigen binding with equivalent sequences from human Fv variable regions. General methods for generating humanized antibodies are provided by Morrison, S. L., 1985, Science 229:1202–1207, by Oi et al., 1986, BioTechniques 4:214, and by Queen et al. U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a predetermined target. The recombinant DNA encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDR's of an immunoglobulin chain can be replaced. See e.g., U.S. Pat. No. 5,225,539; Jones et al. 1986 Nature 321:552–525; Verhoeyan et al. 1988 Science 239:1534; Beidler et al. 1988 J. Immunol. 141:4053–4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDR's of a particular human antibody may be replaced with at least a portion of a non-human CDR or only some of the CDR's may be replaced with non-human CDR's. It is only necessary to replace the number of CDR's required for binding of the humanized antibody to a predetermined antigen.

Monoclonal, chimeric and humanized antibodies, which have been modified by, e.g., deleting, adding, or substituting other portions of the antibody, e.g., the constant region, are also within the scope of the invention. For example, an antibody can be modified as follows: (i) by deleting the constant region; (ii) by replacing the constant region with another constant region, e.g., a constant region meant to increase half-life, stability or affinity of the antibody, or a constant region from another species or antibody class; or (iii) by modifying one or more amino acids in the constant region to alter, for example, the number of glycosylation sites, effector cell function, Fc receptor (FcR) binding, complement fixation, among others.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. No. 5,624,821 and U.S. Pat. No. 5,648,260, the contents of all of which are hereby incorporated by reference). Similar type of alterations could be described which if applied to the murine, or other species immunoglobulin would reduce or eliminate these functions.

For example, it is possible to alter the affinity of an Fc region of an antibody (e.g., an IgG, such as a human IgG) for an FcR (e.g., Fc gamma R1), or for C1q binding by replacing the specified residue(s) with a residue(s) having an appropriate functionality on its side chain, or by introducing a charged functional group, such as glutamate or aspartate, or perhaps an aromatic non-polar residue such as phenylalanine, tyrosine, tryptophan or alanine (see e.g., U.S. Pat. No. 5,624,821).

Amino acid sequences of IL-21 polypeptides are publicly known. For example, the nucleotide sequence and amino acid sequence of a human IL-21 is available at Genbank Acc. No. X_011082. The disclosed human IL-21 nucleotide sequence is presented below:

```
  1 gctgaagtga aaacgagacc aaggtctagc tctactgttg gtacttatga gatccagtcc  (SEQ ID NO:18)

61 tggcaacatg gagaggattg tcatctgtct gatggtcatc ttcttgggga cactggtcca 121 caaatcaagc tcccaaggtc aagatcgcca catgattaga atgcgtcaac ttatagatat 181 tgttgatcag ctgaaaaatt atgtgaatga cttggtccct gaatttctgc cagctccaga 241 agatgtagag acaaactgtg agtggtcagc ttttctcctgc tttcagaagg cccaactaaa 301 gtcagcaaat acaggaaaca atgaaaggat aatcaatgta tcaattaaaa agctgaagag 361 gaaaccacct tccacaaatg cagggagaag acagaaacac agactaacat gcccttcatg 421 tgattcttat gagaaaaaac cacccaaaga attcctagaa agattcaaat cacttctcca 481 aaagatgatt catcagcatc tgtcctctag aacacacgga agtgaagatt cctgaggatc 541 taacttgcag ttggacacta tgttacatac tctaatatag tagtgaaagt catttctttg 601 tattccaagt ggaggag
```

The amino acid sequence of the disclosed human IL-21 polypeptide is presented below:

MRSSPGNMERIVICLMVIFLGTLVHKSSSQGQDRHMIRMRQLIDIVDQLK (SEQ ID NO:19)

NYVNDLVPEFLPAPEDVETNCEWSAFSCFQKAQLKSANTGNNERIINVSI

KKLKRKPPSTNAGRRQKHRLTCPSCDSYEKKPPKEFLERFKSLLQKMIHQ

HLSSRTHGSEDS

The invention also encompasses nucleic acids that hybridize to the nucleotide sequence set forth in SEQ ID NO:1, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, under highly stringent conditions (for example, 0.1×SSC at 65° C.). Isolated polynucleotides which encode MU-1 proteins or fusion proteins, but which differ from the nucleotide sequence set forth in SEQ ID NO:1, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, by virtue of the degeneracy of the genetic code are also encompassed by the present invention. Variations in the nucleotide sequence as set forth in SEQ ID NO:1, SEQ ID NO:22, SEQ ID NO:24, SEQ ID NO:26, SEQ ID NO:28, SEQ ID NO:30, SEQ ID NO:32, SEQ ID NO:34, SEQ ID NO:36, or SEQ ID NO:38, which are caused by point mutations or by induced modifications are also included in the invention.

The isolated polynucleotides of the invention may be operably linked to an expression control sequence such as the pMT2 or pED expression vectors disclosed in Kaufman et al., Nucleic Acids Res. 19, 4485–4490 (1991), in order to produce the MU-1 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the MU-1 protein is expressed by a host cell which has been transformed (transfected) with the ligated polynucleotide/expression control sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "regulatory sequence" is intended to includes promoters, enhancers and other expression control elements (e.g., polyadenylation signals) that control the transcription or translation of the antibody chain genes. Such regulatory sequences are described, for example, in Goeddel; *Gene Expression Technology: Methods in Enzymology* 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from FF-1a promoter and BGH poly A, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

The recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

A number of types of cells may act as suitable host cells for expression of the MU-1 protein or fusion protein thereof. Any cell type capable of expressing functional MU-1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The MU-1 protein or fusion protein thereof may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MaxBac® kit), and such methods are well known in the art, as described in Summers and Smith, Texas Agricultural Experiment Station Bulletin No. 1555 (1987), incorporated herein by reference. Soluble forms of the MU-1 protein may also be produced in insect cells using appropriate isolated polynucleotides as described above.

Alternatively, the MU-1 protein or fusion protein thereof may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium,* or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, Meth. Enzym., 185:187–195 (1990). EP 0433225 and copending application U.S. Ser. No. 08/163, 877 describe other appropriate methods.

The MU-1 protein or fusion protein thereof may also be expressed as a product of transgenic animals, e.g., as a component of the milk of transgenic cows, goats, pigs, or sheep which are characterized by somatic or germ cells containing a polynucleotide sequence encoding the MU-1 protein or fusion protein thereof.

The MU-1 protein or fusion protein thereof may be prepared by growing a culture transformed host cells under culture conditions necessary to express the desired protein. The resulting expressed protein may then be purified from the culture medium or cell extracts. Soluble forms of the MU-1 protein or fusion protein thereof can be purified from conditioned media. Membrane-bound forms of MU-1 protein of the invention can be purified by preparing a total membrane fraction from the expressing cell and extracting the membranes with a non-ionic detergent such as Triton X-100.

The MU-1 protein or fusion protein can be purified using methods known to those skilled in the art. For example, the MU-1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the MU-1 protein or fusion protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the MU-1 protein. Affinity columns including antibodies to the MU-1 protein can also be used in purification in accordance with known methods. Some or all of the foregoing purification steps, in various combinations or with other known methods, can also be employed to provide a substantially purified isolated recombinant protein. Preferably, the isolated MU-1 protein is purified so that it is substantially free of other mammalian proteins.

MU-1 proteins or fusion proteins of the invention may also be used to screen for agents which are capable of binding to MU-1. Binding assays using a desired binding protein, immobilized or not, are well known in the art and may be used for this purpose using the MU-1 protein of the invention. Purified cell based or protein based (cell free) screening assays may be used to identify such agents. For example, MU-1 protein may be immobilized in purified form on a carrier and binding or potential ligands to purified MU-1 protein may be measured.

Pharmaceutical Compositions

IL-21/IL-21R-agonists or antagonists may be used as a pharmaceutical composition when combined with a pharmaceutically acceptable carrier. Such a composition may contain, in addition to the IL-21/IL-21R-agonists or antagonists and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL-6, IL-7, IL-8, IL-9, IL-10, IL-11, IL-12, IL-14, IL-15, G-CSF, stem cell factor, and erythropoietin. The pharmaceutical composition may also include anti-cytokine antibodies as described in more detail below. The pharmaceutical composition may contain thrombolytic or anti-thrombotic factors such as plasminogen activator and Factor VIII. The pharmaceutical composition may further contain other anti-inflammatory agents as described in more detail below. Such additional factors and/or agents may be included in the pharmaceutical composition to produce a synergistic effect with an IL-21/IL-21R-agonists or antagonists, or to minimize side effects caused by the IL-21/IL-21R-agonists or antagonists. Conversely IL-21/IL-21R-agonists or antagonists may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which IL-21/IL-21R-agonists or antagonists is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of an IL-21/IL-21R-agonist or antagonist is administered to a subject, e.g., mammal (e.g., a human). An IL-21/IL-21R-agonists or antagonists may be administered in accordance with the method of the invention either alone or in combination with other therapies such as treatments employing cytokines, lymphokines or other hematopoietic factors, or anti-inflammatory agents. When co-administered with one or more agents, an IL-21- and/or IL-21R-binding agent may be administered either simultaneously with the second agent, or sequentially. If administered sequentially, the attending physician will decide on the appropriate sequence of administering an IL-21/IL-21R-agonist or antagonist in combination with other agents.

Administration of an IL-21/IL-21R-agonist or antagonist used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of an IL-21/IL-21R-agonist or antagonist is administered orally, the binding agent will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and preferably from about 25 to 90% binding agent. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, and preferably from about 1 to 50% the binding agent.

When a therapeutically effective amount of an IL-21/IL-21R-agonist or antagonist is administered by intravenous, cutaneous or subcutaneous injection, binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of an IL-21/IL-21R-agonist or antagonist in the pharmaceutical composition of the present invention will depend upon the nature and severity of the condition being treated, and on the nature of prior treatments that the patient has undergone. Ultimately, the attending physician will decide the amount of binding agent with which to treat each individual patient. Initially, the attending physician will administer low doses of binding agent and observe the patient's response. Larger doses of binding agent may be administered until the optimal therapeutic effect is obtained for the patient, and at that point the dosage is not generally increased further. It is contemplated that the various pharmaceutical compositions used to practice the method of the present invention should contain about 0.1 µg to about 100 mg IL-21/IL-21R-agonist or antagonist per kg body weight.

The duration of intravenous therapy using the pharmaceutical composition of the present invention will vary, depending on the severity of the disease being treated and the condition and potential idiosyncratic response of each individual patient. It is contemplated that the duration of each application of the IL-21/IL-21R-agonist or antagonist will be in the range of 12 to 24 hours of continuous intravenous administration. Ultimately the attending physician will decide on the appropriate duration of intravenous therapy using the pharmaceutical composition of the present invention.

The polynucleotide and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Uses of IL-21/IL-21R-Agonists to Enhance an Immune Response

In one aspect, the present invention provides methods for increasing immune cell, e.g., T-cell (e.g., CD8+ T cell) proliferation by contacting an immune cell or a population of immune cells with an IL-21 or IL-21R binding agent which potentiates or enhances the activity of an IL-21 polypeptide. These methods are based, at least in part, on the finding that an agonist IL-21R binding agent stimulated, primarily via stimulation of CD8+ T cells, innate and adaptive immunity in vivo against immunogenic and non-immunogenic tumor cells (Example 9). The methods are also based, in part, on the finding that IL-21 induces proliferation of antigen- or anti-CD3 antibody stimulated thymocytes, lymph node T cells, CD4+ T cells, or CD8+ T cells. Applicants also show that proliferation of T cells to alloantigens can be increased in the presence of IL-21. In addition, IL-21 may also enhance proliferation and/or differentiation of CD8+ T cells (Example 10). For example, priming of CD8+ T cells in the presence of IL-21 can generate effector cells with enhanced lytic (CTL) activity and/or increased ability to secrete cytokines, e.g., IFNγ. IL-21- or an IL-21R binding agent that stimulates IL-21/IL-21R activity can be used to induce the proliferation and/or cytokine secretion of macrophages. Il-21 also has effects on memory T cells and antigen presenting cells (APCs). IL-21 has also been found to be produced by activated CD4+ cells. Accordingly, binding agents that stimulate the IL-21/IL-21R pathway can be used by themselves or in combination with an antigen, e.g., as an adjuvant (e.g., a vaccine adjuvant), to up-regulate an immune response in vivo, e.g., for example, for use in treating cancer and infectious disorders.

In one embodiment, agonistic IL-21/IL-21R agonists may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, *Leishmania* spp., *malaria* spp. and various fungal infections such as candidiasis. Of course, in this regard, a protein of the present invention may also be useful where a boost to the immune system generally may be desirable, i.e., in the treatment of cancer.

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of an IL-21/IL-21R agonist, alone or in combination with, a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of an TL-21/IL-21R agonist, in combination with a peptide having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class .alpha. a chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with an IL-21/IL-21R agonist, and/or a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding an IL-21/IL-21R agonist and/or a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

In other embodiments, the IL-21/IL-21R agonists can be used as vaccine adjuvants. Adjuvants are immune modulating compounds that have the ability to enhance and/or steer the development and profile of immune responses against various antigens that are themselves poorly immunogenic. Cytokines and/or lymphokines can be used as adjuvants. The appropriate selection of adjuvants can induce good humoral and cellular immune responses that would not develop in the absence of adjuvant. In particular, adjuvants have significant effects in enhancing the immune response to subunit and peptide antigens in vaccines. Their stimulatory activity is also beneficial to the development of antigen-specific immune responses directed against protein antigens. For a variety of antigens that require strong mucosal responses, high serum titers, induction of CTL and vigorous cellular responses, adjuvant and cytokine/lymphokine combinations provide stimuli that are not provided by most antigen preparations.

As used herein, the phrase "vaccine adjuvant" or "vaccine therapy" is intended to mean the use of an IL-21/IL-21R agonist, e.g., an IL-21 polypeptide or polynucleotide encoding the same, in combination with an antigen (e.g., viral, parasitic and bacterial polypeptides, proteins or peptides), or other antigens (e.g., tumor or cancer cell polypeptides, proteins or peptides) or polynucleotides encoding the antigen to enhance, suppress or otherwise modulate an immune response to the antigen. For the purpose of this definition, "combination" shall mean use in conjunction with, simultaneous with (combined or uncombined) or sequentially with an antigen.

The term "vaccine adjuvant composition" refers to a vaccine adjuvant that additionally includes immunologically acceptable diluents or carriers in a conventional manner to prepare injectable liquid solutions or suspensions. The vaccine adjuvant composition may additionally include agents that further enhance an immune response elicited by IL-21. For example, the vaccine adjuvant composition may additionally include 3-O-deacylated monophosphoryl lipid A (MPL™) or monophosphoryl lipid A and derivatives and analogs thereof. MPL™ can be used in a range of 1–100 µg/dose.

The antigens used for vaccine therapy include proteins, peptides or polypeptides derived from immunogenic and non-immunogenic proteins, as well as any of the following: saccharides, proteins, poly- or oligonucleotides, or other macromolecular components, or fragments thereof. As used in this section, a "peptide" comprises a series of at least six amino acids and contains at least one antigenic determinant, while a "polypeptide" is a longer molecule than a peptide, but does not constitute a full-length protein. As used herein, a "fragment" comprises a portion, but less than all of a saccharide, protein, poly- or oligonucleotide, or other macromolecular components.

As used herein, the term "effective adjuvanting amount" means a dose of the combination of adjuvants described herein, which is suitable to elicit an increased immune response in a vertebrate host. The particular dosage will depend in part upon the age, weight and medical condition of the host, as well as on the method of administration and the antigen.

The vaccine adjuvant composition of the invention can be administered to a human or non-human vertebrate by a variety of routes, including, but not limited to, intranasal, oral, vaginal, rectal, parenteral, intradermal, transdermal (see, e.g., International application WO 98/20734 (44), which is hereby incorporated by reference), intramuscular, intraperitoneal, subcutaneous, intravenous and intraarterial. The amount of the antigen component or components of the antigenic composition will vary depending in part upon the identity of the antigen, as well as upon the age, weight and medical condition of the host, as well as on the method of administration. Again, suitable doses are readily determined by persons skilled in the art. It is preferable, although not required, that the antigen and the combination of adjuvants be administered at the same time. The number of doses and the dosage regimen for the antigenic composition are also readily determined by persons skilled in the art. In some instances, the adjuvant properties of the combination of adjuvants may reduce the number of doses needed or the time course of the dosage regimen.

The combinations of adjuvants of this invention are suitable for use in combination with wide variety of antigens from a wide variety of pathogenic microorganisms, including but not limited to those from viruses, bacteria, fungi or parasitic microorganisms that infect humans and non-human vertebrates, or from a cancer cell or tumor cell (e.g., sarcoma, melanoma, lymphoma, leukemia, neuroblastoma, carcinoma). The antigen may comprise peptides or polypeptides derived from proteins, as well as fragments of any of the following: saccharides, proteins, poly- or oligonucleotides, cancer or tumor cells, allergens, amyloid peptide protein, or other macromolecular components. In some instances, more than one antigen is included in the antigenic composition.

Desirable viral vaccines containing the adjuvant combinations of this invention include those directed to the prevention and/or treatment of disease caused by, without limitation, Human immunodeficiency virus, Simian immunodeficiency virus, Respiratory syncytial virus, Parainfluenza virus types 1–3, Influenza virus, Herpes simplex virus, Human cytomegalovirus, Hepatitis A virus, Hepatitis B virus, Hepatitis C virus, Human papillomavirus, poliovirus, rotavirus, caliciviruses, Measles virus, Mumps virus, Rubella virus, adenovirus, rabies virus, canine distemper virus, rinderpest virus, coronavirus, parvovirus, infectious rhinotracheitis viruses, feline leukemia virus, feline infectious peritonitis virus, avian infectious bursal disease virus, Newcastle disease virus, Marek's disease virus, porcine respiratory and reproductive syndrome virus, equine arteritis virus and various Encephalitis viruses. In one embodiment, the IL-21/IL-21R agonists is administered in combination with a TNF antagonist, e.g., a TNF antagonist as described herein, to treat a Hepatitis C virus infection.

Desirable bacterial vaccines containing the adjuvant combinations of this invention include those directed to the prevention and/or treatment of disease caused by, without limitation, *Haemophilus influenzae* (both typable and nontypable), *Haemophilus somnus*, *Moraxella catarrhalis*, *Streptococcus pneumoniae*, *Streptococcus pyogenes*, *Streptococcus agalactiae*, *Streptococcus faecalis*, *Helicobacter pylori*, *Neisseria meningitidis*, *Neisseria gonorrhoeae*, *Chlamydia trachomatis*, *Chlamydia pneumoniae*, *Chlamydia psittaci*, *Bordetella pertussis*, *Salmonella typhi*, *Salmonella typhimurium*, *Salmonella choleraesuis*, *Escherichia coli*, *Shigella*, *Vibrio cholerae*, *Corynebacterium diphtheriae*, *Mycobacterium tuberculosis*, *Mycobacterium avium-Mycobacterium intracellulare* complex, *Proteus mirabilis*, *Proteus vulgaris*, *Staphylococcus aureus*, *Clostridium tetani*, *Leptospira interrogans*, *Borrelia burgdorferi*, *Pasteurella haemolytica*, *Pasteurella multocida*, *Actinobacillus pleuropneumoniae* and *Mycoplasma gallisepticum*.

Desirable vaccines against fungal pathogens containing the adjuvant combinations of this invention include those directed to the prevention and/or treatment of disease caused by, without limitation, *Aspergillis*, *Blastomyces*, *Candida*, *Coccidiodes*, *Cryptococcus* and *Histoplasma*.

Desirable vaccines against parasites containing the adjuvant combinations of this invention include those directed to the prevention and/or treatment of disease caused by, without limitation, *Leishmania major, Ascaris, Trichuris, Giardia, Schistosoma, Cryptosporidium, Trichomonas, Toxoplasma gondii* and *Pneumocystis carinii*.

Desirable vaccines for eliciting a therapeutic or prophylactic anti-cancer effect in a vertebrate host, which contain the adjuvant combinations of this invention, include those utilizing a cancer antigen or tumor-associated antigen including, without limitation, prostate specific antigen (PSA), prostate-specific membrane antigen (PSMA), carcino-embryonic antigen (CEA), MUC-1, Her2, CA-125, MAGE-3, EGFR, HELP, GCC, CD66-c, prostasin, TMPRSS3, TADG 12 and TADG 15.

Desirable vaccines for moderating responses to allergens in a vertebrate host, which contain the adjuvant combinations of this invention, include those containing an allergen or fragment thereof. Examples of such allergens are described in U.S. Pat. No. 5,830,877 (45) and published International Patent Application Number WO 99/51259 (46), which are hereby incorporated by reference, and include pollen, insect venoms, animal dander, fungal spores and drugs (such as penicillin). The vaccines interfere with the production of IgE antibodies, a known cause of allergic reactions.

Desirable vaccines for preventing or treating disease characterized by amyloid deposition in a vertebrate host, which contain the adjuvant combinations of this invention, include those containing portions of amyloid peptide protein (APP). This disease is referred to variously as Alzheimer's disease, amyloidosis or amyloidogenic disease. Thus, the vaccines of this invention include the adjuvant combinations of this invention plus Aβ peptide, as well as fragments of Aβ peptide and antibodies to Aβ peptide or fragments thereof.

In the case of HIV and SIV, the antigenic compositions comprise at least one protein, polypeptide, peptide or fragment derived from said protein. In some instances, multiple HIV or SIV proteins, polypeptides, peptides and/or fragments are included in the antigenic composition.

The adjuvant combination formulations of this invention are also suitable for inclusion as an adjuvant in polynucleotide vaccines (also known as DNA vaccines). Such vaccines may further include facilitating agents such as bupivicaine (see U.S. Pat. No. 5,593,972 (49), which is hereby incorporated by reference).

Uses of IL-21/IL-21R Antagonists to Decrease Immune Cell Activity

In yet another aspect, the invention features a method for inhibiting the activity of an immune cell, e.g., mature T cells (mature CD8+ T cells, mature CD4+ T cells), mature NK cells, B cells, macrophages and megakaryocytes, or a population thereof, by contacting a population of T cells with an IL-21/IL-21R antagonist in an amount sufficient to inhibit the activity of the immune cell or population. Antagonists of IL-21 and/or IL-21R (e.g., a fusion protein or a neutralizing antibody, as described herein) can also be administered to subjects for which inhibition of an immune response is desired. These conditions include, e.g., autoimmune disorders (e.g., arthritic disorders), or organ transplantation.

Applicants have shown that a reduction of IL-21R activity by using a neutralizing fusion protein that includes the extracellular domain of the IL-21R fused to an Fc immunoglobulin region ameliorates inflammatory symptoms in mouse collagen-induced arthritis (CIA) animal models (Example 7). Expression of IL-21R mRNA is upregulated in the paws of CIA mice (Example 8). Accordingly, IL-21R binding agents that antagonize IL-21/IL 21R activity can be used to induce immune suppression in vivo, e.g., for treating or preventing immune cell-associated pathologies, including transplant rejection and autoimmune disorders.

The IL-21R DNA also maps to the chromosomal locus for Crohn's disease. As a result, binding agents of the present invention may be used to treat Crohn's disease and other inflammatory bowel diseases.

The subject method can also be used to modulate (e.g., inhibit) the activity, e.g., proliferation, differentiation, survival) of an immune or hematopoietic cell (e.g., a cell of myeloid, lymphoid, erythroid lineages, or precursor cells thereof), and, thus, can be used to treat or prevent a variety of immune disorders. Non-limiting examples of the disorders that can be treated or prevented include, but are not limited to, transplant rejection, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, spondyoarthropathy, ankylosing spondylitis, intrinsic asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, and allergy such as, atopic allergy. Preferred disorders that can be treated using the binding agents of the invention include arthritic disorders (e.g., rheumatoid arthritis, juvenile rheumatoid arthritis, osteoarthritis, psoriatic arthritis, and ankylosing spondylitis (preferably, rheumatoid arthritis)), multiple sclerosis, type I diabetes, lupus (SLE), IBD, Crohn's disease, asthma, vasculitis, allergy, scleroderma and psoriasis.

In another embodiment, IL-21/IL-21R antagonists, alone or in combination with, other therapeutic agents as described herein (e.g., TNF antagonists) can be used to treat multiple myeloma and related B lymphocytic malignancies (Brenne, A. et al. (2002) *Blood* Vol. 99(10):3756–3762).

Using the IL-21/IL-21R antagonists, it is possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process that requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions, e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of an IL-21/IL-21R antagonist, in combination with a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens.

The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci U.S.A., 89:11102–11105 (1992). In addition, murine models of GVHD (see Paul ed., Fundamental immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of IL-21/IL-21R antagonists in combination with reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, IL-21/IL-21R antagonists in combination with blocking reagents may induce antigen-specific tolerance of autoreactive T cells which could lead to long-term relief from the disease. The efficacy of these agents in preventing or alleviating autoimmune disorders can be determined using a number of well-characterized animal models of human autoimmune diseases. Examples include murine experimental autoimmune encephalitis, systemic lupus erythmatosis in MRL/lpr/lpr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

In one embodiment, the IL-21/IL-21R antagonists, e.g., pharmaceutical compositions thereof, are administered in combination therapy, i.e., combined with other agents, e.g., therapeutic agents, that are useful for treating pathological conditions or disorders, such as immune and inflammatory disorders. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more IL-21/IL-21R antagonists, e.g., an antibody or an antigen-binding fragment thereof (e.g., a chimeric, humanized, human, or in vitro generated antibody or antigen-binding fragment thereof) against IL-21 or IL-21 receptor, an IL-21 fusion protein, a soluble IL-21 receptor, peptide inhibitor or a small molecule inhibitor) co-formulated with, and/or co-administered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more IL-21/IL-21R antagonists described herein may be used in combination with two or more of the therapeutic agents described herein. Such combination therapies may advantageously utilize lower dosages of the administered therapeutic agents, thus avoiding possible toxicities or complications associated with the various monotherapies. Moreover, the therapeutic agents disclosed herein act on pathways that differ from the IL-21/IL-21R receptor pathway, and thus are expected to enhance and/or synergize with the effects of the IL-21/IL-21R antagonists.

Preferred therapeutic agents used in combination with an IL-21/IL-21R antagonist are those agents that interfere at different stages in the autoimmune and subsequent inflammatory response. In one embodiment, one or more IL-21/IL-21R antagonist described herein may be co-formulated with, and/or co-administered with, one or more additional agents such as other cytokine or growth factor antagonists (e.g., soluble receptors, peptide inhibitors, small molecules, ligand fusions); or antibodies or antigen-binding fragments thereof that bind to other targets (e.g., antibodies that bind to other cytokines or growth factors, their receptors, or other cell surface molecules); and anti-inflammatory cytokines or agonists thereof. Non-limiting examples of the agents that can be used in combination with the IL-21/IL-21R antagonists described herein, include, but are not limited to, antagonists of one or more interleukins (ILs) or their receptors, e.g., antagonists of IL-1, IL-2, IL-6, IL-7, IL-8, IL-12, IL-13, IL-15, IL-16, IL-18, and IL-22; antagonists of cytokines or growth factors or their receptors, such as tumor necrosis factor (TNF), LT, EMAP-II, GM-CSF, FGF and PDGF. IL-21/IL-21R antagonists can also be combined with inhibitors of, e.g., antibodies to, cell surface molecules such as CD2, CD3, CD4, CD8, CD25, CD28, CD30, CD40, CD45, CD69, CD80 (B7.1), CD86 (B7.2), CD90, or their ligands, including CD154 (gp39 or CD40L), or LFA-1/ICAM-1 and VLA-4/VCAM-1 (Yusuf-Makagiansar H. et al. (2002) *Med Res Rev* 22(2):146–67). Preferred antagonists that can be used in combination with IL-21/IL-21R antagonists described herein include antagonists of IL-1, IL-12, TNFa, IL-15, IL-17, IL-18, and IL-22.

Examples of those agents include IL-12 antagonists, such as chimeric, humanized, human or in vitro generated antibodies (or antigen-binding fragments thereof) that bind to IL-12 (preferably human IL-12), e.g., the antibody disclosed in WO 00/56772, Genetics Institute/BASF); IL-12 receptor inhibitors, e.g., antibodies to human IL-12 receptor; and soluble fragments of the IL-12 receptor, e.g., human IL-12 receptor. Examples of IL-15 antagonists include antibodies (or antigen-binding fragments thereof) against IL-15 or its receptor, e.g., chimeric, humanized, human or in vitro generated antibodies to human IL-15 or its receptor, soluble fragments of the IL-5 receptor, and IL-15-binding proteins. Examples of IL-18 antagonists include antibodies, e.g., chimeric, humanized, human or in vitro generated antibodies (or antigen-binding fragments thereof), to human IL-18, soluble fragments of the IL-18 receptor, and IL-18 binding proteins (IL-18BP, Mallet et al. (2001) Circ. Res. 28). Examples of IL-1 antagonists include Interleukin-1-converting enzyme (ICE) inhibitors, such as Vx740, IL-1 antagonists, e.g., IL-1RA (ANIKINRA, AMGEN), sIL1RII (Immunex), and anti-IL-1 receptor antibodies (or antigen-binding fragments thereof).

Examples of TNF antagonists include chimeric, humanized, human or in vitro generated antibodies (or antigen-binding fragments thereof) to TNF (e.g., human TNF a), such as D2E7, (human TNFa antibody, U.S. Pat. No. 6,258,562; BASF), CDP-571/CDP-870/BAY-10-3356 (humanized anti-TNFa antibody; Celltech/Pharmacia), cA2 (chimeric anti-TNFa antibody; Remicade™, Centocor); anti-TNF antibody fragments (e.g., CPD870); soluble fragments of the TNF receptors, e.g., p55 or p75 human TNF receptors or derivatives thereof, e.g., 75 kdTNFR-IgG (75 kD TNF receptor-IgG fusion protein, Enbrel™; Immunex; see e.g., Arthritis & Rheumatism (1994) Vol. 37, S295; J. Invest. Med. (1996) Vol. 44, 235A), p55 kdTNFR-IgG (55 kD TNF receptor-IgG fusion protein (Lenercept)); enzyme antagonists, e.g., TNFa converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see e.g., *Arthritis & Rheumatism* (1996) Vol. 39, No. 9 (supplement), S284; Amer. J. Physiol.—*Heart and Circulatory Physiology* (1995) Vol. 268, pp. 37–42). Preferred TNF antagonists are soluble fragments of the TNF receptors, e.g., p55 or p75 human TNF receptors or derivatives thereof, e.g., 75 kdTNFR-IgG, and TNFa converting enzyme (TACE) inhibitors.

In other embodiments, the IL-21-/IL21R binding agents described herein can be administered in combination with one or more of the following: IL-13 antagonists, e.g., soluble IL-13 receptors (sIL-13) and/or antibodies against IL-13; IL-2 antagonists, e.g., DAB 486-IL-2 and/or DAB 389-IL-2 (IL-2 fusion proteins; Seragen; see e.g., Arthritis & Rheumatism (1993) Vol. 36, 1223), and/or antibodies to IL-2R, e.g., anti-Tac (humanized anti-IL-2R; Protein Design Labs, Cancer Res. 1990 Mar 1; 50(5):1495–502). Yet another combination includes IL-21 antagonists in combination with non-depleting anti-CD4 inhibitors (IDEC-CE9.1/SB 210396 (non-depleting primatized anti-CD4 antibody; IDEC/Smith-Kline). Yet other preferred combinations include antagonists of the co-stimulatory pathway CD80 (B7.1) or CD86 (B7.2) including antibodies, soluble receptors or antagonistic ligands; as well as p-selectin glycoprotein ligand (PSGL), anti-inflammatory cytokines, e.g., IL-4 (DNAX/Schering); IL-10 (SCH 52000; recombinant IL-10 DNAX/Schering); IL-13 and TGF, and agonists thereof (e.g., agonist antibodies).

In other embodiments, one or more IL-21-/IL21R binding agents can be co-formulated with, and/or co-administered with, one or more anti-inflammatory drugs, immunosuppressants, or metabolic or enzymatic inhibitors. Non-limiting examples of the drugs or inhibitors that can be used in combination with the IL-21 antagonists described herein, include, but are not limited to, one or more of: non-steroidal anti-inflammatory drug(s) (NSAIDs), e.g., ibuprofen, Tenidap (see e.g., Arthritis & Rheumatism (1996) Vol. 39, No. 9 (supplement), S280)), Naproxen (see e.g., Neuro Report (1996) Vol. 7, pp. 1209–1213), Meloxicam, Piroxicam, Diclofenac, and Indomethacin; Sulfasalazine (see e.g., Arthritis & Rheumatism (1996) Vol. 39, No. 9 (supplement), S281); corticosteroids such as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl]methylamino]benzoyl]-L-glutamic acid); and inhibitors of pyrimidine biosynthesis, e.g., dihydroorotate dehydrogenase (DHODH) inhibitors (e.g., leflunomide (see e.g., *Arthritis & Rheumatism* (1996) Vol. 39, No. 9 (supplement), S 131; Inflammation Research (1996) Vol. 45, pp. 103–107). Preferred therapeutic agents for use in combination with IL-21/IL-21R antagonists include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppresants, e.g., cyclosporin, tacrolimus (FK-506); and mTOR inhibitors, e.g., sirolimus (rapamycin) or rapamycin derivatives, e.g., soluble rapamycin derivatives (e.g., ester rapamycin derivatives, e.g., CCI-779 (Elit. L. (2002) *Current Opinion Investig. Drugs* 3(8):1249–53; Huang, S. et al.. (2002) *Current Opinion Investig. Drugs* 3(2):295–304); agents which interfere with signaling by proinflammatory cytokines such as TNFa or IL-1 (e.g. IRAK, NIK, IKK, p38 or MAP kinase inhibitors); COX2 inhibitors, e.g., celecoxib and variants thereof, MK-966, see e.g., Arthritis & Rheumatism (1996) Vol. 39, No. 9 (supplement), S81); phosphodiesterase inhibitors, e.g., R973401 (phosphodiesterase Type IV inhibitor; see e.g., Arthritis & Rheumatism (1996) Vol. 39, No. 9 (supplement), S282)); phospholipase inhibitors, e.g., inhibitors of cytosolic phospholipase 2 (cPLA2) (e.g., trifluoromethyl ketone analogs (U.S. Pat. No. 6,350, 892)); inhibitors of vascular endothelial cell growth factor or growth factor receptor, e.g., VEGF inhibitor and/or VEGF-R inhibitor; and inhibitors of angiogenesis. Preferred therapeutic agents for use in combination with IL-21/IL-21R antagonists immunosuppresants, e.g., cyclosporin, tacrolimus (FK-506); and mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2) (e.g., trifluoromethyl ketone analogs)

Additional examples of therapeutic agents that can be combined with an IL-21/IL-21R antagonist include one or more of: 6-mercaptopurines (6-MP); azathioprine sulphasalazine; mesalazine; olsalazine chloroquinine/hydroxychloroquine; pencillamine; aurothiornalate (intramuscular and oral); azathioprine; cochicine; beta-2 adrenoreceptor agonists (salbutamol, terbutaline, salmeteral); xanthines (theophylline, arninophylline); cromoglycate; nedocromil; ketotifen; ipratropium and oxitropium; mycophenolate mofetil; adenosine agonists; antithrombotic agents; complement inhibitors; and adrenergic agents.

The use of the IL-21-/IL21R binding agents disclosed herein in combination with other therapeutic agents to treat or prevent specific immune disorders is discussed in further detail below.

Non-limiting examples of agents for treating or preventing arthritic disorders (e.g., rheumatoid arthritis, inflammatory arthritis, rheumatoid arthritis, juvenile rheumatoid arthritis, osteoarthritis and psoriatic arthritis), with which an IL-21-/IL21R binding agent can be combined include one or more of the following: IL12 antagonists as described herein, NSAIDs; CSAIDs; TNF's, e.g., TNFa, antagonists as described herein; non-depleting anti-CD4 antibodies as described herein; IL-2 antagonists as described herein; anti-inflammatory cytokines, e.g., IL-4, IL-10, IL-13 and TGFa, or agonists thereof; IL-1 or IL-1 receptor antagonists as described herein); phosphodiesterase inhibitors as described herein; COX-2 inhibitors as described herein; Iloprost (see e.g., Arthritis & Rheumatism (1996) Vol. 39, No. 9 (supplement), S82); methotrexate; thalidomide (see e.g., Arthritis & Rheumatism (1996) Vol. 39, No. 9 (supplement), S282) and thalidomide-related drugs (e.g., Celgen); leflunomide; inhibitor of plasminogen activation, e.g., tranexamic acid; see e.g., Arthritis & Rheumatism (1996) Vol. 39, No. 9 (supplement), S284); cytokine inhibitor, e.g., T-614; see e.g., Arthritis & Rheumatism (1996) Vol. 39, No. 9 (supplement), S282); prostaglandin E1 (see e.g., Arthritis & Rheumatism (1996) Vol. 39, No. 9 (supplement), S282); azathioprine (see e.g., Arthritis & Rheumatism (1996) Vol. 39, No. 9 (supplement), S281); an inhibitor of interleukin-1 converting enzyme (ICE); zap-70 and/or lck inhibitor (inhibitor of the tyrosine kinase zap-70 or lck); an inhibitor of vascular endothelial cell growth factor or vascular endothelial cell growth factor receptor as described herein; an inhibitor of angiogenesis as described herein; corticosteroid anti-inflammatory drugs (e.g., SB203580); TNF-convertase inhibitors; interleukin-11 (see e.g., Arthritis & Rheumatism (1996) Vol. 39, No. 9 (supplement), S296); interleukin-13 (see e.g., Arthritis & Rheumatism (1996) Vol. 39, No. 9 (supplement), S308); interleukin-17 inhibitors (see e.g., Arthritis & Rheumatism (1996) Vol. 39, No. 9 (supplement), S120); gold; penicillamine; chloroquine; hydroxychloroquine; chlorambucil; cyclophosphamide; cyclosporine; total lymphoid irradiation; anti-thymocyte globulin; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligodeoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al. (1995) Rheum. Dis. Clin. North Am. 21:759–777); auranofin; phenylbutazone; meclofenamic acid; flufenamic acid; intravenous immune globulin; zileuton; mycophenolic acid (RS-61443); tacrolimus (FK-506); sirolimus (rapamycin); amiprilose (therafectin); cladribine (2-chlorodeoxyadenosine); and azaribine. Preferred combinations include one or more IL-21 antagonists in combination with methotrexate or leflunomide, and in moderate or severe rheumatoid arthritis cases, cyclosporine.

Preferred examples of inhibitors to use in combination with UL-21/IL-21R to treat arthritic disorders include TNF antagonists (e.g., chimeric, humanized, human or in vitro generated antibodies, or antigen-binding fragments thereof, that bind to TNF; soluble fragments of a TNF receptor, e.g., p55 or p75 human TNF receptor or derivatives thereof, e.g., 75 kdTNFR-IgG (75 kD TNF receptor-IgG fusion protein, Enbrel™, p55 kD TNF receptor-IgG fusion protein; TNF enzyme antagonists, e.g., TNFa converting enzyme (TACE) inhibitors); antagonists of IL-12, IL-15, IL-17, IL-18, IL-22; T cell and B cell depleting agents (e.g., anti-CD4 or anti-CD22 antibodies); small molecule inhibitors, e.g., methotrexate and leflunomide; sirolimus (rapamycin) and analogs thereof, e.g., CCI-779; Cox-2 and cPLA2 inhibitors; NSAIDs; p38 inhibitors, TPL-2, Mk-2 and NFkb inhibitors; RAGE or soluble RAGE; P-selectin or PSGL-1 inhibitors (e.g., small molecule inhibitors, antibodies thereto, e.g., antibodies to P-selectin); estrogen receptor beta (ERB) agonists or ERB-NFkb antagonists. Most preferred additional therapeutic agents that can be co-administered and/or co-formulated with one or more IL-21/IL-21R antagonists include one or more of: a soluble fragment of a TNF receptor, e.g., p55 or p75 human TNF receptor or derivatives thereof, e.g., 75 kdTNFR-IgG (75 kD TNF receptor-IgG fusion protein, Enbrel™; methotrexate, leflunomide, or a sirolimus (rapamycin) or an analog thereof, e.g., CCI-779.

Non-limiting examples of agents for treating or preventing multiple sclerosis with which an IL-21-/IL21R binding agent can be combined include the following: interferons, e.g., interferon-alpha1a (e.g., Avonex™; Biogen) and interferon-1b (Betaseron™; Chiron/Berlex); Copolymer 1 (Cop-1; Copaxone™; Teva Pharmaceutical Industries, Inc.); hyperbaric oxygen; intravenous immunoglobulin; clabribine; TNF antagonists as described herein; corticosteroids; prednisolone; methylprednisolone; azathioprine; cyclophosphamide; cyclosporine; methotrexate; 4-aminopyridine; and tizanidine. Additional antagonists that can be used in combination with IL-21 include antibodies to or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. IL-21 antagonists as described herein can be combined with antibodies to cell surface molecules such as CD2, CD3, CD4, CD8, CD25, CD28, CD30, CD40, CD45, CD69, CD80, CD86, CD90 or their ligands. The IL-21 antagonists may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines as described herein, IL-Ib converting enzyme inhibitors (e.g., Vx740), anti-P7s, PSGL, TACE inhibitors, T-cell signaling inhibitors such as kinase inhibitors, metal loproteinase inhibitors, sulfasalazine, azathloprine, 6-mercaptopurines, angiotensin converting enzyme inhibitors, soluble cytokine receptors and derivatives thereof, as described herein, and anti-inflammatory cytokines (e.g. IL-4, IL-10, IL-13 and TGF).

Preferred examples of therapeutic agents for multiple sclerosis with which the IL-21 antagonists can be combined include interferon-b, for example, IFNb-1a and IFNb-1b; copaxone, corticosteroids, IL-I inhibitors, TNF inhibitors, antibodies to CD40 ligand and CD80, IL-12 antagonists.

Non-limiting examples of agents for treating or preventing inflammatory bowel disease or Crohn's disease with which an IL-21/IL-21R antagonist can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1 monoclonal antibodies; anti-IL-6 monoclonal antibodies; growth factors; elastase inhibitors; pyridinyl-imidazole compounds; TNF antagonists as described herein; IL-4, IL-10, IL-13 and/or TGFb cytokines or agonists thereof (e.g., agonist antibodies); interleukin-11; glucuronide- or dextran-conjugated prodrugs of prednisolone, dexamethasone or budesonide; ICAM-1 antisense phosphorothioate oligodeoxynucleotides (ISIS 2302; Isis Pharmaceuticals, Inc.); soluble complement receptor 1 (TP10; T Cell Sciences, Inc.); slow-release mesalazine; methotrexate; antagonists of Platelet Activating Factor (PAF); ciprofloxacin; and lignocaine.

In one embodiment, an IL-21/IL21R antagonists can be used in combination with one or more antibodies directed at other targets involved in regulating immune responses, e.g., transplant rejection or graft-v-host disease. Non-limiting examples of agents for treating or preventing immune responses with which an IL-21/IL21R antagonist of the invention can be combined include the following: antibodies against cell surface molecules, including but not limited to CD25 (interleukin-2 receptor-a), CD11a (LFA-1), CD54 (ICAM-1), CD4, CD45, CD28/CTLA4, CD80 (B7-1) and/or CD86 (B7-2). In yet another embodiment, an IL-21/IL21R antagonist is used in combination with one or more general immunosuppressive agents, such as cyclosporin A or FK506.

Another aspect of the present invention accordingly relates to kits for carrying out the combined administration of the IL-21/IL21R antagonists with other therapeutic compounds. In one embodiment, the kit comprises one or more binding agents formulated in a pharmaceutical carrier, and at least one agent, e.g., therapeutic agent, formulated as appropriate, in one or more separate pharmaceutical preparations.

Assays for Measuring the Activity of IL-21/IL21R Agonists as Immune Activators

The activity of IL-21/IL21R agonists as activators of an immune system can, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowman et al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E.e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. U.S.A. 88:7548–7551, 1991.

Assays for Measuring the Activity of IL-21/IL21R Agonists or Antagonists as Modulators of Cytokine Production and Cell Proliferation/Differentiation The activity of IL-21/IL21R agonists or antagonists as modulator of cytokine production and cell proliferation/differentiation can be tested using any one of a number of routine factor dependent cell proliferation assays for cell lines including, without limitation, 32D, DA2, DA1G, T10, B9, B9/11, BaF3, MC9/G, M+(preB M+), 2E8, RB5, DA1, 123 T1165, HT2, CTLL2, TF-1, Mo7e and CMK.

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152:1756–1761, 1994.

Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E.e.a. Coligan eds. Vol 1 pp. 3.12.1–3.12.14, John Wiley and Sons, Toronto. 1994; and Measurement of mouse and human Interferon .gamma., Schreiber, R. D. In Current Protocols in Immunology. J. E. e. a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e. a. Coligan eds. Vol 1 pp. 6.3.1–6.3.12, John Wiley and Sons, Toronto. 1991; deVries et al., J. Exp. Med. 173:1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e. a. Coligan eds Vol 1 pp. 6.6.1–6.6.5, John Wiley and Sons, Toronto. 1991; Smith et al., Proc. Natl. Acad. Sci. U.S.A. 83:1857–1861, 1986; Measurement of human Interleukin 11—Bennett, F., Giannotti, J., Clark, S. C. and Turner, K. J. In Current Protocols in Immunology. J. E. e. a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e. a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. U.S.A. 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Assays for Measuring the Activity of IL-21/IL21R Agonists or Antagonists as Regulators of Hematopoiesis IL-21/IL21R agonists or antagonists may be useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in supporting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

The activity of the IL-21- or IL-21R binding agents may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lympho-hematopoiesis) include, without limitation, those described in: Methylcellulose colony forming assays, Freshney, M. G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. U.S.A. 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

The invention will be further illustrated in the following non-limiting examples.

EXAMPLE 1

Isolation and Characterization of Murine MU-1 cDNAs:

A partial fragment of the murine homolog of the Mu-1 receptor was isolated by PCR using oligonucleotides derived from the human sequences. cDNA was prepared from RNA isolated from 17 day old murine thymus and from the murine 2D6 T cell line. A DNA fragment of approximately 300 nucleotides was amplified from the cDNA by PCR with the following oligonucleotides, corresponding to regions 584–603 and 876–896, respectively, of the human cDNA sequence in FIG. 1 (corresponding to SEQ ID NO:1):

```
AGCATCAAG   CCGGCTCCCCC   (5p)   (SEQ ID NO:11)

CTCCATTCAC  TCCAGGTCCC    (3p)   (SEQ ID NO:12)
```

Amplification was carried out using Taq polymerase in 1×Taq buffer containing 1.5 mM of magnesium chloride for 30 cycles at 94° C. for one minute, 50° C. for 1 minute, and 72° C. for one minute. The DNA sequence of this fragment was determined, and two oligonucleotides were derived from an internal portion of this fragment with the following sequences:

```
TTGAACGTGACTGRGGCCTT     (5P)   (SEQ ID NO:13)

TGAATGAAGTGCCTGGCTGA     (3P)   (SEQ ID NO:14)
```

The oligonucleotides were used to amplify an internal 262 nucleotide fragment of the original PCR product (corresponding to nucleotides 781–1043 of the murine cDNA sequence of FIG. 1, and SEQ ID NO:9) to use as a hybridization probe to screen a cDNA library isolated from the 2D6T T cell line. Filters were hybridized at 65° C. using standard 5×SSC hybridization conditions and washed into SSC at 65° C. Twenty clones were hybridizes to the probe in a screen of 426,000 clones. DNA sequence was determined from two independent clones. Full length sequence of clone #6 confirmed that it was the full-length murine homolog of human MU-1 (SEQ ID NO:9).

The full-length nucleotide sequence of murine MU-1 is shown in FIG. 1 (corresponding to SEQ ID NO:9). The nucleotide sequence has a predicted leader sequence at nucleotides 407–464, coding sequence at 407–1993, and a termination codon at nucleotides 1994–1997. Nucleotides 1–406 correspond to the 5' untranslated region and nucleotides 1998–2868 correspond to the 3' untranslated region.

The predicted protein sequence of murine MU-1 is shown in FIG. 2 (corresponding to SEQ ID NO:10). This murine MU-1 protein contains a predicted leader sequence determined by SPScan (score=10.1)(corresponding to amino acids 1–19 of SEQ ID NO:10), and a predicted transmembrane domain (corresponding to amino acids 237–253 of SEQ ID NO:10). Predicted signaling motifs include the following regions: Box 1: amino acids 265–274 of SEQ ID NO:10, Box 2: amino acids 310–324 of SEQ ID NO:10, six tyrosine residues at positions 281, 319, 361, 297, and 510 of SEQ ID NO:10. Potential STAT docking sites include: STAT5, EDDGYPA (SEQ ID NO:20), STAT3, YLQR.

The oligonucleotides were used to amplify an internal 262 nucleotide fragment of the original PCR product (corresponding to nucleotides 781–1043 in of the murine cDNA sequence of FIG. 1, and SEQ ID NO:9) to use as a hybridization probe to screen a cDNA library isolated from the 2D6 T cell line. Filters were hybridized at 65° C. using standard 5×SSC hybridization conditions and washed into SSC at 65° C. Twenty clones were isolated that hybridized to the probe in a screen of 426,000 clones. DNA sequence was determined from two independent clones. Full length sequence of clone #6 confirmed that it was the full-length murine homolog of human MU-1 (SEQ ID NO:9).

The full-length nucleotide sequence of murine MU-1 is shown in FIG. 1 (corresponding to SEQ ID NO:9). The nucleotide sequence has a predicted leader sequence at nucleotides 407–464, coding sequence at nucleotides 407–1993, termination codon at nucleotides 1994–1997. Nucleotides 1–406 correspond to the 5' untranslated region and nucleotides 1998–2628 correspond to the 3' untranslated region.

The predicted protein sequence of murine MU-1 is shown in FIG. 2 (corresponding to SEQ ID NO: 10). This murine MU-1 protein contains a predicted leader sequence determined by SPScan (score=10.1) (corresponding to amino acids 1–19 of SEQ ID NO: 10), and a predicted transmembrane domain (corresponding to amino acids 237–253 of SEQ ID NO:10). Predicted signaling motifs include the following regions: Box 1: amino acids 265–274 of SEQ ID NO: 10, Box 2: amino acids 310–324 of SEQ ID NO: 10, six tyrosine residues at positions 281, 319, 361, 368, 397, and 510 of SEQ ID NO:10. Potential STAT docking sites include: STAT5: EDDGYPA (SEQ ID NO:20); STAT 3:YLQR.

EXAMPLE 2

Comparison of Human and Murine MU-1:

The GAP algorithm was used to compare the human and murine MU-1 amino acids. A comparison of the murine and human predicted protein sequences is shown in FIG. 4. The amino acids were 65.267% identical using the GAP algorithm. The alignment was generated by BLOSUM62 amino acid substitution matrix (Henikoff, S. and Henikoff, J. G. (1992)). Amino acid substitution matrices from protein blocks (Proc. Natl. Acad. Sci. USA 89: 10915–10919). Gap parameters=Gap Weight: 8, Average Match=2.9 12, Length Weight=2, Average Mismatch=−2.003. Percent Similarity=69.466.

A comparison of the human and murine CDNA nucleotide sequences is shown in FIG. 3. The DNA sequences are 66.116% identical when aligned using the GAP algorithm. Gap Parameters: Gap Weight=50, Average Match 10.000, Length Weight=3, Average Mismatch=0.000. Percent Similarity=66.198.

Both human and mouse MU-1 proteins are members of the Type 1 cytokine receptor superfamily. Evaluation of the sequence of both murine and human MU-1 reveals the presence of potential Box-i and Box-2 signaling motifs. Six tyrosine residues are present in the cytoplasmic domain, and could also be important in signaling functions of MU-1. Comparison of the sequences of MU-1 with other members of the family suggested the presence of potential docking sites for STAT 5 and STAT 3.

EXAMPLE 3

Determination of STAT Signaling Pathways used by Human MU-1:

BAF-3 cells were engineered to express a chimeric cytokine receptor consisting of the extracellular domain of the human EPO receptor and the intracellular domain of the MU-1 receptor. BAF-3 cells that expressed huEPORJMU-1(cyto) chimeric receptors proliferated in response to human soluble EPO. These cells were analyzed to determine which STAT molecules were phosphorylated in response to EPO signaling. Briefly, control unmodified parental BAF-3 cells and EPOR/MU chimeric BAF-3 cells were rested from IL-3 containing growth medium, and restimulated with either IL-3 or EPO for 0, 15, 30 and 60 minutes. The cells were pelleted and resuspended in ice cold lysis buffer containing orthovanadate, to preserve phosphorylated tyrosines. Equal amounts of cell lysate were electrophoresed by SDS-PAGE and blotted onto nitrocellulose membranes for western analysis. Duplicate blots were stained for phosphorylated and nonphosphoraled forms of STAT 1, 3, 5, and 6 by using antibodies specific for each form of the STAT molecule. HELA cells, non-activated and activated with alpha-interferon were used as positive controls.

These results indicated that under these specific conditions, signaling through MU-1 results in the phosphorylation of STAT 5 at all time-points tested (1=0, T=15', T=30', 1=60'). Treatment of controls or the chimeric BAF-3 cells with IL-3 resulted in phosphorylation of STAT 3, but not STAT 1 or 5.

EXAMPLE 4

Tissue Expression of Murine and Human MU-1

Northern Analysis

Northern blots of polyA+ RNA from various tissues (Clonetech, Palo Alto, Calif.) were performed as recommended by the manufacturer. For the murine blots, a 262 nucleotide fragment corresponding to nucleotides 781–1043 of FIG. 1 and SEQ ID NO:9 was used for hybridization.

A single transcript of murine MU-1 was detected in adult murine spleen, lung, and heart tissues. The larger transcript observed in human tissues was not observed in mouse tissues.

Two transcripts of human MU-1 were detected in adult human lymphoid tissues, PBLs, thymus, spleen and lymph node, and in fetal lung.

In Situ Hybridization

In situ hybridization studies were performed by Phylogency Inc. of Columbus, Ohio (according to the method of Lyons et al., 1990, J. Cell. Biol: 111:2427–2436.) Briefly, serial 5–7 micron paraffin sections were deparaffinized, fixed, digested with proteinase K, treated with tri-ethanolamine and dehydrated. cRNAs were prepared from linearized cDNA templates to generate antisense and sense probes. The cRNA transcripts were synthesized according to manufacturer's conditions (Ambion) and labeled with 35S-UTP. Sections were hybridized overnight, stringently washed and treated with RNAase A and dipped in nuclear track emulsion and exposed for 2–3 weeks. Control sections were hybridized with sense probes to indicate the background level of the procedure. The murine probe consisted of a n 186 bp fragment corresponding to nucleotides 860–1064 (SEQ ID NO:9). The human probe was a 23 bp PCR product generated from human MU-1 DNA.

Murine MU-1 expression was observed in the lymph nodes of the adult small intestine at germinal centers and muscular is external. Specialized lymph nodes and Peyers patches also exhibited murine MU-1 expression.

Human MU-1 expression was detected at germinal centers of the lymph nodules in the cortex. The medulla, which contains macrophages, was negative for human MU-1. In human spleen, human MU-1 expression was detected in the regions of white pulp but not red pulp.

EXAMPLE 5

Expression of Human MU-1 in Cells and Cell Lines:

RNAse protection analysis was performed on resting and activated human T cells and the B cell lines, Raji and RPMI 8866, and the I cell line Jurkat. Human T cells were activated with anti-CD3 and anti-CD28. The cell lines were activated by Phorbol ester and ionomycin. MU-1 riboprobe-producing plasmid was constructed by inserting a 23 bp PCR product (PCR was performed by using 5' primer CACAAAGCTTCAGTATGAGCTGCAGTA-CAGGAACCGGGGA (SEQ ID NO: 15) and 3' primer CACAGGATCCCTTTAACTCCTCT-GACTGGGTCTGAAAGAT (SEQ ID NO:16)) into the BamH I and HindIII sites of pGEM3zf(–) (Promega, Madison, Wis.) vector. To make the riboprobe, the riboprobe-producing plasmid was linearized with HindIII. The resulting DNA was phenol/chloroform extracted and precipitated with ethanol. T7 RNA polymerase was used to make the riboprobe according to the protocol suggested by the vendor (PharMingen, San Diego, Calif.). The RNAse protection assay was performed by using PharMingen's RiboQuant Multi-Probe Ribonuclease Protection Assay system. 2.0ug of total RNA were included in each RPA reaction, after RNAse digestion, the protected riboprobes were run on a QuickPoint rapid nucleic acid separation system (Novex, San Diego, Calif.). Gels were dried and exposed according to the suggestion of the vendor.

Human MU-1 RNA is upregulated in anti-CD3+anti-CD28 stimulated human purified CD3+ cells when compared with unstimulated populations. MU-1 is also upregulated upon restimulation in Th1 and Th2-skewed T cell populations. The B cell lines, RPMI 8866 and Raji, constitutively express MU-1 while the Jurkat T cell line does not.

EXAMPLE 6

Binding of Human MU-1 to Known Cytokines

Both human and murine Ig fusion proteins were constructed and immobilized on Biacore chips in an effort to identify the ligand for MU-1. A variety of cell culture conditioned media as well as a panel of known cytokines were evaluated for binding to MU-1. Some cytokines were also tested in combination with other receptor chains in the family to consider the possibility that MU-1 may require a second receptor chain for ligand binding. The following cytokines were tested and found to be negative for MU-1 binding: mIL-2, hIL-2, hIL-i5, mIL-7, TSLP, TSLP+IL7, TSLP+IL7R, TSLP+IL7g, TSLP+IL-2, TSLP+1L2+IL2Rbeta, IL2Rbeta, IL2Rgamma, IL7R, IL2+2Rbeta, IL2+2Rgamma, IL1 5+IL2Rbeta, 1L15+2Rgamma, 1IL7+2Rgamma, IL2+IL7R, IL1 5+IL7R, IL7+IL7R. Known receptors have been immobilized as well and tested for MUFc binding with negative results. IL-IS will bind to IL2Rb but not IL2Rg or MUFc.

EXAMPLE 7

Effect of Modulation of IL-21/IL-21R Pathway on the Severity of Symptoms in Collagen-Induced Arthritis (CIA) Mice This example shows that IL-21R antagonists, e.g., IL-21R-Ig fusion proteins (murine IL21RFc protein or "muIL21RFc") or anti-IL21R antibodies, ameliorate symptoms in a collagen-induce arthritis (CIA) murine model. In contrast, administration of IL-21 exacerbates the arthritic symptoms in CIA mice.

Figure 16:
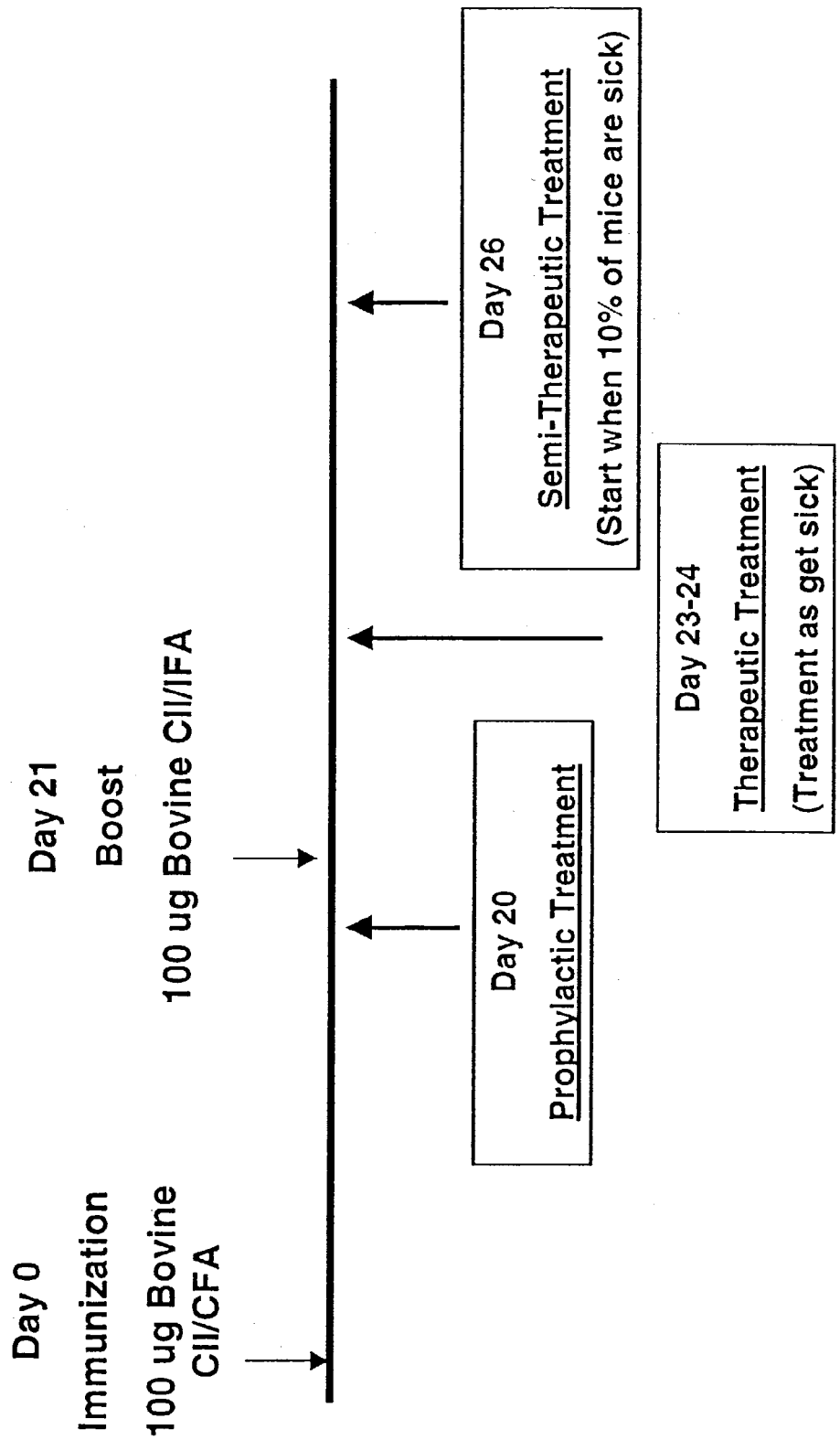
FIG. 16 is a timetable summarizing the prophylactic, therapeutic and semi-therapeutic treatment schedules for the experiments using collagen-induced arthritis (CIA) mouse models.

Male DBA/1 (Jackson Laboratories, Bar Harbor, Me.) mice were used for all experiments. Arthritis was induced with the use of bovine collagen type II (Chondrex, Redmond, Wash.). Bovine collagen type II (Chondrex, Redmond, Wash.) was dissolved in 0.1 M acetic acid and emulsified in an equal volume of CFA (Sigma) containing 1 mg/ml *Mycobacterium tuberculosis* (strain H37RA). 100 µg of bovine collagen was injected subcutaneously in the base of the tail on day 0. On day 21, mice were injected subcutaneously, in the base of the tail, with a solution containing 100 µg of bovine collagen in 0.1M acetic acid that had been mixed with an equal volume of Incomplete Freund's adjuvant (Sigma). Naïve animals received the same sets of injections, minus collagen. The dosing protocol is shown schematically in FIG. 16. MuIL21RFc was administered prophylactically or therapeutically to DBA mice. In the therapeutic regimen, treatment was initiated if disease was observed for two consecutive days in a mouse.

Mice were monitored at least three times a week for disease progression. Individual limbs were assigned a clinical score based on the index: 0=normal, no swelling; 1=visible erythema accompanied by 1–2 swollen digit, or mild swelling in ankle; 2=pronounced erythema, characterized by mild to moderate paw swelling and/or two swollen digits; 3=extensive swelling of the entire paw, i.e., extending into ankle or wrist joint; 4=resolution of swelling, ankylosis of the paw; difficulty in use of limb or joint rigidity. Thus, the sum of all limb scores for any given mouse yielded a maximum total body score of 16.

At various stages of disease, animals were euthanized, tissues were harvested and paws were fixed in 10% formalin for histology or 4% paraformaldehyde, pH 7.47, decalcified in 20% EDTA (pH 8.0) and embedded in paraffin for in situ hybridization. Using light microscopy the paws were scored on a 5-grade scoring method (0–4) to characterize the intensity and extent of arthritis. Inflammatory infiltrates were used for scoring in addition to other changes related to the inflammation, such as pannus formation, fibrous of the synovial membrane, articular cartilage erosin and/or sub-chondral bone destruction. Histology grades were determined using readings of individual paws: NAD=0 or nothing abnormal discovered; 1=Slight to moderate; 2: Mild to moderate; 3: Marked and 4:Massive.

A reduction in the severity of the symptoms was observed after prophylactic treatment of CIA mice using muIL21RFc (100 µg or 200 µg) administered intraperitoneally (ip) every other day starting one day before the collagen boost (data not shown).

Figure 17:
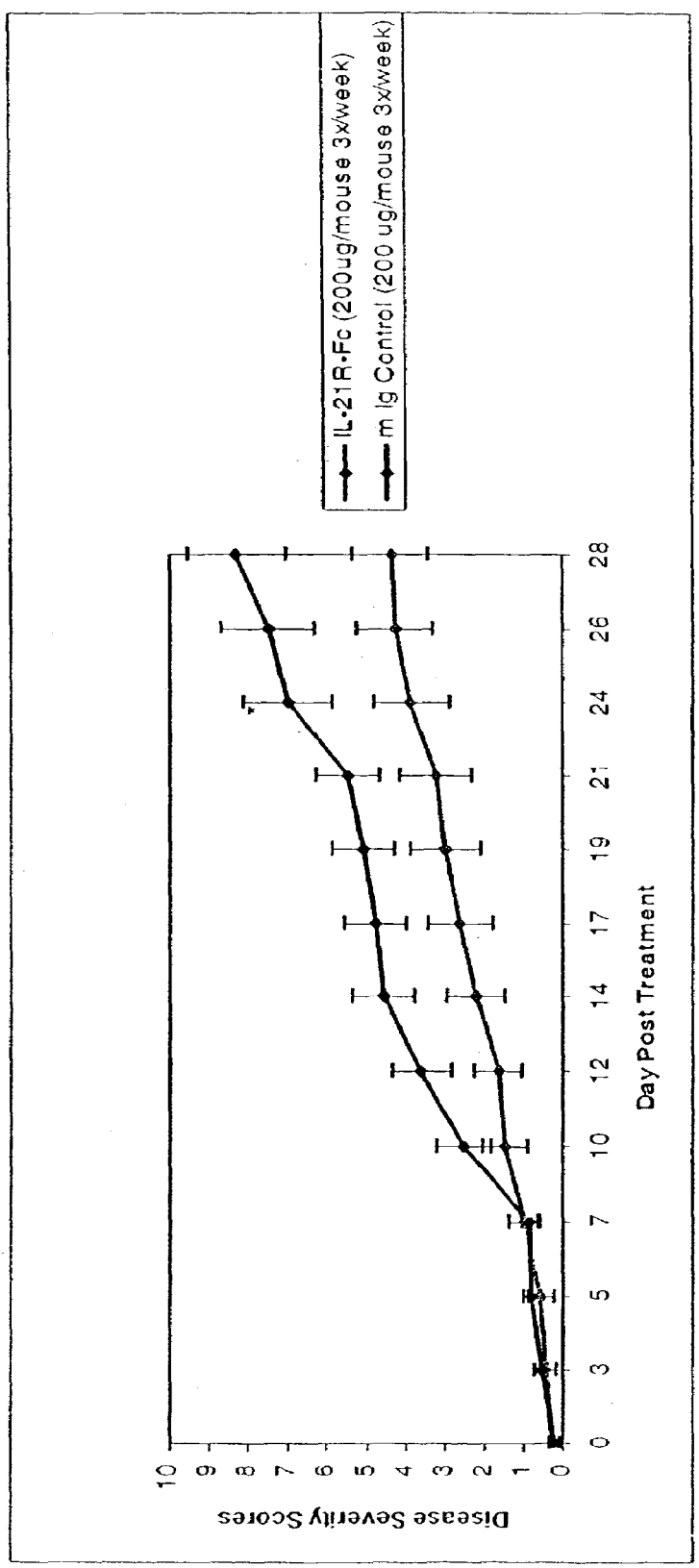
FIG. 17 is a graph depicting the effects of muIL21RFc (200 μg/mouse 3×/week) on a semi-therapeutic CIA mouse as a function of days post treatment. Mouse Ig (200 μg/mouse 3×/week) was used as a control.

The effects of muIL21RFc (200 µg/mouse 3×/week) on a semi-therapeutic CIA mouse as a function of day post treatment are shown in FIG. 17. Mouse Ig (200 µg/mouse 3×/week) was used as a control. A reduction in the severity score is shown starting from day 7 post treatment.

Figure 18:
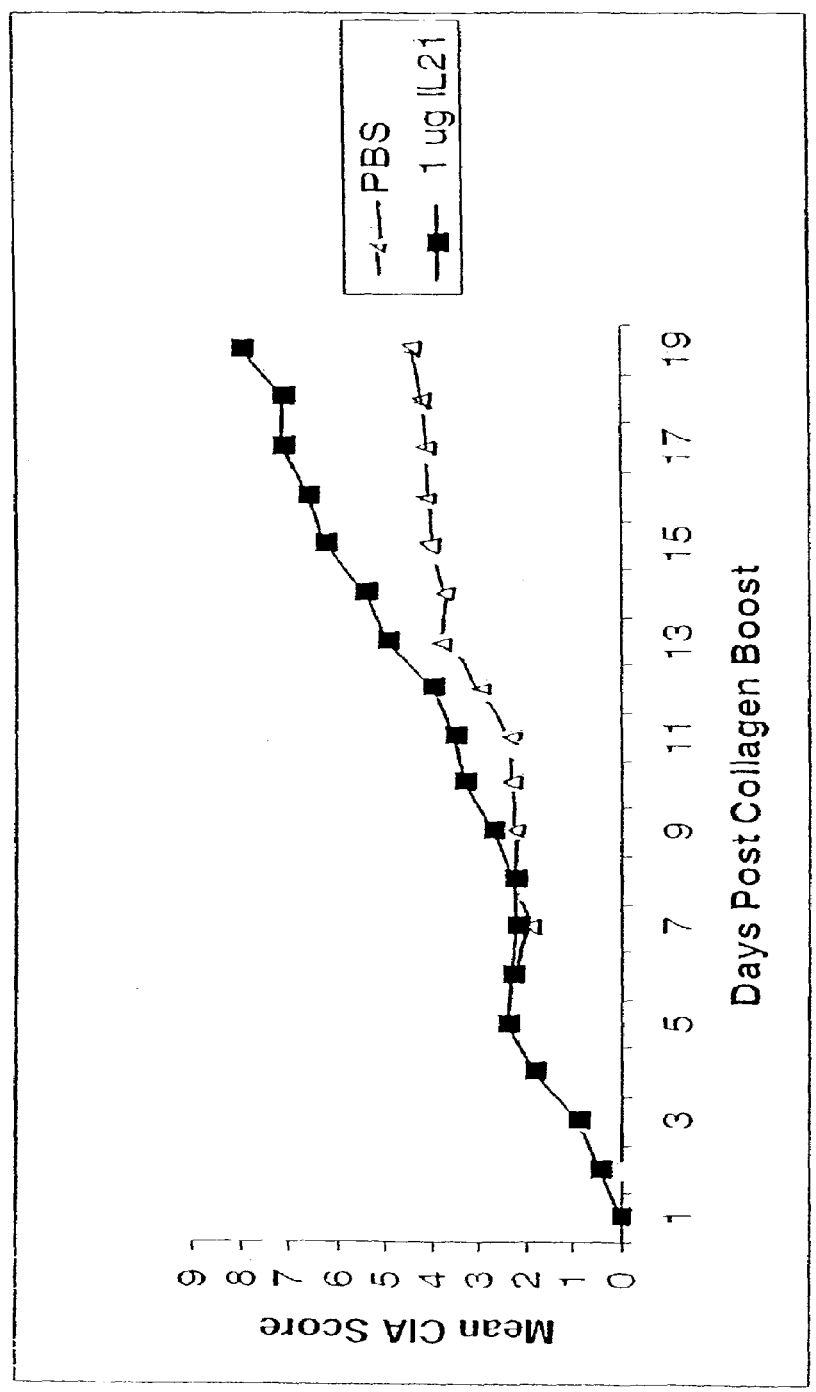
FIG. 18 is a graph depicting the effects of murine IL-21 on mean CIA score as a function of days post collagen boost. Mice were injected with 1 μg of murine IL21 intraperitoneally when presenting a total body score of 2–4.

Administration of IL-21 exacerbates the arthritic symptoms in CIA mice. FIG. 18 is a graph depicting the mean CIA score as a function of days post collagen boost. Mice administered with 1 mg of murine IL-21 intraperitoneally (ip) showed higher CIA scores that control PBS-treated mice.

These experiments demonstrate that administration of an IL-21R antagonist, e.g., IL-21R-Fc fusion proteins, to CIA mice either prophylactically or semi-therapeutically significantly ameliorated arthritic symptoms. In contrast, administration of IL-21 exacerbates the symptoms.

EXAMPLE 8

In situ Hybridization of IL-21R Transcripts

Figure 19:
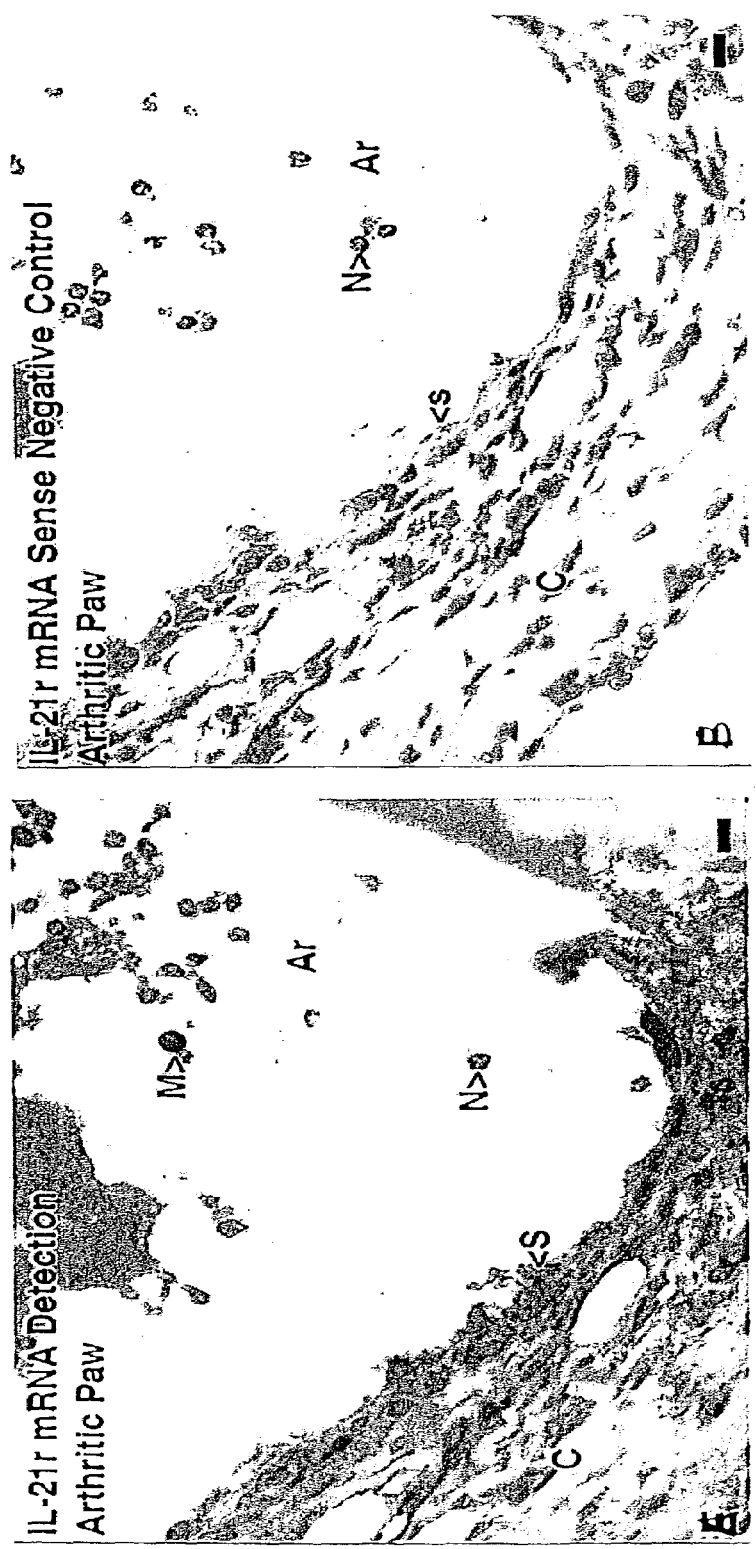
FIG. 19, panels A–B, are photographs showing increased expression of IL-21R mRNA in arthritic paws of mice with CIA (panel A) compared to negative controls (panel B).

The expression of IL-21R mRNA in arthritic paws of mice with CIA was determined. Anti-sense murine IL-21R riboprobes were used (FIG. 19, panel A); sense probes were used as negative controls (FIG. 19, panel B).

Digoxygenin labeled probes were prepared with the use of a DIG RNA labeling mix (Roche Diagnostics, Mannheim, Germany), as described by the manufacturer. Expression of IL-21 receptor mRNA was detected in macrophages, neutrophils, fibroblasts, a subpopulation of lymphocytes, synoviocytes and epidermis (FIG. 19, panel A). Decreased staining was seen in the control paws or with sense probes (FIG. 19, panel B). mIL21R mRNA positive cells were: neutrophils (N), and macrophages (M). In situ hybridization shows enhanced expression of IL-21R in the paws of arthritic mice.

EXAMPLE 9

In vivo Activation of IL-21 Receptor Generates Potent Anti-Tumor Responses

This example shows that administration of IL-21-expressing tumor cells enhances anti-tumor responses in vivo in both immunogenic and non-immunogenic tumor models. $CD8^+$ T cells and NK cells are necessary for tumor destruction and subsequent development of tumor antigen specific T cells. IL-21 present at the tumor microenvironment potentiates both innate and adaptive immunity in vivo anti-tumor responses.

Experimental Procedures

Mice. Female C57BL/6, Balb/C, $IFN\gamma^{-/-}$ and $IL-10^{-/-}$ mice in C57BL/6 background were purchased from Jackson Laboratories (Bar Harbor, Me.). C57BL/6 scid and nude mice were purchased from Taconic (Germantown, N.Y.). $IL-21R^{-/-}$ mice were generated at Wyeth Research, MA. and maintained at Charles Rivers Laboratories (Andover, Mass.) (Kasaian, M. T. et al. (2002) *Immunity.* 16:559–569). Mice were maintained and treated in accordance with National Institutes of Health and American Association of Laboratory Animal Care regulations.

Tumor cell lines and reagents. Two tumor cells lines, B16F1 melanoma and MethA fibrosarcoma, were used in the experiments described herein. B16F1 melanoma and MethA fibrosarcoma cells have been extensively used in tumor vaccination models to study the in vivo anti-tumor effect of various cytokines. B16F1 tumor cells are poorly immunogenic, in that previous vaccination with irradiated wild-type tumor cells only protects 20% of vaccinated mice against subsequent live B16F1 challenge (Dranoff, G. et al. (1993) *PNAS* 90:3539–3543). In contrast, MethA, a methycholantheren induced fibrosarcoma, are highly immunogenic (i.e., vaccination with irradiated MethA cells leads to almost 100% protection against subsequent live MethA challenge).

B16F1 melanoma cells were maintained in culture in DMEM medium supplemented with 10% heat in-activated fetal bovine serum, 2% glutamine, and 1% penicillin-streptomycin. MethA fibrosarcoma cells were maintained by intraperitoneal passage in Balb/C mice. B16F1 melanoma specific TRP-2 (SVYDFFVWL, SEQ ID NO:40) (van Elsas, A. et al. (2001) *Journal of Experimental Medicine* 194: 481–489; Sutmuller, R. P. et al. (2001) *Journal of Experimental Medicine.* 194:823–832) and control peptide $OVA_{257-264}$ (SIINFEKL, SEQ ID NO:41) were synthesized at the Wyeth Research, Mass. Monoclonal Abs anti-CD3, anti-CD28 and rat IgG2a, and IL-2 cytokine used in this paper were all purchased from PharMingen (San Diego, Calif.).

Generation of IL-21 and green fluorescent protein (GFP) expressing tumor cells. B16F1 and MethA tumor cells were engineered to express IL-21 and GFP, or only GFP. Retroviral vectors encoding mIL21-IRES-GFP or IRES-GFP were constructed using GFP-RV vector (Ranganath, S. et al. (1998) *Journal of Immunology* 161:3822–3826). High titer retrovirus was obtained by transfecting 293-VSVg ecotropic packaging cell line (Ory, D. S. et al. (1996) *PNAS* 93:11400–11406). Spin infections were performed at 1800 rpm for 40 minutes at room temperature. Cells were infected 3 times. Tumor cells expressing GFP were enriched by flow sorting and the purity of GFP expressing cells was greater than 90%.

In vivo tumor studies. C57BL/6 mice were shaved on the back and injected i.d. with $10^5$ B16F1-IL-21 or control B16F1-GFP. Balb/C mice were injected with either $10^6$ or $2 \times 10^6$ MethA-IL-21 or control MethA-GFP cells. Tumor growth was monitored by measuring perpendicular diameters with a caliper. Mice were sacrificed when the tumors displayed severe ulceration or reached a size of 200 mm². In general, 10 mice per group were used in each experiment and representative results are shown from experiments repeated two or more times with similar results.

In vivo depletion studies. $CD4^+$ or $CD8^+$ T cell depletion was accomplished by i.p. injecting 400 µg per mouse of either anti-CD4 (GK1.5), anti-CD8 (53–6.7) mAbs or rat IgG isotype control for three consecutive days before tumor cell injection. Ab injections were continued every other day post tumor cell injection for 12 days. For NK cell depletion, 50 µl of rabbit anti-mouse/rat asialo GM1 polyclonal ab (Cedarlane, Ontario, Calif.) was injected i.p. one day before tumor cell injection. Mice similarly injected with normal rabbit serum were used for control. After tumor cell inoculation, antibody injections were continued twice per week for two weeks. T- and NK cell-depletion was confirmed in lymph nodes and spleens one day before tumor challenge (for T cells) or on the same day of tumor cell challenge (for NK cells) by flow cytometry using relevant antibodies. FACS analysis showed that greater than 99% of the relevant population of T cells or NK cells were depleted in mice treated with anti-CD4, anti-CD8, anti asialo GM 1. In contrast, mice treated with isotype controls displayed T lymphocyte profiles similar to the profiles of untreated mice.

IL-21 enzyme-linked immunosorbent assay (ELISA). Overnight supernatants from $10^6$ B16F1-IL-21, B16F1-GFP, MethA-IL-21 and MethA-GFP tumor cells were assayed for IL-21 levels by ELISA as detailed in Dunussi-Joannopoulos, K. et al. (1998) *Blood* 91:222–230. In brief, mMu1-mutm IgG2a (Wyeth Research, MA.) was used as coating antibody and anti-mouse IL-21 (R&D systems, Minneapolis, Minn.) was used as capture Ab. Purified mIL-21 (Wyeth Research, Mass.) (Kasaian, M. T. et al. (2002) supra) was used as control.

IL-21R mRNA expression detected by Taqman. RNA was isolated from different tumor cell lines according to the manufacturer's instructions (Promega, Madison, Wis.). mRNA extracted from splenocytes that had been activated with plate bound anti-CD3 (1 μg/ml) and anti-CD28 (1 μg/ml) mAbs (BD PharMingen) for 24 hours was used for positive control. Purified RNA was treated with DNase (Ambion Inc, Austin, Tex.) and adjusted to a concentration of 50 ng/μl before mRNA analysis by quantitative TaqMan polymerase chain reaction (PCR) analysis. IL-21R and cyclophylin-specific primer pairs and probes were designed using PrimerExpress software and were prepared by Wyeth Research (primers: 5'-GCCTTCTCAGGACGCTATGAT-3' (SEQ ID NO:43) and 5'-CCCTACAGCACGTAGTTGGA-3' (SEQ ID NO:44) and probe TCCTGGGACTCAGCT-TATGACGAACC) (SEQ ID NO:45). Standard curves for each gene were generated with RNA from known IL-21R expressing cells. mRNA expression in control and transduced cell lines was normalized based on cyclophilin expression in each cell line and the results are presented as relative units (R.U.) of mRNA.

Proliferation Assay. Splenocytes ($2\times10^5$ cells/well) from either C57BL/6 or Balb/C mice were stimulated with various concentrations of syngeneic irradiated tumor cells that expressed either GFP or IL21 in 96-well plates. $^3$H thymidine at 1 μCi/well (PerkinElmer Life Sciences, Boston, Mass.) was added during the last 6 hours of culture. After harvesting the supernatant onto glass fiber filter mats, $^3$H-thymindine incorporation was determined by liquid scintillation counting.

Elispot Assay. TRP-2 specific T cell responses were determined by IFN-γ Elispot kit (R&D systems) following manufacturers instructions. In brief, $2\times10^5$ to $4\times10^5$ of splenocytes (from tumor injected mice) in 200 μl complete medium containing 5 μg/ml of specific TRP-2 peptides (van Elsas, A. (2001) *J. Exp. Med.* 194:481–489) or non-specific OVA peptides and 20 U/ml murine IL-2 (PharMingen) were placed into each well. The plate was incubated for 24 hr at 37° C. in a $CO_2$ incubator. Plates were then incubated overnight at 4° C. with detection Ab, followed by 2-hr incubation with Streptavidin-alkaline phosphatase conjugate. Spots were visualized with 5-bromo-4 chloro-3' Indolylphosphate p-Toluidine Salt/Nitro Bluetetrazolium Chloride (BCIP/NBT) alkaline phosphotase substrate (R&D systems). Plates were washed with tap water and air-dried, and spots were counted with a stereomicroscope and re-calculated to per $10^6$ cells with background spots subtracted. Generally, less than 10 spots/well were detected when OVA peptide was used as antigen.

In vitro restimulation of splenocytes from tumor cell-inoculated mice. Tumor peptide specific T cell lines were generated as described in Bloom, M. B. et al. (1997) *J. Exp. Med.* 185:453–459. In brief, mice were inoculated with either B16F1-GFP or B16F1-IL-21 cells. After 8–11 days, splenocytes were harvested and cultured with 5 μg/ml of TRP-2 peptide (van Elsas, A et al. (2001) supra). On the third day of culture, 20 U/ml of IL-2 (BD PharMingen) was added to each culture. After 5 days, cells were used for $^{51}$Cr release assay.

CTL Assay. Cytotoxicity against targets was quantified using a 4-h $^{51}$Cr release assay. Briefly, RMA-S cells were pulsed with TRP-2 peptide at 10 μg/ml and labeled with $Na_2^{51}CrO4$ (PerkinElmer Life Sciences) for 1 hr at 37° C. After washing, $^{51}$Cr labeled target cells were incubated with T cell lines generated from C57BL/6 mice injected with tumor cells described earlier at different E:T ratios in 96-round bottom plates. After 4-hour incubation at 37° C., supernatants were collected and radioactivity was detected in a scintillation counter (Wallac, Turku, Finland). Percentage specific lysis was calculated as 100×[(release by CTL-spontaneous release)/(maximal release-spontaneous release)]. Maximal release was determined by the addition of 1% Triton X-100. Spontaneous release in the absence of CTL was generally less than 15% of maximal release.

IL-21 Transduced B16F1 and MethA Cells Secrete Biologically Functional IL-21

Figures 20A, 20B, 20C:
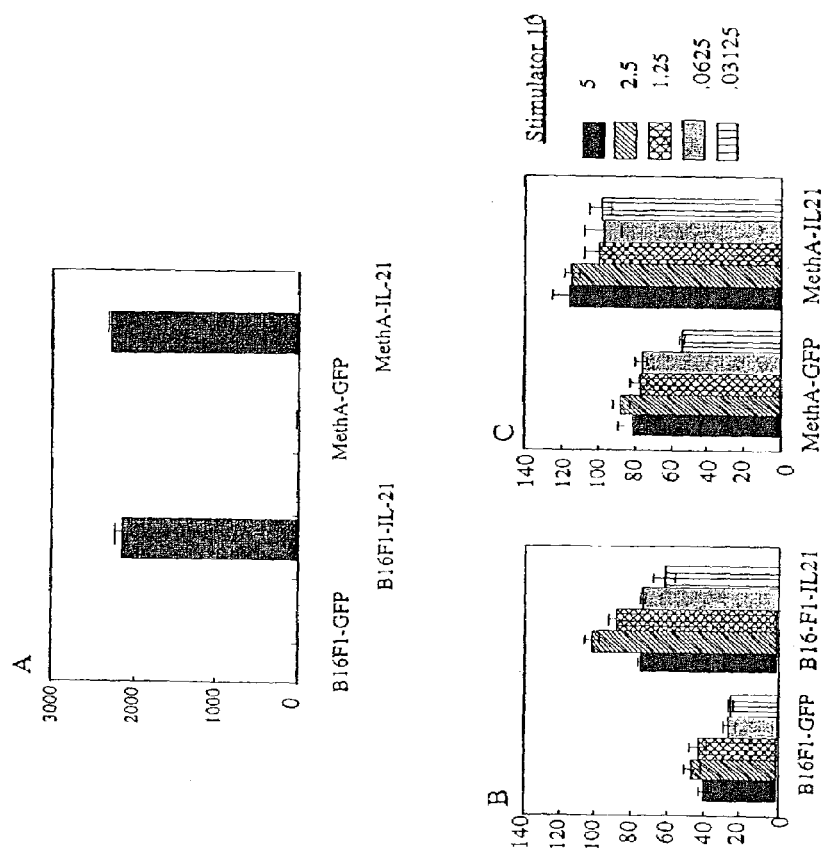
FIGS. 20A–20C are bar graphs depicting the level and biological activity of IL-21 secreted by IL-21-transduced B16F1 and MethA cells.

B16F1 and MethA tumor cells were transduced to express GFP plus IL-21 (B16F1/MethA-IL21) or GFP (B16F1/MethA-GFP), respectively. Overnight supernatants from $10^6$ of B16F1-IL-21, B16F1-GFP, MethA-IL-21 or MethA-GFP tumor cells were assayed by ELISA as described in Experimental Protocols, above. As shown in FIG. 20A, B16F1-IL-21 and MethA-IL-21 cells, but not B16F1-GFP or MethA-GFP tumor cells, secreted substantial amount of IL-21 in overnight cultures. To determine whether the IL-21 cytokine secreted by the transduced cells was biological functional, irradiated IL-21 or GFP expressing tumor cells were used to stimulate naïve syngenic splenocytes from C56BL/6 or Balb/C mice in the presence of sub-optimal amount of anti-CD3 (500 ng/ml) and anti-CD28 (10 μg/ml). As shown in FIGS. 20B and 20C, B16F1-IL-21 and MethA-IL-21 cells enhanced naïve splenocyte proliferation when compared with control GFP expressing cells at all concentrations tested. These results suggest that IL-21 secreted by transduced tumor cells is biologically functional.

IL-21 Does not Affect Tumor Cell Growth in Vitro

Figures 21A, 21B, 21C:
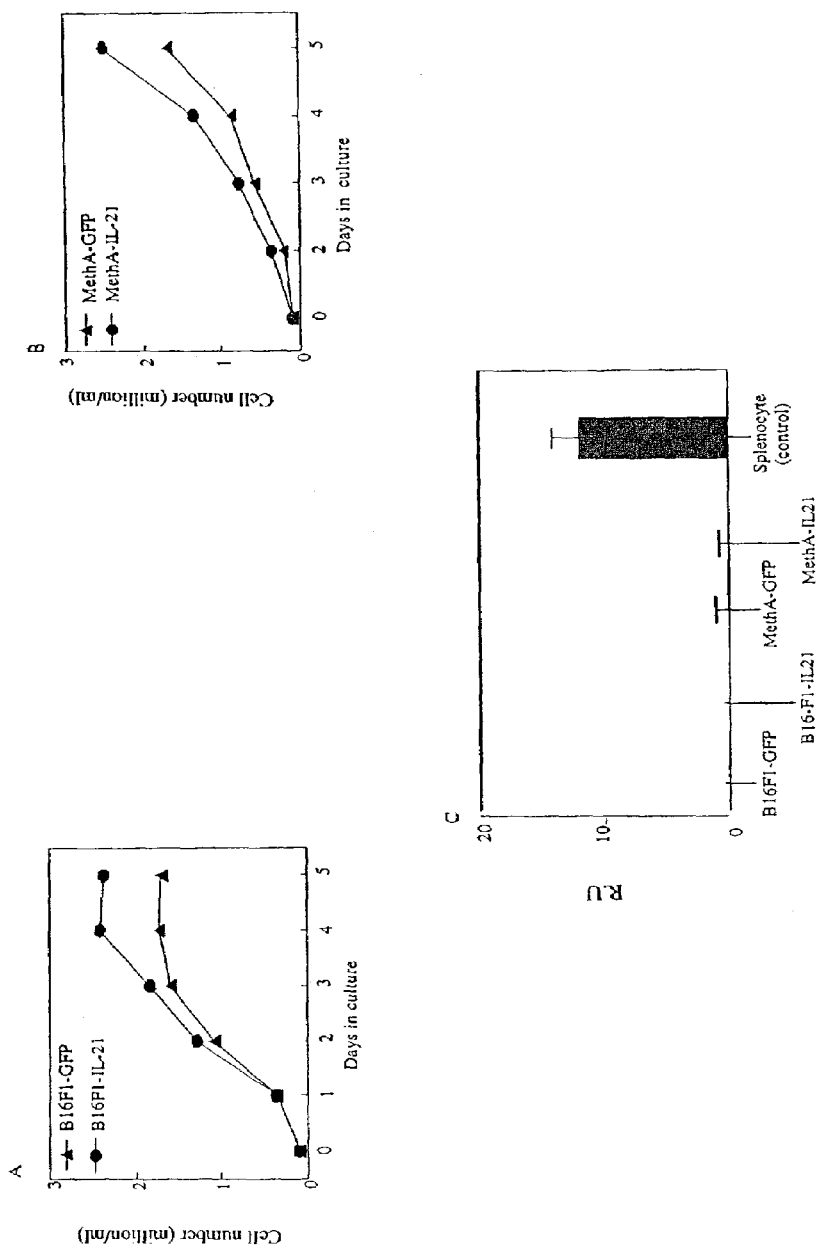
FIGS. 21A–21C are graphs depicting the in vitro growth characteristics of transduced tumor cells and evaluation of IL-21R expression.

The effect of IL-21 on the in vitro growth characteristics of transduced B1 6F1 and MethA cells was examined. B16F1-IL-21 and B16F1-GFP or MethA-IL-21 and MethA-GFP tumor cells were cultured at a concentration of $10^5/1.5$ ml culture media in 12-well plates. Cell numbers were monitored daily by trypan blue exclusion assay. The results are presented as means of duplicates. RNA from anti-CD3 and anti-CD28 mAb activated C57BL/6 splenocytes was used as positive control. Equal numbers of tumor cells were cultured in 12-well plates, and viable cell numbers were determined at various time points. As shown in FIGS. 21A and 21B, the growth kinetics of IL-21 producing tumor cells was very similar to that of the GFP expressing control tumor cells in a period of 5 days. This indicates that IL-21 did not have any apparent effect on the in vitro growth characteristics of transduced tumor cells. The unresponsiveness of tumor cells to IL-21 was further confirmed with the lack of the IL-21R expression by tumor cells in quantitative Taqman PCR analysis. FIG. 21C is a bar graph depicting quantitation of cyclophilin and IL-21R mRNA extracted from transduced tumor cells, determined by Taqman PCR. Expression of IL-21R mRNA in the transfected cells was normalized to cyclophilin values and expressed as relative unite (R.U.). RNA from anti-CD3 and anti-CD28 mAb activated C57BL/6 splenocytes was used as positive control.

IL-21 Inhibits Tumor Growth in Vivo

Figures 22A, 22B:
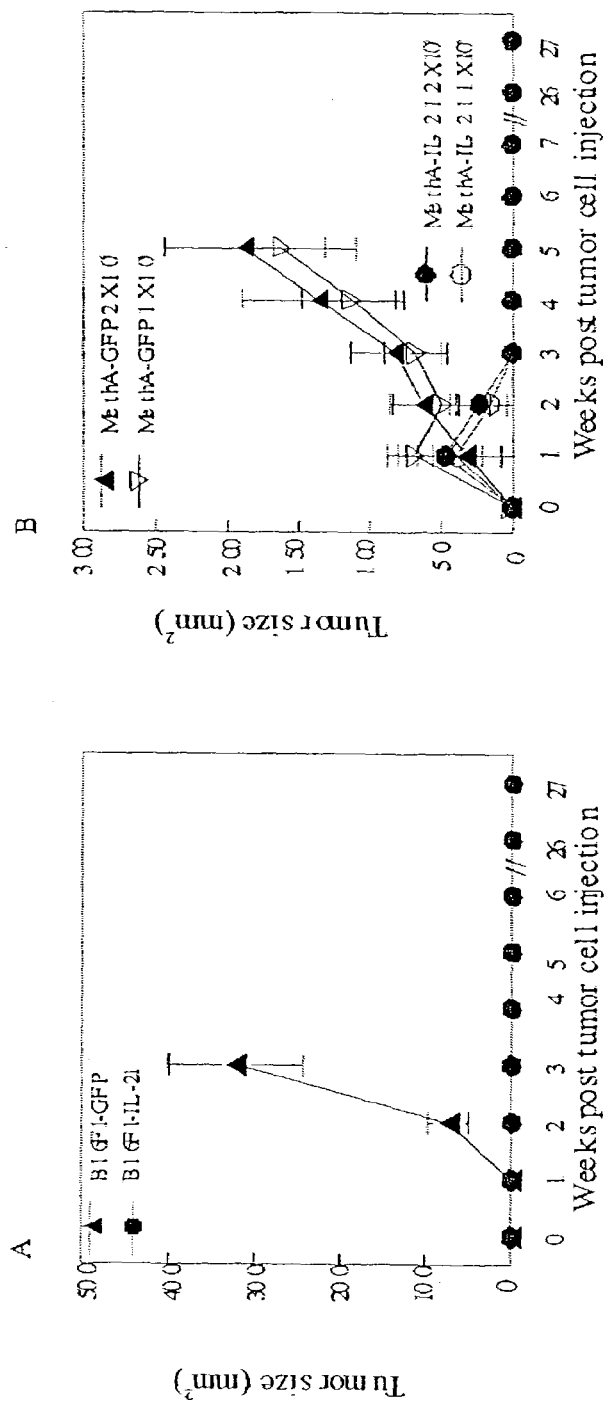
FIGS. 22A–22B are linear graphs depicting the in vivo growth characteristics of transduced tumor cells. IL-21 or GFP expressing tumor cells were injected in syngeneic naïve mice as indicated. Tumor size was scored by multiplying perpendicular diameters and was averaged for all mice in each group. (A) Tumor growth in C57BL/6 mice that were injected with $10^5$ of B16F1-IL-21 or GFP cells. (B) Tumor growth in Balb/C mice that were injected with either $1\times10^6$ or $2\times10^6$ of MethA-IL-21or MethA-GFP cells.

To assess the in vivo effects of IL-21 on tumor growth, B16F1-IL-21 or MethA-IL-21 tumor cells were inoculated i.d. into the flank of syngenic mice. As shown in FIG. 22A, no tumor formation was detected in any of the C57BL/6 mice inoculated with B16F1-IL-21 tumor cells for more than 27 weeks post tumor injection. On the contrary, all C57BL/6 mice bearing B16F1-GFP cells grew tumors starting as early as day 9. Control tumors increased rapidly in size and these mice had to be sacrificed two to three weeks after tumor cell inoculation due to heavy tumor burden. In the MethA model, small but palpable tumor masses were detected one week post tumor inoculation with either MethA-IL-21 or MethA-GFP cells in Balb/C mice (FIG. 22B). However, MethA-IL-21 tumors gradually reduced in size starting from week two (day 11) and eventually regressed completely in 100% of mice, whereas 80% of control MethA-GFP tumors continued to grow in size until the mice were sacrificed. These results show that the presence of IL-21 at the tumor microenvironment triggers potent immune responses that lead to rejection of both immunogenic and non-immunogenic tumors.

IL-21 Cannot Prevent Tumor Growth in Scid and Nude Mice

Figures 23A, 23B:
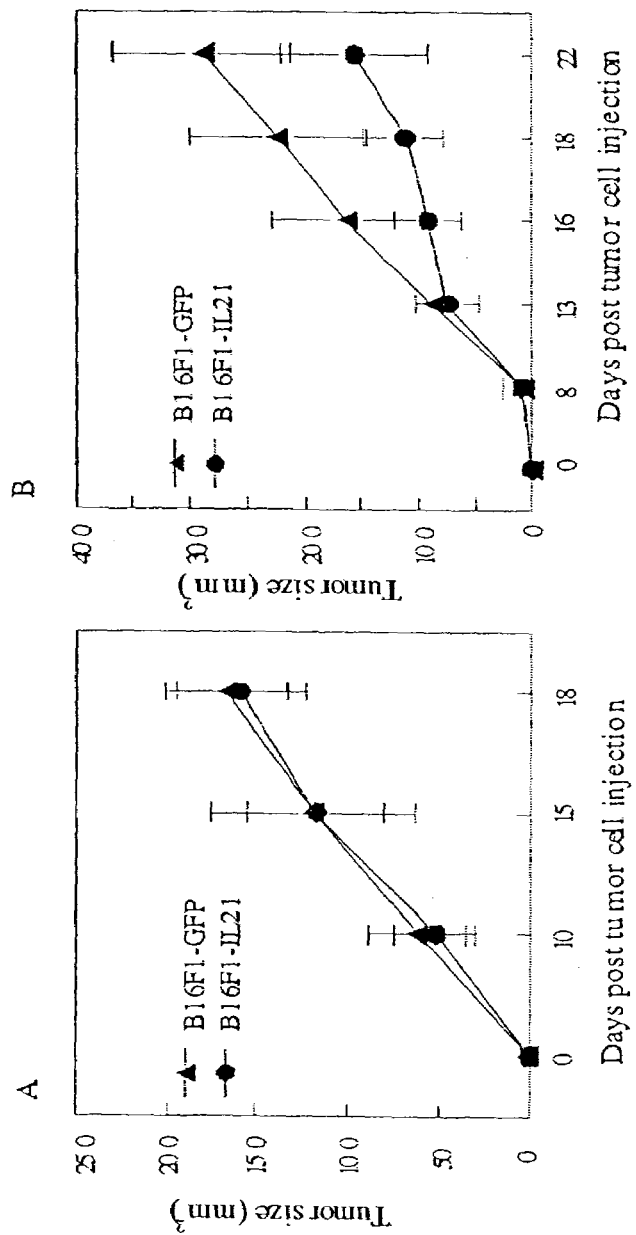
FIGS. 23A–23B are linear graphs depicting the changes in B16F1-IL-21 tumor growth in scid and nude mice with respect to number of days after injection of B16F1-IL-21 cells. B16F1-IL-21 and B16F1-GFP tumor cells ($10^5$/mouse) were injected into C57BL/6 scid (A) or C57BL/6 nude (B) mice. Tumor size was monitored twice weekly.

In order to determine the relative roles of the cellular and humoral immune responses in the rejection of IL-21-transduced tumor cells, equal numbers ($10^5$) of B16F1-IL-21 or control B16F1-GFP cells were injected into T and B cell deficient (scid) mice. Both B16F1-IL-21 and B16F1-GFP cells showed similar growth kinetics in scid mice (FIG. 23A), indicating that lymphocytes (B and/or T cells) are required for the IL-21 mediated tumor rejection. The role of T cells was also confirmed in experiments with C57BL/6 nude/nude mice. As shown in FIG. 23B, all nude mice inoculated with B16F1-IL-21 cells developed tumors, albeit with slower growth kinetics. Taken together, these results indicate that IL-21 mediated anti-tumor responses require the participation of the adaptive immunity.

Figures 25A, 25B, 25C:
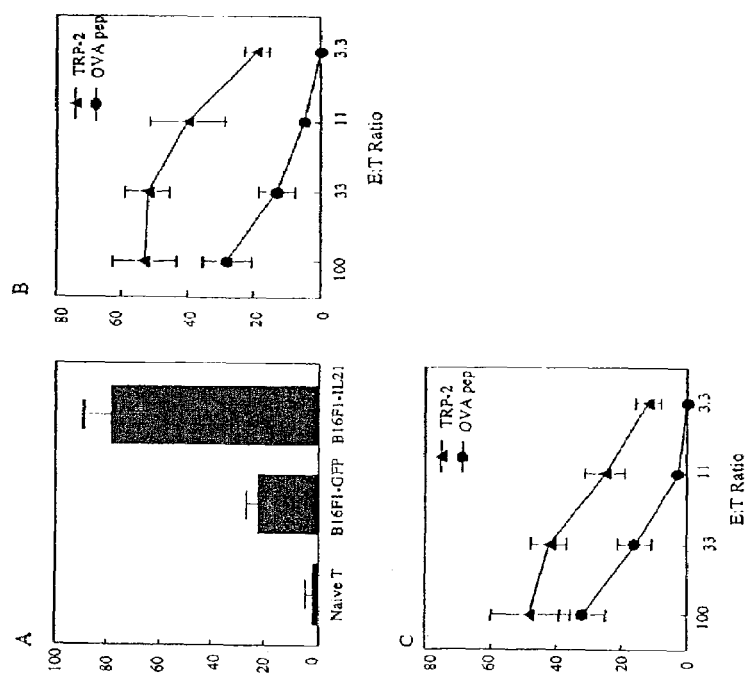
FIGS. 25A–25C are graphs showing TRP-2 specific T cell responses in B16F1-IL-21 injected mice. (A) Equal numbers of splenocytes ($2$–$4\times10^5$) from mice injected with either B16F1-IL-21 or B16F1-GFP were stimulated with 5 μg/ml of TRP-2 peptide in the presence of 20 U of IL-2 in an ELISPOT plate pre-coated with anti-IFNγ Ab. After 24 hours, the plate was developed and spot forming units were counted. Results are expressed as number of spot forming units/million of splenocytes (SPU/million splenocytes). (B) Cytolytic activity of splenocytes from B16F1-IL-21 or (C) control B16F1-GFP injected mice were tested against RMA-S cells pulsed with TRP-2 or OVA peptide (control). Cytolytic activity was measured by standard 4-hr Cr$^{51}$ Release Assay

CD8$^+$ T, but not CD4$^+$ T Cells are Required for IL-21 Mediated Tumor Rejection To further dissect which T cell subset(s) is (are) important for the I-21 induced effect, in vivo depletion of lymphocyte subpopulations by administering anti-CD4 or anti-CD8 mAbs was performed. As shown in FIG. 25A, B16F1-IL-21 tumors did not grow in CD4$^+$ T cell depleted mice and in control rat IgG treated mice. However, palpable tumors grew out in seven out of ten CD8$^+$ T cell depleted mice suggesting that CD8$^+$ but not CD4$^+$ T cells are necessary for the IL-21 induced anti-tumor response. Of interest, the growth of B16F1-IL-21 in CD8$^+$ T cell depleted mice was significantly delayed suggesting that cells other than CD8$^+$ T cells may be responsible for the suppression of early phase tumor growth.

NK Cells are Required for the IL-21 Induced Anti-tumor Response

Accumulated experimental evidence supports the role of NK cells as first line of defense in promoting anti-tumor immunity (Smyth, M. J. et al. (2001) *International Immunology* 13:459–463; Smyth, M. J. et al. (2002) *Curr. Opin. Immunol.* 14:165–171; Smyth, M. J. et al. (2002) *Blood.* 99:1259–1266). This possibility was examined by injecting equal numbers of B16F1-IL-21 tumor cells into NK cell depleted mice or control C57BL/6 mice. No detectable tumor formation was observed in control C57BL/6 mice, whereas, all of the NK cell depleted mice grew out tumors two weeks post B16F1-IL-21 tumor cell inoculation. This result shows that NK cells, in addition to CD8$^+$ T cells, are necessary for IL-21 induced anti-tumor response.

Figures 26A, 26B:
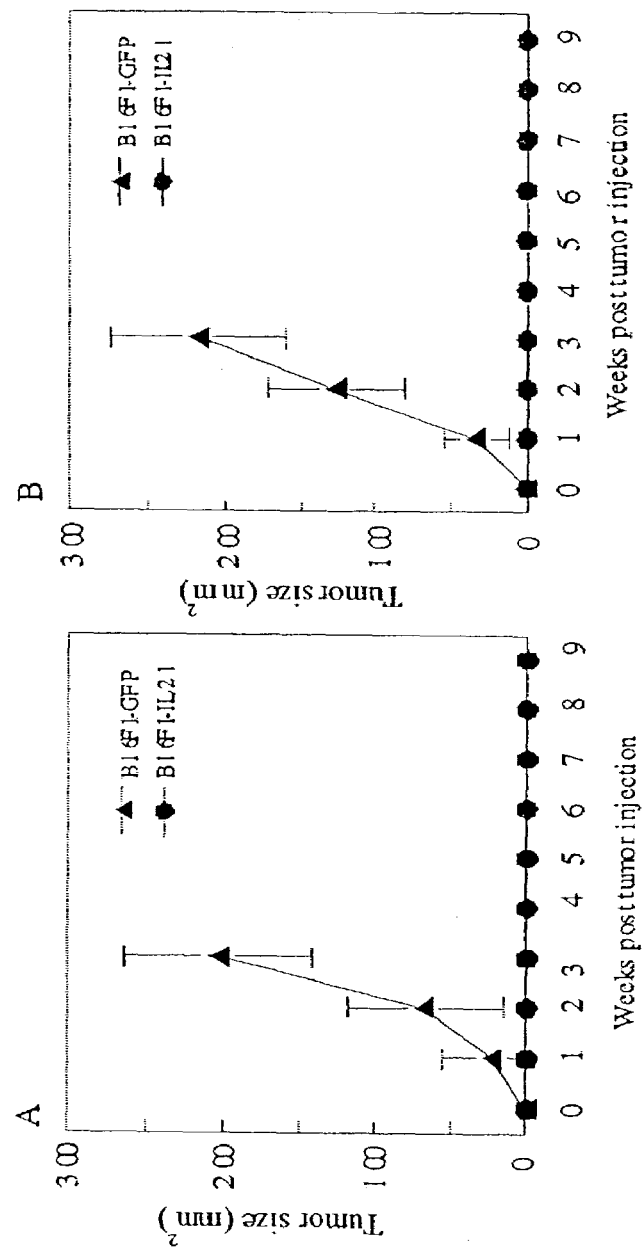
FIGS. 26A–26B are linear graphs depicting the in vivo growth of B16F1-IL-21 cells in IFNγ$^{-/-}$ and IL-10$^{-/-}$ mice. (A) IFNγ$^{-/-}$ mice or (B) IL-10$^{-/-}$ mice were injected with $10^5$ of either B16F1-IL-21 or B16F1-GFP tumor cells and the tumor growth was monitored twice weekly.

IL-21 Supports the Generation of IFNγ Secreting Tumor Antigen Specific T Cells and Enhances Tumor Antigen Specific CTL Activity It has been recently demonstrated that a nonameric peptide consisting of residues 180–188 of normal melanocyte differentiation antigen tyrosinase-related protein 2 (TPR-2), is one of the tumor rejection antigens for the B16 melanoma that is recognized by B16 melanoma-reactive cytotoxic T lymphocytes (van Elsas, A. et al. (2001) supra; Sutmuller, R. P. (2001) *J. Exp. Med.* 194:823–832). TPR-2 peptide was used to evaluate the in vivo effect of IL-21 on T cell responses. Splenocytes from mice injected with either IL-21 or GFP expressing B16F1 cells were stimulated in vitro with TRP-2 peptide in an IFNγ ELISPOT assay. As shown in FIG. 26A, the number of IFNγ producing cells in B16F1-IL-21 injected mice was 3-fold higher than that of B16F1-GFP injected mice. To further characterize IL-21 mediated anti-tumor T cell responses, splenocytes from either IL-21 or GFP expressing tumor-injected mice were first stimulated in vitro with TRP-2 peptide as described herein and then used for in vitro CTL assays. B16F1 cell line used in the experiments described herein expresses low level of MHC class I molecules, as determined with flow cytometry (van Elsas, A. et al. (2001) supra; Sutmuller, R. P. (2001) supra.; Lim, Y. S. et al. (1998) *Molecules & Cells* 8:629–636). Therefore, RMA-S cells were used as antigen presenting cells in our CTL assays. As shown in FIG. 26B, splenocytes from B16F1-IL-21 injected mice had enhanced cytolytic activity towards TRP-2 peptide pulsed RMA-S cells compared to GFP expressing tumor (FIG. 26C) at all E:T ratios, despite some cross-reactivity observed towards OVA peptide. These results indicate that IL-21-mediated tumor rejection supports the development of tumor antigen-specific cytolytic T cell responses. TRP-2 is one of the antigens that is shared between B16F1 tumor cells and normal malenocytes, thus CTLs detected here are actually autoreactive T cells. Indeed, 10–20% of C57BL/6 mice developed local hair and skin depigmentation at the site of B16F1-IL-21 tumor cell but not control cell injection (data not shown).

IL-21 Induced Anti-tumor Response is Independent of IFN-γ and IL-10

Figure 27A:
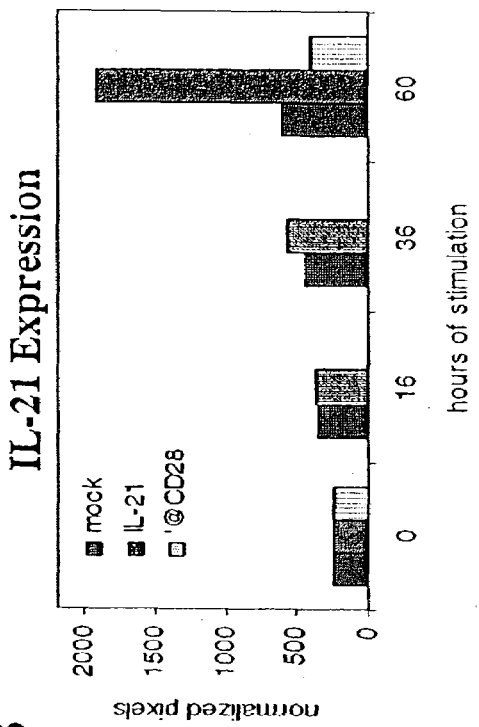
FIGS. 27A–27B are bar graphs depicting IL-21R and IL-21 expression by naïve CD8+ T cells. CD8+/CD62L+ T cells were sorted from LN of 2C TCR Tg mice and stimulated with anti-CD3 (2.5 μg/ml plate-bound), IL-21 (12.5 ng/ml) or anti-CD28 (7.5 μg/ml plate-bound). At the indicated times, cells were harvested, RNA prepared and RPA analysis performed. Samples were quantitated by phosphoimager analysis relative to an internal control. (A) Quantitation of RPA pixels for IL-21R bands. (B) Quantitation of RPA pixels for IL-21 bands.
Figure 27B:
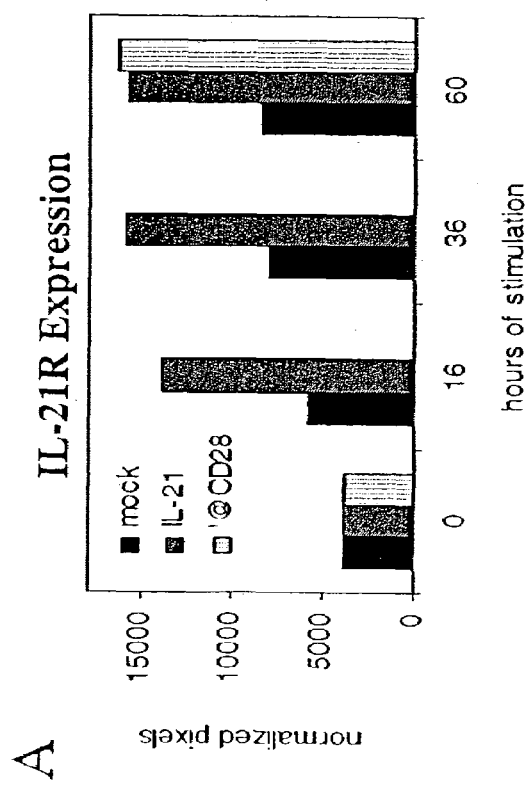

IFNγ and IL-10 have been reported previously to be important for tumor rejection (Gerard, C. M. et al. (1996) *Human Gene Therapy.* 7:23–31; Lim, Y. S. et al. (1998) *Molecules & Cells* 8:629–636). ELISOP results suggest that IL-21 enhanced tumor-specific cells producing IFNγ but not IL-10. To test the involvement of IFNγ and IL-10 in IL-21-mediated anti-tumor effect, equal numbers of B16F1-IL21 or B16F1-GFP tumor cells were injected into either IFNγ$^{-/-}$ or IL-10$^{-/-}$ mice. As shown in FIGS. 27A–27B, none of the aforementioned cytokine deficient mice formed tumors post B16F1-IL-21 cell injection. However, B16F1-GFP control cells grew out tumors in all of the IFNγ$^{-/-}$ and IL-10$^{-/-}$ mice. These data show that IL-21 mediated anti-tumor effect does not require active participation of IFNγ or IL-10.

Figures 24A, 24B:
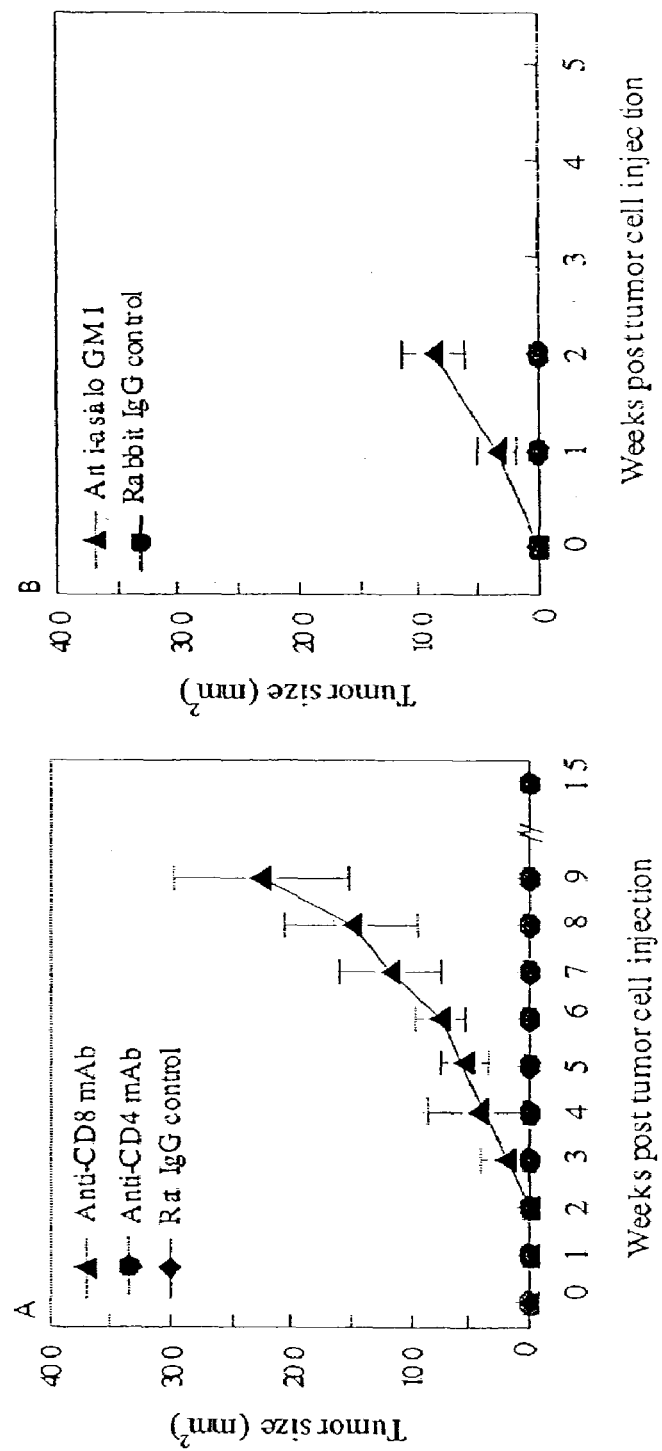
FIGS. 24A–24B are linear graphs depicting the growth of B16F1-IL-21 cells in vivo in CD4$^+$, CD8$^+$ T or NK cell depleted mice. A) C57BL/6 were depleted of CD4$^+$ or CD8$^+$ T cells by three consecutive injections of anti-CD4 or anti-CD8 mAb on days −3, −2 and −1 before tumor cell injection and every other day post $10^5$ B16F1-IL-21 and B16F1-GFP tumor cell injection. (rat IgG was used as isotype control). B) C57BL/6 were depleted of NK cells by one injection of anti-asialo GM1 Ab on day −1 before tumor cell injection and twice per week post $10^5$ B16F1-IL-21 and B16F1-GFP tumor cell injection. (rat IgG or rabbit IgG were used as isotype controls for T and NK cell depletion respectively). Tumor size was monitored twice per week as described in FIG. 23.

Cytokine gene-therapy was used to study the in vivo immunoregulatory potential of IL-21. This example shows that IL-21, when secreted at the tumor site by genetically modified B16F1 melanoma or MethA fibrosarcoma cells, fuels efficacious antitumor immune responses that require the presence of the cognate IL-21R (FIG. 23). CD8$^+$ T cells and NK cells are necessary for tumor destruction and subsequent development of tumor antigen specific T cells (FIGS. 24A and 24B). Major Th1 and Th2 cytokines, IFNγ and IL-10 respectively, do not appear to be essential for the IL-21 mediated anti-tumor responses (FIGS. 26A and 26B).

The rapid and definitive elimination of IL-21-transduced B16 melanoma tumor cells described herein is in contrast with data obtained in other cytokine gene vaccination models. Mice immunized with IL-4-, IL-5-, IL-6-, IL-12-, IFNγ, TNFα- or GM-CSF-transduced B16 vaccines displayed moderate delay in tumor formation, albeit eventually all mice succumbed to lethal tumors (Dranoff, G. et al. (1993) *PNAS* 90:3539–3543; Nagai, H. et al. (2000) *J. Invest. Dermat.* 115:1059–1064). Furthermore, GM-CSF, IL-5, IL-6, and TNF-α expressing cells caused significant side effects, ranging from hepatosplenomegaly, wasting and shivering, to death. To date, only IL-2 and IL-10 have been reported in the literature to induce complete regression of transduced B16 tumors in vivo (Dranoff, G. et al. (1993) supra; Gerard, C. M. (1996) *Human Gene Therapy* 7:23–31). In the studies described herein, syngeneic mice injected with live B16F1-IL-21 or MethA-IL-21 transduced tumor cells did not develop clinically overt tumor for a period of more than 27 weeks post tumor inoculation. Furthermore, flow cytometry analysis of lymphoid cells from spleens and lymph nodes removed from immunized mice did not show any major changes in cell population (data not shown), suggesting that the paracrine secretion of IL-21 at the tumor microenvironment orchestrates efficacious anti-tumor responses without causing detectable systemic side effects.

B16F1-IL-21 tumor grew out in IL-21R$^{-/-}$ mice but not in C57BL/6 (control) mice. This strongly indicates that IL-21 and IL21R interaction is critical for the IL-21-mediated effect despite of the apparent redundancy in IL-21R signaling pathway with other cytokine receptors (Parrish-Novak et al. (2000) supra; Ozaki et al. (2000) supra; Asao et al. (2001) supra). The outgrowth of B16F1-IL-21 tumors in IL-21R$^{-/-}$ mice, however, should not be attributed to an intrinsic defect in T and NK cell development, as IL-21R$^{-/-}$ mice have normal NK and T cells which respond to cytokines other than IL-21 (Kasaian, M. T. et al. (2002) supra).

Innate and the adaptive immune system may participate in the immune responses against tumors. IL-21 can enhance both NK and T cell activation in vitro. The in vivo depletion experiment described herein showed that both NK cells and CD8$^+$ T cells are required for complete IL21-B16F1 tumor rejection. Involvement of NK cells in tumor surveillance is confirmed by the NK depletion experiment described herein (FIG. 24B). Given that B16F1-IL-21 cells express very low level of MHC class I molecules (data not shown), inoculation of live B16F1-IL-21 cells may generate an initial local inflammatory response. NK cells can act as a first line of defense against tumor cells (Trinchieri, G. (1994) *J. Exp. Med.* 180:417–421; Levitsky, H. I. et al. (1994) *J. Exp. Med.* 179:1215–1224; Wu, T. C. (1995) *J. Exp. Med.* 182:1415–1421). This early phase of tumor killing generates a plethora of tumor derived antigens, which in turn can be taken up by professional APCs and presented to MHC-restricted cytotoxic T cells. The contribution of NK cells to the early surveillance of B16F1-IL-21 cells before adaptive immune responses being generated is further reflected by the significantly delayed B16F1-IL-21 tumor growth in CD8$^+$ T cell depleted mice (FIG. 24A).

Evidence of the involvement of T cells in IL-21 induced tumor regression is provided by the restoration of tumor growth in nude mice (FIG. 23B). Both CD4$^+$ and CD8$^+$ T cells have been described in various tumor cell-based vaccine strategies to be important for the induction of tumor regression and the development of protective immunity (Colombo, M. P., and G. Forni (1994) *Immunology Today* 15:48–51; Hock, H. et al. (1993) *PNAS* 90:2774–2778; Hung, K. et al. (1998) *J. Exp. Med.* 188:2357–2368; Segal, B. M. et al. (2002) *J. Immunol.* 168:1–4). Studies have shown that CD4$^+$ T helper cells are required for the activation of naïve CD8$^+$ T cells (Clarke, S. R. (2000) *Journal of Leukocyte Biology.* 67:607–614). In contrast, the findings described above demonstrate that CD8$^+$ but not CD4$^+$ T cells are required for the anti-tumor response of IL-21. The findings disclosed herein appear to be consistent with recent studies that have demonstrated that eliminating CD4$^+$ T cells may actually enhance the anti-tumor effect of cytokine gene therapy in vivo (Sutmuller, R. P. et al. (2001) *Journal of Experimental Medicine.* 194:823–832; Nagai, H. et al. (2000) *Journal of Investigative Dermatology* 115:1059–1064). IL-21 may also enhance the activation of naïve CD8$^+$ T cells by lowering the threshold of co-stimulation necessary for T cell activation, and/or augmenting antigen presentation of the IL-21R bearing APCs (Schoenberger, S. P. et al. (1998) *Nature.* 393:480–483; Bennett, S. R. et al. (1998) *Nature* 393:478–480).

Mice injected with B16F1-IL-21 tumor cells developed hair and skin de-pigmentation around the injection sites. It is likely that autoimmunity against normal mouse melanocyte was induced through a common epitope shared with B16 tumor cells in the close proximity of tumor injection sites. Using cytokine gene transduced B16 melanoma cells in conjunction with anti-CD4 depletion or CTLA-4 blockade, other investigators have also reported similar observation. However, the skin de-pigmentation is vitiligo-like, suggesting a more systemic involvement of the putative autoimmune cells against melanocytes (Sutmuller, R. P. et al. (2001) *Journal of Experimental Medicine.* 194:823–832; Nagai, H. (2000) *Journal of Investigative Dermatology.* 115:1059–1064; van Elsas, A. et al. (1999) *Journal of Experimental Medicine.* 190:355–366). TRP-2 is one of such shared epitopes between B16F1 tumor cells and normal melanocytes. As T cells with high affinity to self-antigens are deleted in the thymus, TRP-2 specific T cells escaping thymic deletion must be of low avidity. Nevertheless, B16F1-IL-21 tumor injected mice have more than three fold of TRP-2 specific T cells than B16F1-GFP (control) tumor injected mice, suggesting that IL-21 lowers the threshold for naïve T cell activation in B16F1-IL-21 injected mice.

The anti-tumor activity of IL-21 also correlates with enhanced CD8$^+$ T cell functions, as demonstrated by both increased antigen specific IFNγ production, and by augmented tumor specific CTL activities. Although IFNγ and IL-10 have both been described to play an essential role in tumor rejection, our experiments with IFNγ and IL-10 deficient mice indicate that their presence is not required for IL-21 mediated tumor rejection.

In summary, the results presented herein suggest that at least three mutually nonexclusive mechanisms underlie the IL-21-mediated anti-tumor response: (1) paracrine secretion of IL-21 in the tumor microenvironment triggers and supports the initial innate tumor surveillance mediated by NK cells; (2) IL-21 activates APCs and facilitates uptake of tumor debris and subsequent tumor antigen presentation to naïve T cells, hence the adaptive immune response by CD8+ T cells; (3) IL-21 lowers the threshold for naïve T cell activation, thereby allowing the recruitment and activation of low-affinity autoreactive T cells that escaped central tolerance.

EXAMPLE 10

IL-21 Enhances Antigen-Specific CD8+ T Cell Responses

This Example shows that an analysis of IL-21 and IL-21R mRNA expression, and the effects of IL-21 on the responses of, murine CD8+ T cells. Naive CD8+ T cells express IL-21R and expression is upregulated upon stimulation. CD8+ T cells only express detectable IL-21 mRNA when stimulated in the presence of exogenous IL-21. IL-21 specifically enhances proliferation of antigen- or anti-CD3 mAb-stimulated CD8+ T cells although it is not as potent as IL-2 at limiting levels of stimulation. However, compared to IL-2, the presence of IL-21 during in vitro priming of CD8+ T cells results in the development of effector cells with increased ability to lyse target cells and produce IFNγ. These findings support a role for IL-21 in the generation of CD8+ T cell responses.

Experimental Protocols

Reagents. Murine IL-21 was produced by transfection of COS cells and concentration of the supernatant; activity was referenced to rmIL-21 (R&D Systems, Minneapolis, Minn.) by bioassay. Equivalent volumes of concentrated mock transfectant supernatant were used as a control. IL-21R.Fc was constructed linking the predicted extracellular domain of human IL-21R to murine IgG2a carboxy tail with mutations to minimize Fc binding and complement fixation. rhIL-2 (R&D Systems, Minneapolis, Minn.), rmIL-12 (Wyeth, Cambridge, Mass.), rmIL-15 (R&D Systems), rmIL-21 (R&D Systems) were used as indicated.

Mice. 2C TCR Tg mice whose TCR is specific for the Ld allo-antigen were bred and maintained at Charles River Laboratories (Wilmington, Mass.).

RPAs

T cell assays. T cells were purified from 2C TCR Tg lymph nodes using negative selection columns (R&D Systems) or sorted based on CD8 and CD62L expression. Purified T cells (2×10$^5$/ml were stimulated with plate-bound anti-CD3 mAb (2C11; Wyeth, Cambridge, Mass.) or irradiated Balb/c splenocytes (2000R; 1–5×106/ml) and cytokines as indicated. Proliferation was determined by 3H-thymidine incorporation (1 uCi/well). For priming, cultures were set as above with the indicated cytokines for 4–6 days. Cells were harvested, washed, counted and used in 4 hr CTL assays with 5×10$^3$ 51Cr-labeled P815 (specific) or EL4 (non-specific) targets at the effector:target ratios noted or restimulated on anti-CD3 mAb coated plates (1 µg/ml) for 40 hrs.

IL-21R and IL-21 expression by CD8+ T cells. Previous reports have shown lymphoid-restricted expression of IL-21R and IL-21 expression by activated human CD4+ T cells. Using RNAse protection assays we have analyzed the expression of IL-21R and IL-21 mRNA by naïve murine CD8+ T cells. CD8+CD62L+2C TCR+ cells were sorted and stimulated with anti-CD3 mAb in the presence of mock- or IL-21-transfected COS supernatant or anti-CD28 mAb and RNA was prepared for IL-21R or IL-21 RNAse protection assays (FIG. 27A).

Freshly isolated CD8+ T cells expressed IL-21R mRNA implying that these cells are capable of responding to IL-21. Quantitation of signal intensity relative to an internal standard showed that TCR-mediated activation resulted in ~2-fold increase in IL-21R mRNA levels (FIG. 27A). TCR-activation with CD28 costimulation resulted in ~4-fold increase of IL-21R mRNA, suggesting that physiologic, 2-signal activation of CD8+ T cells would result in up-regulation of IL-21 R expression and increased sensitivity to IL-21. Interestingly, the presence of IL-21 during stimulation also induced a ~4-fold increase in IL-21R expression, providing evidence for a mechanism for IL-21 to amplify IL-21-responsiveness during CD8+ T cell activation. The expression of IL-21R by naïve CD8+ T cells distinguishes it from receptors of other cytokines which also act on CD8+ T cells such as those for IL-2, IL-12 or IL-15 which require activation for expression. Nearly identical results were observed in non-transgenic CD8+ T cells (data not shown).

Figures 28A, 28B, 28C, 28D:
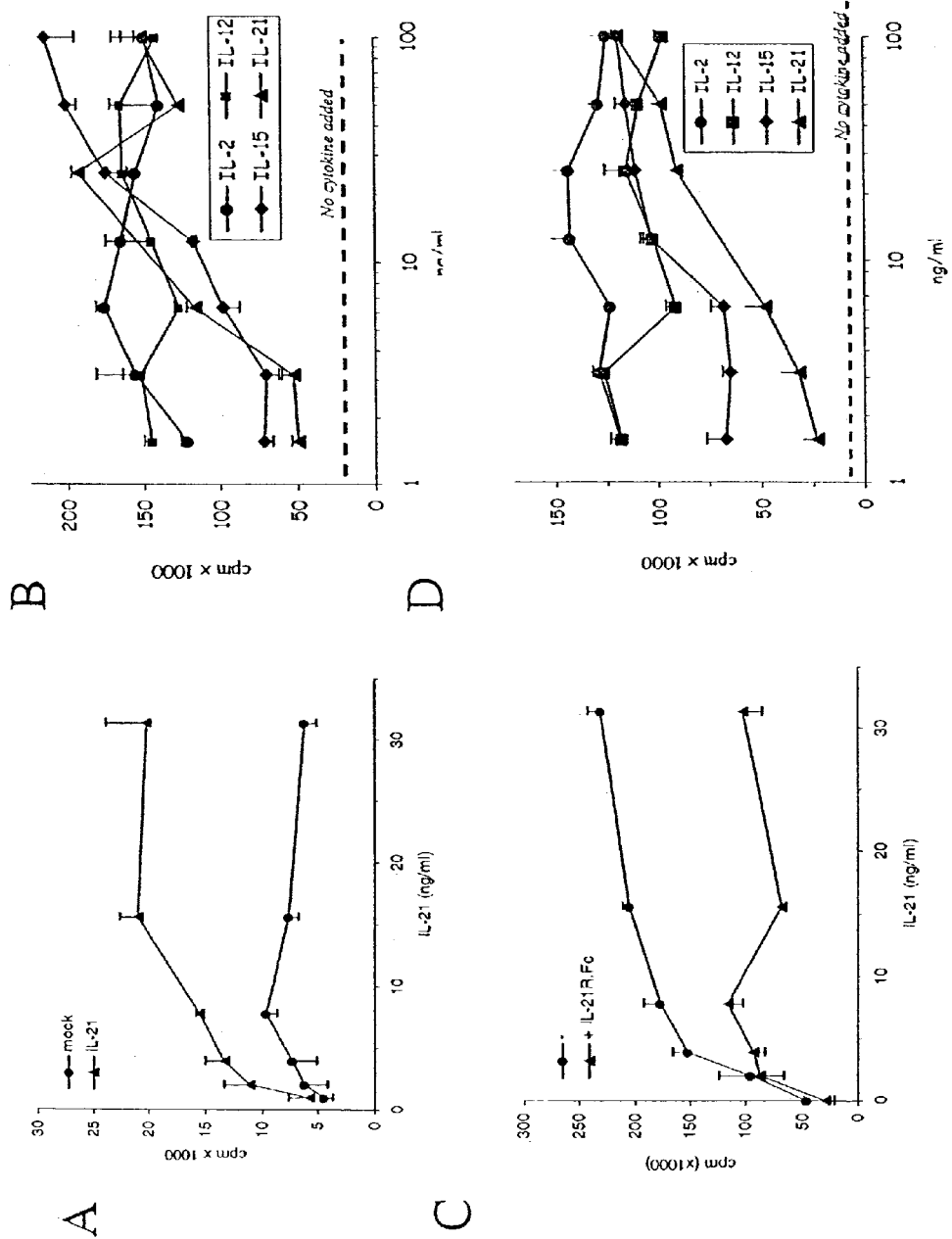
FIGS. 28A–28D are linear graphs depicting the effects of IL-21 on proliferation of CD8+ T cells. (A) IL-21 enhances antigen stimulation of CD8+ T cells. Purified 2C CD8+ T cells were stimulated for 72 hrs with irradiated Balb/c splenocytes at 5:1 APC:T ratio with the indicated amount of IL-21 or equivalent dilution of mock-transfected supernatant (representative experiment, n=5). (B) Effect of IL-21 vs IL-2, IL-12, IL-15 on antigen stimulation. 2C T cells were stimulated with 3:1 T-depleted APC:T ratio and the indicated concentration of cytokine (n=3). (C) IL-21 acts directly on CD8+ T cells to specifically enhance proliferation. 2C CD8+ T cells were stimulated on anti-CD3-coated plates (2.5 μg/ml) with the indicated titer of IL-21 +/− mIL-21R.Fc (20 μg/ml) (n=3). (D) Effect of IL-21 vs IL-2, IL-12, IL-15 on anti-CD3 mAb stimulation (5 μg/ml plate-bound).

IL-21 mRNA expression was analyzed from the same purified murine CD8+ T cells. Naive, anti-CD3, or anti-CD3/anti-CD28 mAb-activated murine CD8+ T cells were found not express significant IL-21 mRNA (FIG. 28B). This is in agreement with results using human CD8+ T cells and contrasts with observations in CD4+ T cells where activation has been shown to up-regulate IL-21 mRNA expression. Interestingly, stimulation with anti-CD3 mAb and exogenous IL-21 resulted in strong upregulation of IL-21 mRNA expression (2-fold after 36 hours and 8-fold after 60 hours of stimulation) showing that CD8+ T cells are capable of producing this cytokine.

Thus, CD8+ T cells express IL-21R mRNA, and in the presence of exogenous IL-21 up-regulate further IL-21R expression as well as de novo IL-21 expression. Activated CD4+ T cells are the likely source of the initial IL21 driving these events. In this way, IL-21 is similar to IL-2 which is also produced predominantly by CD4+ T cells and utilized by CD8+ T cells. Our results suggest a mechanism exists for maintaining IL-21 responsiveness during CD8+ T cell activation independent of CD4+ T cell-derived IL-21.

IL-21 Enhances Proliferation of CD8+ T Cells.

Figures 29A, 29B, 29C:
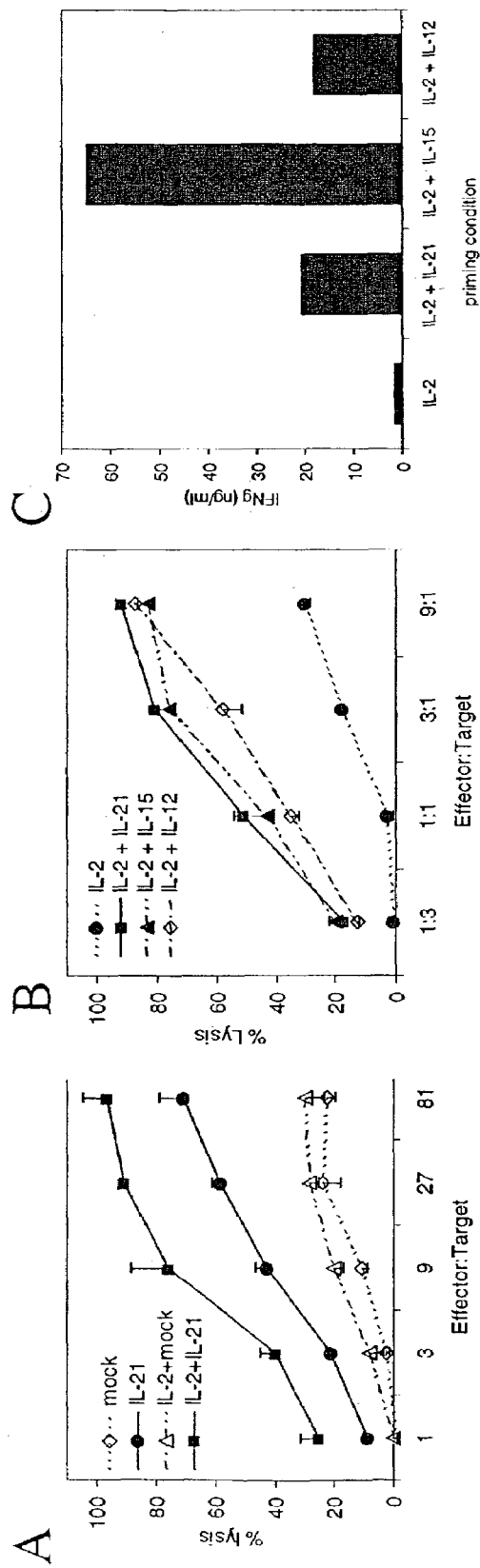
FIGS. 29A–29C are graphs showing the effects of IL-21 on development of CD8+ T cell effector functions. (A) IL-21 enhances CTL generation. 2C T cells were stimulated with irradiated APCs (APC:T) and IL-2 (10 U/ml), IL-21 (titer) or the equivalent dilution of mock supernatant for 4 days then washed, counted and set up in a 4 hr CTL assays using 51-Cr-labeled P815 as specific targets (representative experiment, n=3). (B) IL-21 is comparable to IL-12, IL-15 for inducing lytic activity from CD8+ T cells. 2C CD8+ T cells were stimulated and assayed for CTL activity as in (A) using IL-2 (5 ng/ml), IL-15 (50 ng/ml), IL-12 (5 ng/ml), IL-21 (25 ng/ml). (C) IL-21 during priming results in increased ability to produce IFNg. 2C T cells were stimulated as indicated in (B) for 5 days then washed and restimulated for on anti-CD3-coated plates (1 μg/ml). IFNg ELISAs were done on 40 hr supernatants.

IL-21 has been shown to augment the proliferation of human B cells stimulated with anti-CD40 and human and murine T cells stimulated with immobilized anti-CD3 mAb [1, 2]. Here, we analyzed the effect of IL-21 on antigen-stimulation of purified CD8+ murine T cells and found that proliferation of 2C CD8+ T cells was enhanced by IL-21 in a dose-dependent manner (FIG. 29A). IL-21 exhibited similar potency to IL-15, but was not as potent as IL-2 or IL-12 (FIG. 29B).

Because IL-21 can affect B cell function [1], the next experiment assesses whether IL-21 was augmenting 2C CD8+ T cell proliferation by acting directly on T cells or indirectly via effects on the APCs in this system. Purified 2C CD8+ T cells were stimulated with immobilized anti-CD3 mAb in the presence of increasing amounts of IL-21 (FIG. 28C). As with antigen responses, IL-21 enhanced CD8+ T cell proliferation to anti-CD3 stimulation in a dose-dependent manner. While this does not rule out a possible effect of IL-21 on APCs, it does support that this cytokine can act directly on T cells to modulate their function. Comparison of cytokine effects using anti-CD3 stimulation of CD8+ T cells revealed that IL-21 and IL-15 induce similar levels of proliferation, however IL-2 and IL-12 are more potent than IL-21 at inducing proliferation (FIG. 28D).

Because the IL-21 used in the majority of these studies was supernatant concentrated from COS transfectants, an IL-21R.Fc fusion protein was used to specifically neutralize IL-21 responses. ELISAs were done to show that mIL-21R.Fc bound to mIL-21, and that it was capable of neutralizing binding of IL-21 to its receptor (data not shown). 2C CD8+ T cells were stimulated with immobilized anti-CD3 mAb and increasing amounts of IL-21 in the presence or absence of IL-21R.Fc (FIG. 28C). IL-21-induced responsiveness was inhibited by the addition of soluble IL-21R.Fc showing that the enhanced proliferation observed in the presence of IL-21-transfectant supernatant was specifically due to IL-21. IL-21R.Fc had no effect on IL-2 or IL-15-mediated proliferation (data not shown).

IL-21 specifically enhanced antigen-induced proliferation of murine CD8+ T cells, on average resulting in 3-fold and 6-fold increased proliferation with antigen or anti-CD3 stimulation, respectively (n=5). This may be the result of comparatively lower levels of IL-21R expression, competition for gamma c in the case of IL-2 and IL-15, or the biological effect of this cytokine. The data shown here extends our previous results showing IL-21 enhanced proliferation of allo-antigen stimulation of unseparated T cells and underscores the potential importance of IL-21 in physiologic responses mediated by CD8+ T cells. In contrast to its ability to potentiate CD8+ T cell proliferation, IL-21 does not support the growth of murine NK cells and inhibits IL-15-mediated NK cell growth. These results suggest that IL-21 may activate distinct signaling programs in different cell types. In agreement with results using unseparated T cells, it was found that IL-21 was most effective at augmenting the proliferation of purified CD8+ T cells at suboptimal levels of anti-CD3 or antigen stimulation (data not shown). This suggests that IL-21 serves as an accessory signal enhancing the sensitivity of cells responding to limiting antigen. Like IL-2, IL-21 is made by activated CD4+ T cells and acts on CD8+ T cells to enhance their proliferation and may contribute to the T-helper activity attributed to CD4+ T cells. Thus, although IL-21 does enhance CD8+ T cell proliferation it is not as potent as T-cell-derived IL-2 or macrophage-derived IL-12 suggesting non-redundant roles for these cytokines.

IL-21 Enhances Lytic Activity of CD8+Effector T Cells.

Having demonstrated that IL-21 enhances CD8+ T cell proliferation, we next examined the effects of IL-21 on CD8+ T cell differentiation. 2C TCR Tg CD8+ T cells were primed in vitro in the presence of the indicated cytokine(s) then harvested and equal numbers of cells were assayed for CTL activity (FIG. 29A). The presence of IL-21 during priming resulted in the generation of CD8+effector T cells with higher lytic activity on a per cell basis than cells primed in the absence of IL-21. This increased lytic activity was even more pronounced when IL-2 was also present during priming (FIG. 29B). None of these priming conditions resulted in the ability to kill non-specific target cells (data not shown). Thus, IL-21 potently enhances the development of antigen-specific CD8+ T cell effector function. Other cytokines such as IL-12 and IL-15 have also been shown to enhance CTL differentiation. IL-21 was compared to these cytokines and was comparable in its ability to induce potent CTLs (FIG. 29B).

Previously, we have shown that IL-21 can augment IL-15-induced development of allo-antigen specific CTL and IL-15-induced NK lytic activity. The data presented here, using defined antigen-specific priming and target cells, extends this result by showing that IL-21 alone or in combination with IL-2 can enhance CTL development from naïve CD8+ T cells. Several mechanisms could account for this including increased sensitivity to antigen levels, increased expression of adhesion molecules or increased expression of granule enzymes. Studies are underway to examine these possibilities, preliminary data suggests that IL-21 induced higher granzyme A mRNA expression. Importantly, although IL-2 was much more potent than IL-21 in stimulating CD8+ T cell proliferation, priming in the presence of IL-21 generated significantly more lytic activity. Despite the fact they share homology, a receptor chain and are both made by CD4+ T cells, the findings presented here underscore the unique roles of IL-2 and IL-21 and suggest an important role for IL-21 in the generation of CD8+ T cell responses.

IL-21 CD8+ T Cell IFNgamma (or IFNg) Production.

In addition to CTL activity, differentiated CD8+ effector T cells secrete high levels of IFNg when restimulated with antigen. Therefore, we analyzed whether IL-21 present during priming modulated the ability of CD8+ T cells to produce IFNg and compared this to other cytokines known to affect CD8+ T cell responses. 2C TCR Tg T cells were primed with antigen/APCs, IL-2 and the indicated cytokine for 5 days then equal numbers of cells were restimulated with anti-CD3 mAb (FIG. 29C). IL-21 treatment during CD8+ T cell priming resulted in the generation of cells producing higher titers of IFNg than cells primed in the absence of IL-21 (13-fold increase). Using cytokine doses that generated equivalent CTL activity, CD8+ T cells primed in the presence of IL-12 or IL-21 produced similar titers of IFNg IL-15 was most effective at inducing IFNg producing CD8+ T cells. As both IL-15 and IL-21 similarly enhanced the development of CD8+ T cell lytic activity (FIG. 29B), this differential ability to induce IFNgamma production suggests non-redundant roles for these related cytokines. These results are particularly interesting as IL-21 has recently been shown to antagonize IL-12-induced IFN-gamma production by CD4+ T cells. Thus, IL-21 plays opposing roles in the differentiation of CD4+ and CD8+ T cells into IFNg-producing cells. This is consistent with the ability of CD8+ T cells to produce IFNg in an IL-12/Stat4 independent manner. In conclusion, exposure to IL-21 results in increased ability to secrete IFNg consistent with its role as differentiation factor for CD8+ T cells.

The experiments described herein show that IL-21 is a potent growth and differentiation factor for CD8+ T cells responding to antigen. IL-21R-deficient animals have functional CD8+ T cells. This finding, coupled with the data presented herein, implies that IL-21 responses are not required for CD8+ T cell development/maintenance but rather that IL-21 augments the generation of effector function. Like IL-2, IL-21 is made by activated CD4+ T cells and our results comparing the actions of these two cytokines suggest that although IL-2 potently drives the proliferation of CD8+ T cells, IL-21 is much more effective at promoting CD8+ T effector differentiation. Recently, IL-21 has been shown to be produced primarily by Th2 cells, suggesting a mechanism for the development IFNg-producing CTLs during Th2 responses. IL-15 is similar to IL-21 in its ability to induce naïve cell proliferation and CTL development but is much more effective at eliciting IFNg production. Like IL-2, IL-12 also induces strong CD8+ T cell proliferation and like IL-21 it induces potent CTL activity and IFNg production. Thus IL-2, IL-12, IL-15 and IL-21 are effective at enhancing different aspects of naïve CD8+ T cell responses. In addition, these cytokines are made by different cell types: IL-2 and IL-21 are secreted by activated CD4+ T cells while IL-12 is made by activated macrophages and IL-15 is produced by stromal cells, endothelial cells as well as macrophages. Taken together, this suggests that IL-2, IL-12, IL-15 and IL-21 act at distinct phases and sites of immune responses are not redundant. We have previously proposed that IL-21 may be a mediator of the transition between innate and adaptive immune responses, the data presented here showing enhancement of CD8+ T cell responses support this hypothesis. Given its potent effects on CD8+ T cells, it will be interesting to analyze the role of IL-21 in CD8+ responses to tumors and viral infections in vivo.

EXAMPLE 11

Primary Macrophages Express IL-21R and Respond to IL-21 by Proliferating and Secreting Increased Levels of Cytokines and Chemokines This Example describes the finding that IL-21 acts as a proliferation factor for hematopoietic cells specifically promoting the growth of macrophages and bone marrow progenitor cells.

The effect of IL-21 alone and in combination with other factors in modulating hematopoeitic cell growth was examined. It was found that IL-21 acts as a proliferation factor for mouse and human hematopoietic cells specifically promoting the growth of macrophage colonies in methylcellulose from lineage negative murine bone marrow progenitors. IL-21 also acts to enhance proliferation of human CD34+ cells and results in increased expression of the macrophage specific marker CD14. Utilizing CD14+ cells sorted from human bone marrow, it has been shown by RNAse Protection Analysis (RPA) that the IL-21R is expressed on macrophages, and is upregulated by TNF and IL-1 following growth in GMCSF. Thus, suggesting a role of other inflammatory cytokines in regulating IL-21 responsiveness. Expression of IL-21R protein on mouse and human macrophages has been detected using FACS analysis. IL-21 acts directly on these cells resulting in activation, growth and increased secretion of chemokines and cytokines.

Taken together, these results show that the IL-21/IL-21R complex is important in regulating macrophage growth and function, and in influencing macrophage responses at inflammatory sites. Macrophages play an important role in cell-mediated immunity, therefore IL-21 treatment could enhance response in immune-compromised patients. Macrophages also are involved in host response to malignant tumors, and are important antigen-presenting cells therefore can play role in presenting specific tumor antigens. Macrophages are phagocytic and motile, able to engulf large numbers of foreign particles, as in a systemic infection.

The contents of all references, pending patent applications and published patents, cited throughout this application are hereby expressly incorporated by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A method of treating an arthritic disorder in a subject, comprising administering to the subject an antibody or antigen-binding fragment thereof that binds to IL-21R in an amount sufficient to inhibit or reduce immune cell activity in the subject, thereby treating the arthritic disorder, wherein said IL-21R has a sequence at least about 90% identical to the amino acid sequence of SEQ ID NO:2 and is capable of binding to an IL-21 polypeptide.

2. The method of claim 1, further comprising administering to the subject a therapeutic agent selected from the group consisting of cytokine inhibitors, growth factor inhibitors, immunosuppressants, anti-inflammatory agents, metabolic inhibitors, enzyme inhibitors, cytotoxic agents, and cytostatic agents.

3. The method of claim 2, wherein the therapeutic agent is selected from the group consisting of TNF antagonists, anti-TNF agents, IL-12 antagonists, IL-15 antagonists, IL-17 antagonists, IL-18 antagonists, IL-22 antagonists, T cell-depleting agents, B cell-depleting agents, cyclosporin, FK506, CCI-779. etanercept, infliximab, rituximab, adalimumab, prednisolone, azathioprine, gold, sulphasalazine, hydroxychloroquine, minocycline, anakinra, atabacept, methotrexate, leflunomide, rapamycin, rapamycin analogs, Cox-2 inhibitors, cPLA2 inhibitors, NSAIDs, p38 inhibitors, antagonists of B7.1, B7.2, ICOSL, ICOS, and CD28, and CTLA4 agonists.

4. The method of claim 1, wherein the arthritic disorder is selected from the group consisting of rheumatoid arthritis, juvenile rheumatoid arthritis, osteoarthritis, psoriatic arthritis, and ankylosing spondylitis.

5. The method of claim 4, wherein the arthritic disorder is rheumatoid arthritis.

6. The method of claim 4, wherein said arthritic disorder is psoriatic arthritis.

7. The method of claim 4, wherein said arthritic disorder is osteoarthritis.

8. The method of claim 4, wherein said arthritic disorder is juvenile rheumatoid arthritis.

9. The method of claim 4, wherein said arthritic disorder is ankylosing spondylitis.

10. The method of claim 1, wherein the subject is a mammal.

11. The method of claim 1, wherein said IL-21R comprises the sequence of SEQ ID NO:2.

12. The method of either claim 1 or 4, wherein said antibody or antigen-binding fragment thereof is administered subcutaneously or intravenously.

13. The method of either claim 1 or 4, wherein said subject is a human.

14. The method of either claim 1 or 4, wherein said IL-21R has a sequence at least about 95% identical to the amino acid sequence of SEQ ID NO:2 and is capable of binding to an IL-21 polypeptide.

15. The method of either claim 1 or 4, wherein said IL-21R comprises the sequence of SEQ ID NO:2 from about amino acids 20–538.

16. The method of either claim 1 or 4, wherein said antibody, or antigen-binding fragment thereof, binds to an epitope found in the extracellular domain of IL-21R.

17. The method of either claim 1 or 4, wherein said antibody, or antigen-binding fragment thereof, is a neutralizing antibody.

18. The method of either claim 1 or 4, wherein said antibody, or antigen-binding fragment thereof, is selected from the group consisting of a monoclonal antibody, a polyclonal antibody, a chimeric antibody, a single-chain antibody, a CDR-grafted antibody and a humanized antibody.

19. The method of either claim 1 or 4, wherein said antibody, or antigen-binding fragment thereof, is a human antibody.

20. A method of ameliorating a symptom associated with arthritis in a subject, comprising administering to the subject an antibody or antigen-binding fragment thereof that binds to IL-21R in an amount sufficient to ameliorate the symptom in the subject, wherein the IL-21R has a sequence at least about 90% identical to the amino acid sequence of SEQ ID NO:2 and is capable of binding to an IL-21 polypeptide.

21. The method of claim 20, wherein said antibody, or antigen-binding fragment thereof, is administered therapeutically.

22. The method of claim 20, wherein said antibody, or antigen-binding fragment thereof, is administered prophylactically.

23. The method of claim 20, wherein said IL-21R has a sequence at least about 95% identical to the amino acid sequence of SEQ ID NO:2 and is capable of binding to an IL-21 polypeptide.

24. The method of claim 20, wherein said IL-21R comprises the sequence of SEQ ID NO:2 from about amino acids 20–538.

25. The method of claim 20, wherein said IL-21R comprises the sequence of SEQ ID NO:2.

26. The method of claim 20, wherein said antibody, or antigen-binding fragment thereof, binds to an epitope found in the extracellular domain of IL-21R.

27. The method of claim 26, wherein said arthritic symptom is associated with a disorder selected from the group consisting of rheumatoid arthritis, juvenile rheumatoid arthritis, osteoarthritis, psoriatic arthritis, and ankylosing spondylitis.

28. The method of claim 27, wherein said disorder is rheumatoid arthritis.

29. The method of claim 27, wherein said disorder is psoriatic arthritis.

30. The method of claim 27, wherein said disorder is osteoarthritis.

31. The method of claim 27, wherein said disorder is juvenile rheumatoid arthritis.

32. The method of claim 27, wherein said disorder is ankylosing spondylitis.

33. The method of claim 20, further comprising administering to the subject a therapeutic agent selected from the group consisting of cytokine inhibitors, growth factor inhibitors, immunosuppressants, anti-inflammatory agents, metabolic inhibitors, enzyme inhibitors, cytotoxic agents, and cytostatic agents.

34. The method of claim 33, wherein said therapeutic agent is selected from the group consisting of TNF antagonists, anti-TNF agents, IL-12 antagonists, IL-15 antagonists, IL-17 antagonists, IL-18 antagonists, IL-22 antagonists, T cell-depleting agents, B cell-depleting agents, cyclosporin, FK506, CCI-779, etanercept, infliximab, rituximab, adalimumab, prednisolone, azathioprine, gold, sulphasalazine, hydroxychloroquine, minocycline, anakinra, atabacept, methotrexate, leflunomide, rapamycin, rapamycin analogs, Cox-2 inhibitors, cPLA2 inhibitors, NSAIDs, p38 inhibitors, antagonists of B7.1, B7.2, ICOSL, ICOS, and CD28, and CTLA4 agonists.

35. The method of either claim 20 or 26, wherein said antibody or antigen-binding fragment thereof is administered subcutaneously or intravenously.

36. The method of either claim 20 or 26, wherein said subject is a human.

37. The method of either claim 20 or 26, wherein said antibody, or antigen-binding fragment thereof, is a neutralizing antibody.

38. The method of either claim 20 or 26, wherein said antibody, or antigen-binding fragment thereof, is selected from the group consisting of a monoclonal antibody, a polyclonal antibody, a chimeric antibody, a single-chain antibody, a CDR-grafted antibody and a humanized antibody.

39. The method of either claim 20 or 26, wherein said antibody, or antigen-binding fragment thereof, is a human antibody.

40. A method of treating rheumatoid arthritis in a subject, comprising administering to the subject an antibody or antigen-binding fragment thereof that binds to IL-21R in an amount sufficient to treat rheumatoid arthritis in the subject, wherein the IL-21R has a sequence at least about 90% identical to the amino acid sequence of SEQ ID NO:2 and is capable of binding to an IL-21 polypeptide.

41. The method of claim 40, wherein said IL-21R has a sequence at least about 95% identical to the amino acid sequence of SEQ ID NO:2 and is capable of binding to an IL-21 polypeptide.

42. The method of claim 40, wherein said IL-21R comprises the sequence of SEQ ID NO:2 from about amino acids 20–538.

43. The method of claim 40, wherein said IL-21R comprises the sequence of SEQ ID NO:2.

44. The method of claim 40, wherein said antibody, or antigen-binding fragment thereof, binds to an epitope found in the extracellular domain of IL-21R.

45. The method of claim 40, further comprising administering to the subject a therapeutic agent selected from the group consisting of cytokine inhibitors, growth factor inhibitors, immunosuppressants, anti-inflammatory agents, metabolic inhibitors, enzyme inhibitors, cytotoxic agents, and cytostatic agents.

46. The method of claim 45, wherein said therapeutic agent is selected from the group consisting of TNF antagonists, anti-TNF agents, IL-12 antagonists, IL-15 antagonists, IL-17 antagonists, IL-18 antagonists, IL-22 antagonists, T cell-depleting agents, B cell-depleting agents, cyclosporin, FK506, CCI-779, etanercept, infliximab, rituximab, adalimumab, prednisolone, azathioprine, gold, sulphasalazine, hydroxychloroquine, minocycline, anakinra, atabacept, methotrexate, leflunomide, rapamycin, rapamycin analogs, Cox-2 inhibitors, cPLA2 inhibitors, NSAIDs, p38 inhibitors, antagonists of B7.1, B7.2, ICOSL, ICOS, and CD28, and CTLA4 agonists.

47. The method of either claim 40 or 44, wherein said antibody or antigen-binding fragment thereof is administered subcutaneously or intravenously.

48. The method of either claim 40 or 44, wherein said subject is a human.

49. The method of either claim 40 or 44, wherein said antibody, or antigen-binding fragment thereof, is a neutralizing antibody.

50. The method of either claim 40 or 44, wherein said antibody, or antigen-binding fragment thereof, is selected from the group consisting of a monoclonal antibody, a polyclonal antibody, a chimeric antibody, a single-chain antibody, a CDR-grafted antibody and a humanized antibody.

51. The method of either claim 40 or 44, wherein said antibody, or antigen-binding fragment thereof, is a human antibody.

52. A method of treating an immune cell-associated pathology selected from the group consisting of an arthritic disorder, psoriasis, systemic lupus erythematosus, Crohn's disease, inflammatory bowel disease (IBD) and transplant rejection, in a subject, comprising administering to the subject an antibody against IL-21R, or an antigen-binding fragment thereof, in an amount sufficient to treat said pathology, wherein said IL-21R has a sequence at least about 90% identical to the amino acid sequence of SEQ ID NO:2 and is capable of binding to an IL-21 polypeptide.

53. The method of claim 52, wherein said IL-21R has a sequence at least about 95% identical to the amino acid sequence of SEQ ID NO:2 and is capable of binding to an IL-21 polypeptide.

54. The method of claim 52, wherein said IL-21R comprises the sequence of SEQ ID NO:2 from about amino acids 20–538.

55. The method of claim 52, wherein said IL-21R comprises the sequence of SEQ ID NO:2.

56. The method of claim 52, wherein said antibody, or antigen-binding fragment thereof, binds to an epitope found in the extracellular domain of IL-21 R.

57. The method of claim 52, wherein said pathology is psoriasis.

58. The method of claim 52, wherein said pathology is systemic lupus erythematosus.

59. The method of claim 52, wherein said pathology is IBD.

60. The method of claim 52, wherein said pathology is Crohn's disease.

61. The method of claim 52, wherein said pathology is transplant rejection.

62. The method of claim 52, wherein said antibody or antigen-binding fragment thereof is administered subcutaneously or intravenously.

63. The method of claim 52, wherein said subject is a human.

64. The method of claim 52, wherein said antibody, or antigen-binding fragment thereof, is a neutralizing antibody.

65. The method of claim 52, wherein said antibody, or antigen-binding fragment thereof, is selected from the group consisting of a monoclonal antibody, a polyclonal antibody, a chimeric antibody, a single-chain antibody, a CDR-grafted antibody and a humanized antibody.

66. The method of claim 52, wherein said antibody, or antigen-binding fragment thereof, is a human antibody.

* * * * *

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

ON THE TITLE PAGE ITEM [56] REFERENCES CITED:

Other Publications, "EMBL Database Accession No. AC002302 (Jun. 26, 1997)." should read --EMBL Database Accession No. AC002303 (Jun. 26, 1997).--.

ON THE TITLE PAGE ITEM [56] REFERENCES CITED:

Other Publications, "pseudomonas" should be italicized.

ON THE TITLE PAGE ITEM [56] REFERENCES CITED:

Other Publications, "domin" should read --domain--.

COLUMN 1:

Line 29, "a" should be deleted.

COLUMN 2:

Line 25, "subject, the" should read --subject. The--;
Line 38, "megakaryocytes," should read --megakaryocytes),--;
Line 41, "disorders," should read --disorder,--;
Line 47, "erythematosis," should read --erythematosus,--; and
Line 54, "IL-21-" should read --IL-21--.

COLUMN 3:

Line 57, "a" should be deleted.

COLUMN 6:

Line 18, "a" should be deleted.

COLUMN 7:

Line 41, "(e.g.," should read --, e.g.,--.

COLUMN 8:

Line 6, "a" should be deleted.

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

COLUMN 11:

Line 8, "tyrosine's" should read --tyrosines--;
Line 29, "match = 0.000." should read --match = 0.000,--; and
Line 38, "Mismatch = -2.003." should read --Mismatch = -2.003,--.

COLUMN 12:

Line 14, "depicts" should read --depict--.

COLUMN 13:

Line 45, "injection." should read --injection--.

COLUMN 15:

Line 14, "agent" should read --agents--; and
Line 64, "sequence" should be deleted.

COLUMN 16:

Line 5, "from about" should be deleted;
Line 46, "includes" should read --include--; and
Line 55, "a" should be deleted.

COLUMN 17:

Line 40, "cytes)." should read --cytes.--; and
Line 49, "or" (second occurrence) should read --or more--.

COLUMN 18:

Line 4, "term" should read --terms--.

COLUMN 20:

Line 24, "of 5." should read --of 5. The percent identity between two amino acid or nucleotide sequences can also be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.--.

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

COLUMN 21:

Line 44, "is" should be deleted.

COLUMN 22:

Line 46, "comprise" should read --comprises--; and "comprise" should read --comprises--; and
    Line 48, "signal" should read --single--.

COLUMN 28:

Line 16, "includes" should read --include--.

COLUMN 29:

Line 44, "a culture transformed" should read --a culture of transformed--.

COLUMN 31:

Line 3, "is" should read --are--;
    Line 6, "which in" should read --which exist in--; and
    Line 29, "An" should be deleted.

COLUMN 32:

Line 14, "additive" should read --additives--.

COLUMN 33:

Line 28, "herpesviruses," should read --herpes viruses,--.

COLUMN 34:

Line 20, "class.alpha. a" should read --class I α--.

COLUMN 36:

Line 29, "avium-" should read --avium,--.

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

COLUMN 37:

Line 60, "erythematosis," should read --erythematosus,--.

COLUMN 39:

Line 37, "erythematosis" should read --erythematosus--.

COLUMN 40:

Line 43, ")" should be deleted; and
Line 63, "TNF a)" should read --TNFα)--.

COLUMN 41:

Line 29, "210396" should read --210396)--.

COLUMN 42:

Line 26, "analogs)" should read --analogs).--.

COLUMN 43:

Line 38, "Enbrel$^{TM}$," should read --Enbrel$^{TM}$),--; and
Line 55, "Enbrel$^{TM}$;" should read --Enbrel$^{TM}$);--.

COLUMN 44:

Line 48, "an" should be deleted.

COLUMN 46:

Line 23, "123" should read --123,--.

COLUMN 48:

Line 57, "hybridizes" should read --hybridized--.

COLUMN 49:

Line 62, "Mismatch = -2.003." should read --Mismatch - -2.003,--.

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

COLUMN 50:

Line 2, "Mismatch - 0.000." should read --Mismatch = 0.000,--;
Line 7, "Box-i" should read --Box 1--; and
Line 34, "nonphosphoraled" should read --nonphosphorylated--.

COLUMN 51:

Line 16, "muscular is external" should read --muscularis externa--.

COLUMN 52:

Line 22, "collagen-induce" should read --collagen-induced--.

COLUMN 55:

Line 4, "$10^6$ B16F1-IL-21." should read --$10^6$ B16F1-IL-21,--; and
Line 45, "manufacturers" should read --manufacturer's--.

COLUMN 56:

Line 31, "biological" should read --biologically--; and
Line 65, "unite" should read --unit--.

COLUMN 58:

Line 3, "IFNγSecreting" should read --IFNγ-Secreting--;
Line 17, "IFNγELISPOT" should read --IFNγ ELISPOT--; and
Line 48, "ELISOP" should read --ELISPOT--.

COLUMN 61:

Line 38, "($2 \times 10^5$/ml" should read --($2 \times 10^5$/ml)--.

UNITED STATES PATENT AND TRADEMARK OFFICE
CERTIFICATE OF CORRECTION

PATENT NO. : 7,198,789 B2
APPLICATION NO. : 10/264634
DATED : April 3, 2007
INVENTOR(S) : Laura Carter et al.

It is certified that error appears in the above-identified patent and that said Letters Patent is hereby corrected as shown below:

COLUMN 64:

Line 6, "IFNg" should read --IFNγ--;
    Line 8, "IFNg" should read --IFNγ--;
    Line 21, "IFNg" (first occurrence) should read --IFNγ.--; and "IFNg" (second occurrence) should read --IFNγ--;
    Line 32, "IFNg" should read --IFNγ--;
    Line 34, "IFNg" should read --IFNγ--;
    Line 49, "development IFNg-producing" should read --development of IFNγ-producing--; and
    Line 54, "IFNg" should read --IFNγ--.

COLUMN 113:

Line 58, "CCI-779." should read --CCI-779,--.

Signed and Sealed this

Seventh Day of August, 2007

JON W. DUDAS
*Director of the United States Patent and Trademark Office*